(12) United States Patent
Acharya et al.

(10) Patent No.: US 10,251,778 B2
(45) Date of Patent: Apr. 9, 2019

(54) THERAPEUTICS DISPENSING DEVICE AND METHODS OF MAKING SAME

(71) Applicants: Baylor College of Medicine, Houston, TX (US); REGENTS OF THE UNIVERSITY OF CALIFORNIA, Oakland, CA (US)

(72) Inventors: Ghanashyam Acharya, Houston, TX (US); Stephen C. Pflugfelder, Houston, TX (US); Cintia S. De Paiva, Houston, TX (US); Jennifer L. Simpson, Irvine, CA (US)

(73) Assignees: Baylor College of Medicine, Houston, TX (US); REGENTS OF THE UNIVERSITY OF CALIFORNIA, Oakland, CA (US)

( * ) Notice: Subject to any disclaimer, the term of this patent is extended or adjusted under 35 U.S.C. 154(b) by 458 days.

(21) Appl. No.: 14/420,295

(22) PCT Filed: Aug. 6, 2013

(86) PCT No.: PCT/US2013/053805
§ 371 (c)(1),
(2) Date: Feb. 6, 2015

(87) PCT Pub. No.: WO2014/025792
PCT Pub. Date: Feb. 13, 2014

(65) Prior Publication Data
US 2015/0190279 A1  Jul. 9, 2015

Related U.S. Application Data

(60) Provisional application No. 61/775,891, filed on Mar. 11, 2013, provisional application No. 61/679,908, filed on Aug. 6, 2012.

(51) Int. Cl.
*A61F 9/00*  (2006.01)
*A61K 9/00*  (2006.01)
(Continued)

(52) U.S. Cl.
CPC .......... *A61F 9/0017* (2013.01); *A61K 9/0048* (2013.01); *A61K 9/0051* (2013.01);
(Continued)

(58) Field of Classification Search
CPC ............ A61F 9/0017; A61F 2210/0004; A61F 2240/005; A61F 2250/0068; A61F 2310/00383; A61K 9/0051; A61K 9/0048
See application file for complete search history.

(56) References Cited

U.S. PATENT DOCUMENTS

| | | | | |
|---|---|---|---|---|
| 5,788,957 A | * | 8/1998 | Harris | A61F 9/0017 424/423 |
| 2004/0166140 A1 | * | 8/2004 | Santini, Jr. | A61K 9/0009 424/424 |

(Continued)

FOREIGN PATENT DOCUMENTS

| | | |
|---|---|---|
| JP | 2009-142661 | 7/2009 |
| WO | 2002/055058 A2 | 7/2002 |

(Continued)

OTHER PUBLICATIONS

MedicineNet.com definition of bulbar conjunctiva, http://www.medicinenet.com/script/main/art.asp?articlekey=9898.*
(Continued)

*Primary Examiner* — Adam Marcetich
*Assistant Examiner* — Jessica R Arble
(74) *Attorney, Agent, or Firm* — Norton Rose Fulbright US LLP

(57) ABSTRACT

A therapeutics delivery system, and methods of making and using same, are disclosed for environments that rapidly clear any injected therapeutics, such as a patient's eye. The therapeutics delivery system releases the drug in a therapeutically effective concentration for a desired duration of time with a predefined drug kinetics. In one embodiment, the
(Continued)

embodiments of the present disclosure release a therapeutically effective concentration for a longer time period than other delivery systems, for instance from a day to a week. Certain embodiments comprise a therapeutics dispensing device comprising a biodissolvable hydrogel matrix for long term drug release that allows the device to be placed directly at the injured site, e.g., onto the surface at or near the injury, and retained there rather than through injection, whether locally or systematically.

28 Claims, 33 Drawing Sheets

(51) Int. Cl.
| | | |
|---|---|---|
| *B29C 33/38* | (2006.01) | |
| *B29C 39/02* | (2006.01) | |
| *A61K 47/32* | (2006.01) | |
| *A61K 47/34* | (2017.01) | |
| *A61K 47/42* | (2017.01) | |
| *B29L 31/00* | (2006.01) | |

(52) U.S. Cl.
CPC .......... *B29C 33/3842* (2013.01); *B29C 39/02* (2013.01); *A61F 2210/0004* (2013.01); *A61F 2240/005* (2013.01); *A61F 2250/0068* (2013.01); *A61F 2310/00383* (2013.01); *A61K 47/32* (2013.01); *A61K 47/34* (2013.01); *A61K 47/42* (2013.01); *B29L 2031/712* (2013.01)

(56) References Cited

U.S. PATENT DOCUMENTS

| | | | |
|---|---|---|---|
| 2007/0141106 A1* | 6/2007 | Bonutti | A61B 17/0401 424/423 |
| 2008/0002149 A1* | 1/2008 | Fritsch | G02C 7/04 351/159.02 |
| 2009/0136583 A1* | 5/2009 | Park | A61K 9/5031 424/497 |
| 2010/0069482 A1* | 3/2010 | Longo | A61K 9/0048 514/458 |
| 2010/0209478 A1* | 8/2010 | Sawhney | A61F 9/00772 424/427 |
| 2010/0216700 A1 | 8/2010 | Li et al. | |
| 2010/0278931 A1* | 11/2010 | Ashton | A61K 9/0097 424/501 |
| 2012/0014970 A1* | 1/2012 | Dana | A61K 9/0048 424/158.1 |
| 2012/0130300 A1 | 5/2012 | Stavchansky et al. | |

FOREIGN PATENT DOCUMENTS

| | | |
|---|---|---|
| WO | 2009/008946 A1 | 1/2009 |
| WO | WO 2009/042231 | 4/2009 |
| WO | 2012/019047 A2 | 2/2012 |

OTHER PUBLICATIONS

Merriam-Webster definition of reservoir, https://www.merriam-webster.com/dictionary/reservoir.*

* cited by examiner

| Cysteamine Concentration (ng/wafer) | Corneal Opacity Rate |
|---|---|
| 0 | 0% |
| 50 | 0% |
| 100 | 0% |
| 150 | 0% |
| 175 | ~1-2% |
| 200 | ~20% |
| 500 | ~100% |

FIG. 22

THERAPEUTICS DISPENSING DEVICE AND METHODS OF MAKING SAME

This application is a national phase application under 35 U.S.C. § 371 that claims priority to International Application No. PCT/US2013/053805, filed Aug. 6, 2013, which claims priority to U.S. Provisional Patent Application Ser. No. 61/679,908, filed Aug. 6, 2012, and claims priority to U.S. Provisional Patent Application Ser. No. 61/775,891, filed Mar. 11, 2013, all of which are incorporated by reference herein in their entirety.

This invention was made with government support under R01 EY011915-14 awarded by the National Eye Institute. The government has certain rights in the invention.

TECHNICAL FIELD

The present disclosure generally relates to controlled release of therapeutics in an individual, such as delivery of therapeutics locally through a dissolvable hydrogel matrix. In particular embodiments, the field of the invention includes at least cell biology, molecular biology, biomedical engineering, and medicine.

BACKGROUND OF THE DISCLOSURE

Treatment of an injury, diseases and inflammations with pharmaceuticals, e.g., drugs, often involve subjecting the whole system to the toxicity and/or adverse effects of those pharmaceuticals rather than just the injured site. This is because drugs are often administered through ingestion rather than localized delivery. As such, if the medication affects or treats only a particular part or organ in the body, it is desirable to administer the medication to only that part or organ. Such localized delivery minimizes adverse effects on other non-targeted parts or organs and reduces waste of the medication as systemic administration often requires a higher dose to achieve the same effect as localized delivery. While localized delivery of therapeutic agents to the site of injury is often the most effective mode of treatment, current modes of drug delivery are associated with peak and trough drug release profiles while sustained drug release is desirable. While localized drug delivery devices and methods are presently available, there remain several limitations to these approaches.

Localized deliveries in the eye have been utilized. The eye is a unique organ because of its anatomical structure and intrinsic physiological and defense mechanisms. The smooth and wet mucosal surface of the eye, unlike other mucosal epithelia, is directly exposed to the external environment and is prone to injury, desiccation, and pro-inflammatory stimuli. Every year more than 2.5 million eye injuries occur and 50,000 people permanently lose part or all of their vision, and approximately 3.2 million women age 50 and over and 1.68 million men age 50 and over are affected by dry eye syndrome (Eye health statistics at a glance, Compiled by American Academy of Ophthalmology, April 2011). Because of the impervious nature of the ocular surface and lacrimal clearance, targeting the drug to the appropriate site of action is usually one of the greatest challenges in drug delivery (Gipson, 2007; Singh et al., 2011; Gaudana et al., 2008). For a successful pharmacotherapy, the drug should be present at the target site (cornea or conjunctiva) in a therapeutically effective concentration for a predefined period of time. The bioavailability of the drug depends upon the physico-chemical properties of the drug, the target tissue, drug absorption, distribution, elimination, and the drug delivery system. For most of the drugs, the pharmacokinetics and efficacy is well understood, however, delivery of the drug to the target site in a therapeutically effective concentration for a stipulated period of time is the challenge.

1. Ocular Drug Delivery

Generally, medication to the eye is delivered by topical ocular, systemic, and intraocular or periocular injections. Ocular diseases are commonly treated with a topical application of drug solutions (i.e. eye drops or ointments). These conventional dosage forms account for nearly 90% of currently available marketed formulations because of their simplicity, safety and acceptance by patients. However, ocular surface barriers can limit the drug absorption and its bioavailability in the eye. Topical ocular drug administration is accomplished by eye drops, but they have only a short contact time on the eye surface. Typically, <5% of the drug can penetrate through the cornea and reach the intraocular tissue. As a consequence, multiple administrations of eye drops are required for therapeutic effect (Sultana et al., 2007; Kuno and Fujii, 2011; Gaudana et al., 2010). Administration of eye drops several times in a day result in high and low drug concentration profiles, i.e. high concentration in the toxic range and low concentration in the ineffective range, in addition to a short window of therapeutically effective range (FIG. 10). The major disadvantage of these conventional dosage forms is that they exhibit extremely low bioavailability. The drug contact time and the duration of drug action have been improved by developing gel formulations, ointments, and ocular inserts. Systemically administered medications, in general, have limited ocular penetration and may require high peripheral drug levels with the potential of toxicity. Ocular or periocular injection of medication is traumatic and invasive, is rapidly diluted, and may require repeat procedures for adequate drug levels.

2. Ocular Pharmacokinetics and Drug Transport Across the Ocular Surface

Ocular pharmacokinetic studies are straightforward in vivo experiments analyzing the drug concentrations in the ocular tissues after local or systemic drug administration with or without special delivery systems. Another class of ocular pharmacokinetics includes drug permeability studies in which relationships between physicochemical drug properties and permeability are evaluated (Mannermaa et al., 2006). All these studies are clinically driven, to provide basic information about the ocular pharmacokinetics, without aiming to understand the mechanisms of permeation in the relevant barriers. However, a thorough understanding of the drug molecular diffusion across cornea and conjunctiva is crucial for the development of clinically translatable nano drug delivery systems.

Passive Diffusion of Drug Molecules in the Corneal Epithelium

Topically delivered drug (eye drops or ointments) enters the anterior chamber of the eye by diffusion through the cornea. Approximately a 20 to 60 min lag time is required for the drug to reach the aqueous humor. Lag time is equal to the rate of diffusion of a drug molecule across the cornea. In general, the amount of drug diffusing through the cornea is linearly proportional to its concentration in the tear film. The decline of drug concentration in the tears (hence the concentration of drug penetrating the cornea) follows first order kinetics and the rate depends on the rate of dilution by freshly secreted tears (FIG. 10). In humans, the half-life of a single 20 µl drop of drug solution ranges from 2 to 20 minutes. Hence, only 1 to 5% of the topically applied drug ever reaches the anterior chamber and the rest of the drug will be cleared by the tear film, nasolacrimal drainage system, and systemic absorption from the nasal and gut mucosa (Urtti, 2006).

Diffusion of drug molecules from the tear fluid to cornea is controlled by the residence/contact time of the delivery system on the ocular surface and drug permeability in the cornea. Drug permeability in the cornea is due to passive diffusion or by active transport. Active transport require expression of transporters in the corneal epithelium. Passive diffusion is not dependent on transporter proteins, but it is rather driven by the physical chemical parameters that determine the partitioning and diffusion of the drug molecule in the lipid bilayers of the cell membrane (Mannermaa et al., 2006). Cornea is a fairly tight barrier for drug absorption: permeability of the corneal epithelium is $10^{-7}$-$10^{-5}$ cm/s and the ocular drug bioavailability after topical ocular administration is less than 5% even for small lipophilic molecules (Urtti et al., 1990). The corneal epithelium is a well-recognized barrier to drug absorption (Maurice and Mishima, 1984). The role of corneal epithelium as a barrier and drug depot for the slow release of lipophilic molecules has been demonstrated by Sieg and Robinson (1976). Thus, corneal epithelium can function as a barrier to hydrophilic molecules or as a barrier and depot for small lipophilic molecules. For the smooth permeation of lipophilic drug across the cornea, the log D values should be 2-3 and the permeability decreases with higher log D value (>3) due to strong binding to the lipophilic epithelium.

Active Transport of Drug Molecules in the Corneal Epithelium

Corneal permeability of the drug molecules is sum of the passive diffusion and active transport, and the effect of active transport depends on the extent of passive diffusion. In the corneal epithelium, active transport of hydrophilic drug molecules will be significantly higher than the lipophilic drugs because of the low passive diffusion of hydrophilic molecules. Since the transporter expression is significant on the apical surface of the corneal epithelial cells, active transport of hydrophilic drug molecules across the corneal epithelium will be higher than lipophilic drug molecules. According to the Michaelis-Menten kinetics, active transport of the drug molecules depends on the drug concentration, its affinity to the transporter ($K_m$), and the expression level (i.e. maximum capacity) of the transporter in the membrane ($V_m$) (Mannermaa et al., 2006).

Physicochemical Properties of the Drug

The drug molecules diffuse across the corneal epithelium via transcellular or paracellular pathways. Generally, lipophilic drugs diffuse via transcellular pathway while hydrophilic drugs diffuse by paracellular pathway through the intercellular spaces (Borchardt, 1990). In the case of topically applied drugs, passive diffusion via transcellular or paracellular pathway along the concentration gradient is preferred. The rate of drug permeation in cornea is affected by physicochemical properties of the drug, such as molecular size, shape, charge, degree of ionization, solubility, and lipophilicity (Schoenwald and Huang, 1983; Grass and Robinson, 1988; Liaw and Robinson, 1992; Huang et al., 1989; Rojanasakul et al., 1992; Liaw et al., 1992; Sieg and Robinson, 1977; Maren and Jankowski, 1985; Brechue and Maren, 1993). Lipophilic corneal epithelium is the rate limiting barrier for the diffusion of highly hydrophilic drugs, while partitioning from the corneal epithelium to the hydrophilic stroma is rate limiting for highly hydrophilic drugs that determines corneal permeability. The rate limiting barrier is located at the very surface of the epithelium for moderately lipophilic β-blockers while the whole corneal epithelium is the barrier for hydrophilic compounds (Shih and Lee, 1990). Diffusion of an ionizable drug depends on the chemical equilibrium between the ionized and unionized drug in the tear fluid (Friedrich et al., 1993). The unionized drug molecules diffuse through the lipid membrane more easily than the ionized form. For example, transcorneal penetration of free pilocarpine base was 2-3 times greater than that of the ionized form in vitro (Francouer et al., 1983; Mitra and Mikkelson, 1988).

3. Barriers and Challenges in Ocular Drug Delivery

Delivery of drugs to the anterior segment of the eye in therapeutically effective concentrations is essential for the treatment of infections and inflammations of the cornea and the ocular surface. Cornea and conjunctiva are the major routes of anterior segment drug absorption, however factors, such as impermeability of the corneal epithelium, tear dynamics, momentary residence in the fornix conjunctiva and systemic absorption affect the bioavailability and therapeutic efficacy of a drug. Improving the bioavailability by increasing the drug permeability and absorption in the eye is a great challenge. It is also important to achieve an optimal drug concentration at the target site.

Corneal Barrier

The healthy cornea is a transparent primary lens of the eye. The corneal diameter is about 11.7 mm. The corneal epithelium is the most anterior layer of about 50 µm in thickness. Apical corneal epithelial cells are flat and form tight junctions in the intercellular spaces which act as an effective barrier not only to most microorganisms but also to therapeutic drugs. These tight junctions are located only in the most apical surface cell layers and they provide the diffusional barrier for drug absorption from the tear fluid to the anterior chamber of the eye (Reinsten et al., 1994; Hitzenberger et al., 1994; Grass and Robinson, 1988). Corneal epithelium is the major limiting barrier in the corneal drug absorption and transcorneal drug permeation (Maurice and Mishima, 1984).

Conjunctival Barrier

The conjunctiva is a vascularized mucus membrane that covers the inner surface of the eyelids and covers the anterior part of the sclera. Tight junctions of the superficial conjunctival epithelium are the main barrier for drug penetration across conjunctiva, although the conjunctival epithelium has wider intercellular spaces than the cornea. The conjunctival epithelium also covers a much larger surface area (16-18 cm$^2$) compared to that of the cornea (1 cm$^2$) (Dartt et al., The Biology of the Eye). Because of the relative leakiness of the conjunctival epithelium, rich blood flow, and large surface area, conjunctival uptake of a topically applied drug from the tear fluid is typically an order of magnitude greater than corneal uptake. However, due to the presence of blood capillaries and lymphatics in the conjunctiva, most of the drug will be lost into the systemic circulation, thereby lowering ocular bioavailability. Because of the systemic drug absorption following conjunctival uptake even substantial enhancement of the drug residence times by the ocular insert drug delivery systems in the conjunctival sac may not always result in significant improvements in ocular drug absorption (Newell, 1986; Ahmed et al., 1987). Taken together, cornea and conjunctiva are rate-limiting barriers for the drug absorption in the anterior segment of the eye.

Tear Dynamics

The tear film acts as a dynamic barrier due to a high turnover rate and gel-like mucus layer. The basal tear flow is ~1.2 µl/min (0.5-2.2 µl/min) and reflex stimulation can increase lacrimation up to 300 µl/min (Dartt et al., The Biology of the Eye; Mishima et al., 1966). Topical administration of eye drops stimulate reflex tearing and the drug is quickly washed away by the tear film after application. Gel forming mucus, such as MUC5AC creates a hydrophilic layer that interfaces with the glycocalyx of the ocular surface epithelium and clears cell debris, foreign bodies, and pathogens. Approximately 2-3 µl mucus is secreted daily and acts as a barrier to drug adsorption (Gipson and Argueso, 2003).

Drug Elimination by the Nasolacrimal Drainage System from Tear Fluid

Because the residence tear volume of the eye is generally 7-10 µl, most topically administered solutions are washed away within 15-30 seconds of application (de la Fuente et al., 2010). Topically administered drugs are mainly eliminated from the precorneal tear fluid by reflex tearing and drainage into the nasolacrimal system. The normal commercial eye dropper delivers a drop of ~40 µl. When an eye drop is instilled, the human eye momentarily contains ~30 µl volume, but the instilled solution is rapidly removed by spillage from the conjunctival sac or loss through the puncta to the lacrimal drainage system until the tears return to their normal volume (7 µl) (Lederer and Harold, 1986; Zaki et al., 1986). If the volume of an eye drop is decreased to 5-10 µl and the applied dose is kept constant by increasing the concentration, the ocular bioavailability of the drug can be improved (Chrai et al., 1973). Ocular administration of irritating drugs increases the drug loss from the precorneal area to a further extent due to reflex lacrimation (Meseguer et al., 1993; Craig, 2002).

Systemic Absorption

The goal of ophthalmic drug delivery systems has traditionally been to maximize ocular drug absorption rather than to minimize systemic absorption (Urtti et al., 1990). After instillation of an eye drop, less than 5% of the instilled dose is absorbed into the eye, whereas systemic absorption is often more than 50% of the instilled dose (Urtti and Salminen, 1993; Lee et al., 1993). The main sites for systemic absorption are conjunctiva and nasal mucosa. Systemic absorption of ocularly applied drugs is often nearly complete and could lead to systemic side effects varying from mild to life-threatening events. In the case of ophthalmic drugs that may cause systemic side effects, the drug delivery system must deliver the drug only to the target tissue in a controlled release fashion thus minimizing the systemic absorption of the drug. Clinical administration of a topically applied drug is often limited by its ocular/systemic side effects, such as tearing, blurring of vision, and irritation (Shell, 1984). Since irritation is related to the drug concentration on the ocular surface tissue, a controlled release drug delivery system can minimize irritation and enhance patient compliance.

4. Nano Drug Delivery Strategies

Although the conventional solution and suspension drug formulations are still the most frequently used dosage forms, several new drug delivery systems have been developed to minimize 'peak and valley' effects and maintain drug concentration at an effective level for a prolonged periods of time (Vandervoort and Ludwig, 2007). Recent advances in topical ocular drug delivery have ranged from improvement of eye drops to emulsions, liposomes, lipid nanoparticles, and ocular inserts (Sultana et al., 2011; Kapoor and Chauhan, 2008; Mahmoud et al., 2008; Souto et al., 2010; Li et al., 2008; Seyfoddin et al., 2010; Mack et al., 2009). All these endeavors aim at enhancing drug bioavailability by providing prolonged or sustained delivery to the eye or by facilitating trans-corneal penetration. Nonetheless, very few alternative drug delivery systems have successfully appeared on the market: currently, 95% of products are delivered via the traditional eye-drop bottle (Table 1).

TABLE 1

Representative commercial ocular drug delivery formulations

| Product Name | Active Pharmaceutical Ingredient | Formulation | Company | Indications | Status |
|---|---|---|---|---|---|
| Restasis | Cyclosporin A | Emulsion | Allergan | Severe dry eye disease | Marketed in USA |
| Refresh dry Eye therapy | | Emulsion | Allergan | Dry eye disease | Marketed in USA |
| Durezol | Difluprednate | Emulsion | Alcon | Inflammation | Marketed in USA |
| Cationorm | | Cationic Emulsion | Novagali | Mild dry eye disease | Marketed in Europe |
| Soothe XP Emollient | | Emulsion | Bausch & Lomb | Dry eye disease | Marketed in USA |
| Tear Again | Vitamin A | Liposome | Optima Pharmazeutische | Dry eye disease | Marketed in USA |

TABLE 2

Nanoparticulate drug delivery systems used in ophthalmic research

| Drug | Nanoparticulate System | Result | References |
|---|---|---|---|
| Oligonucleotides | Liposomes | Better control of release rate | [69] |
| Acetazolamide | Liposomes | Produced a marked decrease in IOP | [70] |
| Pilocarpine HCl | Liposomes | Increased mitotic response and ocular bioavailability of the drug | [71] |
| Inulin | Liposomes | Increased ocular concentration of the drug | [72] |
| GCV | Albumin Nanoparticles | Increased antiviral aciivity against human cytomegalovirus (HCMV) infection | [73] |

TABLE 2-continued

Nanoparticulate drug delivery systems used in ophthalmic research

| Drug | Nanoparticulate System | Result | References |
| --- | --- | --- | --- |
| Pilocarpine | Microemulsions | Decreased IOP by 25% | [74] |
| Amikacin | Nanoparticles | Improved delivery of drug to cornea and aqueous humour | [75] |
| Pilocarpine | Poly(butyl)-cyano acrylate Nanopartilces | Enhanced mitotic response and decrease in IOP by 22% | [76] |
| Flurbiprofen | Acrylate Polymer Nanosuspensions | Increased drug levels in aqueous humour | [77] |
| Cyclosporin | Chitosan Nanoparticles | Enhanced delivery to external ocular tissue | [78] |
| Dexamethasone | Microemulsions | Enhanced bioavailability in aqueous humour | [79] |
| Pilocarpine nitrate, Tropicamide | Dendrimers | Prolonged miotic activity | [80] |
| Dexamethasone | HP-β-CD | Enhanced solubility, permeability, and corneal bioavailability | [81, 82] |

5. Nano Drug Delivery Systems

Nano drug delivery systems such as nanoparticles, liposomes, micelles, and dendrimers have been developed with the aim of enhancing ocular drug delivery (Singh et al., 2011; GAudana et al., 2008; Sultana et al., 2007; Kuno and Fujii, 2011; Gaudana et al., 2010). These systems are claimed to provide a prolonged residence time at the ocular surface, minimizing the effect of natural eye clearance systems. It has been argued that, when combined with controlled drug delivery, it should be possible to provide drug therapeutic levels for a prolonged time at the site of action. Nano and microparticles have been developed for systemic drug delivery however, not much progress has been made in the development of nanotechnology based drug delivery systems for treating ocular diseases. Recently, emulsions, micro and nanoparticles have been used in ocular drug delivery with limited success (Diebold and Calonge, 2010; Gershkovich et al., 2008; Choy et al., 2008; Chang et al., 2011). Some of the currently developing nano particulate drug delivery systems are listed in Table 2. Even the nanoparticle suspensions were also rapidly cleared from the eye leading to limited drug efficacy. Micro-/nanoparticle-based delivery systems are easy to prepare, but exhibit limitations, such as: low drug loading, burst drug release kinetics, and clumping of the particles in the fornix and along margins of the eyelids. Also, due to the very short period of drug release (~1-3 h), the therapeutic efficacy is very limited, requiring multiple administrations. To improve the drug retention time in the eye, in situ gel forming systems have been developed (He et al., 2008). A solution containing drug upon instillation as eye drops undergo sol-to-gel phase transition on the eye surface. The in situ formed gels are expected to hold the drug for a longer period of time thus enhancing its bioavailability. However, these in situ forming gels could increase the drug retention times to a few hours. Drug-loaded contact lenses have been developed to improve the drug retention time in the eye (Gulsen and Chuauhan, 2004; Singh et al., 2011). Because contact lenses are in constant contact with the cornea, drug-loaded contact lenses are expected to enhance the drug retention times to more than 30 min. The problem with these systems is that most of the drug diffuses out in an hour or more. As a further advancement, contact lenses loaded with drug filled liposomes, micelles, microemulsions or nanoparticles have been developed (Garhwal eet al., 2012; Peng and Chauhan, 2011; Yanez et al., 2011). These approaches have improved the drug retention times for a few hours, however are not well suited for extended release for a day to a week. Recently, drug-loaded PLGA films were encapsulated inside the contact lenses for the long-term release of econazole (Ciolino et al., 2011). Although, these systems could deliver the drug for up to a month, they are limited by reduced transparency and low oxygen permeability because of the thick PLGA film (Jung and Chauhan, 2012). Also, because of the biodegradable nature of PLGA, these contact lenses cannot be packaged in PBS. In summary, all these systems, although could extend the drug retention times by a few hours, they could not release the drug in a controlled release fashion for extended periods of time. Hence, there is a strong need for the development of programmable drug delivery systems with high drug content and long term drug release attributes.

6. Gaps in the Present Ocular Drug Delivery Systems

Ocular drug delivery can be reduced to the simple goal of getting the right pharmacologic agent at the appropriate therapeutic dose to the target ocular tissue by a method that does not damage healthy tissue. In the treatment of ocular disease, however, this simple goal becomes more challenging because of the highly sensitive ocular tissues and the ocular surface barriers to drug penetration as described above. The challenge is to delicately circumvent these protective ocular surface barriers and deliver the drug to the target site (cornea or conjunctiva) without causing permanent tissue damage. Despite sustained efforts, the development and optimization of new nano drug delivery systems have been very slow.

To improve the therapeutic efficacy of ophthalmic drugs, the drug delivery system must encompass the following attributes: (i) Increase drug residence time on the ocular surface; (ii) Increase the drug absorption; (iii) Improve the bioavailability of the drug; (iv) Minimize systemic absorption of the drug; (v) Improve the local tolerability of the drug delivery system and (vi) Patient compliance. The major challenge to address in drug delivery to the ocular surface is how to localize drug action within the target site and maintain therapeutic drug levels while minimizing systemic effects. Also, the issue of patient compliance must be seriously considered in ocular drug delivery. If a drug must be given every hour for a week, for example, to reach therapeutic tissue concentrations when treating a chronic disease, it is very unlikely to be given consistently, if at all.

Embodiments of the present disclosure satisfy a long-felt need in the art to provide a controlled release ocular drug delivery system that can release the drug in therapeutically effective concentrations for longer duration of time (for example, from a day to a week).

BRIEF SUMMARY OF THE DISCLOSURE

This disclosure relates to providing localized delivery of therapeutics in a controlled manner. The embodiments of the present disclosure are particularly applicable to continuous administration of therapeutics to the eye for treating various illnesses or conditions such as: dry eye disease, ocular infections (bacteria, fungal, and viral), eye injury, wound healing, nerve regeneration after corneal injury, LASIK, or corneal transplant, corneal ulcers, preventing/treating corneal vascularization and angiogenesis, corneal cystinosis, glaucoma, diabetic retinopathy, macular degeneration, ocular surface, corneal, or intraocular inflammation, etc. The embodiments of the present disclosure can also be used in the long term local and/or systemic delivery of immunosuppressant and anti-inflammatory drugs for organ transplanted patients, such as corneal transplant patients.

Embodiments of the present disclosure generally relate to controlled release of therapeutics in an individual, including delivery of therapeutics locally through a dissolvable substrate. In specific embodiments, the dissolvable substrate is a matrix, and an example of a matrix is a hydrogel matrix, such as a mucoadhesive polymeric hydrogel matrix.

Embodiments of the disclosure encompass a controlled-release nanowafer drug delivery system that can be readily instilled locally on or in an individual. In specific embodiments, the nanowafer drug delivery system is utilized in the eye, and in particular embodiments the system is utilized on the cornea or conjunctiva, for example by the patient's fingertip or with an applicator without any clinical procedure.

According to one aspect, there is provided a device for delivering therapeutics to the eye comprising: a hydrogel matrix comprising at least one biocompatible material; and a plurality of reservoirs disposed in the hydrogel matrix; wherein at least a portion of a surface of the hydrogel matrix containing an open end of the plurality of reservoirs is configured to contact a surface of a user's eye and dissolves upon contact with the surface of the user's eye. In one embodiment, the dissolution of the surface portion of hydrogel matrix occurs at a predetermined rate. In another embodiment, the predetermined rate of dissolution is based at least on the biocompatible material. The device may be of any suitable shape, including at least circular, elliptical, rectangular, square, oval, and so forth. The reservoirs may be of any suitable shape, including at least circular, elliptical, rectangular, square, oval, and so forth. In specific embodiments, a device may have reservoirs of different shapes, such as from two, three, or more different shapes. In another embodiment, two or more drugs will be loaded in the nanowafer independently or as a mixture or suspension.

In certain embodiments, the biocompatible material comprises at least one of the following: dextran, hyaluronan, hyaluronic acid, polyvinyl alcohol, carboxy methyl cellulose, hydroxypropyl cellulose, polyvinylpyrrolidone, polyvinyl alcohol (PVA), Polylactide-co-glycolide (PLGA), polyhydroxy ethyl methacrylate (PolyHEMA), Polyhydroxy ethylacrylate, gelatin materials, collagen materials, and any combination thereof. In another embodiment, the device is configured to release a portion of at least one substance contained in the reservoirs upon contact with the surface of the user's eye. In another embodiment, the device is configured to release the substance in the reservoirs for at least 1 to 30 days. In yet another embodiment, the dissolution of the surface portion of the hydrogel matrix contacting the surface of the user's eye releases a portion of the substance from the reservoirs.

In certain other embodiments, the hydrogel matrix is configured to completely dissolve after a predetermined period of time. In one embodiment, at least one reservoir has a depth of about 500 nm. In another embodiment, the hydrogel matrix has a surface area of about 1 square mm to 150 square mm, preferably between about 1 square mm and 100 square mm, or between about 1 square mm and about 50 square mm, or between about 1 square mm and about 25 square mm, or between about 5 square mm and about 15 square mm.

According to another aspect, there is provided a method for fabricating a therapeutics dispensing device comprising the steps of: forming a template comprising a base component and a plurality of posts attached to a surface of the base component; providing a biocompatible material layer with a thickness greater than the length of the posts adjacent said base portion; removing said biocompatible material layer from said template to form a hydrogel matrix with a plurality of reservoirs corresponding to the posts; and injecting a therapeutic into at least one reservoir.

In one embodiment, there is a method of treating an ocular medical condition in an individual, comprising the step of applying at least one device of the disclosure to an eye of the individual, wherein at least one of the plurality of reservoirs comprises at least one therapeutic composition. The ocular medical condition may be selected from the group consisting of a corneal disease, corneal inflammation, corneal injury, dry eye disease, ocular infections (bacterial, fungal, or herpetic keratitis), eye injury, ocular burn injury (chemical, thermal), wound healing, nerve regeneration after corneal injury, LASIK, or corneal transplant, corneal ulcers, prevention/treatment of corneal neovascularization and angiogenesis, corneal cystinosis, glaucoma, diabetic retinopathy, and macular degeneration. In at least some cases, the ocular medical condition is an ocular surface inflammation, infection, or both. The ocular medical condition may be cystinosis.

In particular embodiments, at least one device of the disclosure is applied on the cornea, on the conjunctiva, or in the fornix. In at least one aspect, the therapeutic composition comprises a drug, and the drug may be of any kind, including at least riboflavin, doxycycline, dexamethasone, tacrolimus, topiramate, etifoxine, vinaxanthone, and neotrofin, sorafenib, sunitinib, cyclosporin A, avastin, ciprofloxacin, levofloxacin, erythromycin, azithromycin, acyclovir, valacyclovir, ganciclovir, cysteamine, brucellamine, tiopronin, anti-IFNγ, limbal stem cells, or a combination thereof. In certain cases, such as when an individual has cystinosis, the drug may be cysteamine, brucellamine, tiopronin, polythiols, thiopolymers (thiomers), or a combination thereof.

In one embodiment, there is a method of delivering at least one therapeutic composition to an individual for nerve regeneration in at least one eye, comprising the step of applying at least one device of the disclosure to the individual, wherein at least one of the plurality of reservoirs comprises the therapeutic composition. In certain embodiments, an individual is in need of nerve regeneration, such as after LASIK surgery or after corneal transplant or corneal injury.

The foregoing has outlined rather broadly the features and technical advantages of the present disclosure so that the detailed description of this disclosures that follows may be better understood. It is understood that this disclosure can be used in other fields. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures, substances, and processes for carrying out the same purposes of the present disclosure. It should also be realized by those skilled in the art that such equivalent constructions, substances, methods, processes, or apparatus do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

Features and advantages of the present invention will become appreciated as the same become better understood with reference to the specification, claims, and appended drawings wherein:

FIG. 22 shows a drug escalation study, demonstrating the optimal drug concentration in the nanowawafer at 150 ng/wafer with no toxicity.

Figure 1:
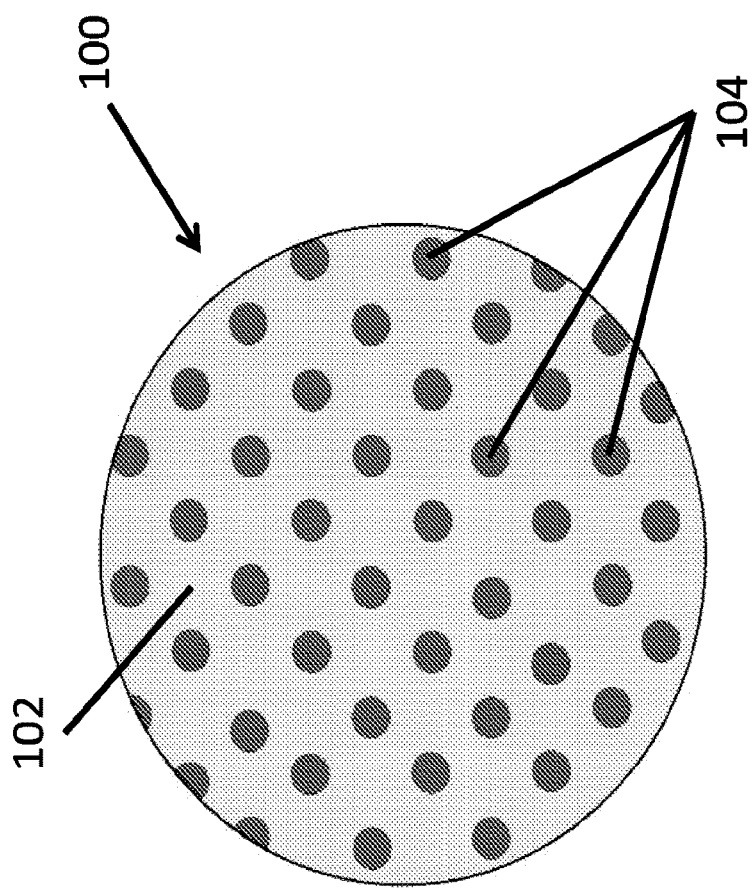
FIG. 1 is an illustration of one embodiment of a therapeutics dispensing device of the present disclosure.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE DISCLOSURE

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a device that "comprises," "has," "includes" or "contains" one or more elements possesses those one or more elements, but is not limited to possessing only those elements.

Embodiments of the present disclosure provide compositions and/or methods for treating a localized medical condition with a controlled release drug delivery substrate. The localization is in the eye or a part thereof, and any suitable ocular medical condition may be treated. Embodiments also include methods of making the substrates and the substrates themselves, which may also be referred to as devices.

In specific cases, the ocular medical condition concerns the cornea. Corneal avascularity promotes corneal transparency and thus clarity of vision (Cursiefen, 2007; Azar, 2006). However, damage to the ocular surface due to corneal infection, trauma, chemical injury, herpes virus infection, and rejection of corneal transplants can induce corneal neovascularization, inhibit re-epithelialization and nerve regeneration, thereby compromising vision (DeStafeno and Kim, 2007). Injuries to the eye often damage the epithelium covering the cornea, conjunctiva, and eyelid margins and in more severe cases destroy the stem cells that renew these epithelia. In many cases, the supporting stromal cells and matrix are damaged and chronic inflammation is induced. The influx of inflammatory cells (monocytes/macrophages, neutrophils), activation of corneal cells (mainly keratinocytes), and epithelial cells, and subsequent stromal neovascularization frequently lead to clouding of the cornea and reduced vision. These events can cause inhibition of re-epithelialization and nerve regeneration in the cornea, and tear desiccation/dry eye. Presently available treatment modalities for ocular injury and inflammation require frequent administration and often produce minimal therapeutic effect. Hence, there is an unmet need for the development of broadly applicable nanowafer drug delivery systems with long term drug release attributes that can release the drug in therapeutically effective concentrations for extended periods of time.

The nanowafer drug delivery system upon placement in the eye will release the drug for a longer duration of time (for example, one day to one month) in a controlled release fashion, thus enhancing the drug efficacy and improving patient compliance. Because the drug molecules slowly diffuse from the polymer matrix of the nanowafer, they are protected from degradation and rapid release. Since all the components of the nanowafer: PVA (polyvinyl alcohol), PLGA (poly(lactic-co-glycolic acid)), and most of the proposed drugs are FDA approved, it can be readily translated to the clinic for treating dry eye disease. Nanowafers may be fabricated with polymers that are currently used in commercial artificial tears and therefore nanowafer fabricated with these polymers may function both as a drug delivery system and also as lubricant. Furthermore, the nanowafer drug delivery system developed for treating corneal/ocular surface diseases can find application in treating dry eye disease, ocular infections (bacaterial, fungal, and herpetic keratitis), eye injury, ocular burn injury (chemical, thermal), wound healing, nerve regeneration after corneal injury, LASIK, or corneal transplant, corneal ulcers, prevention/treatment of corneal vascularization and angiogenesis, corneal cystinosis, glaucoma, diabetic retinopathy, macular degeneration, ocular surface corneal and intraocular inflammation, etc.

Furthermore, the nanowafer drug delivery system can provide mechanical barrier to protect the injured eye from desiccation and/or microbial and/or inflammatory cell infiltration, in addition to controlled drug delivery, thus facilitating the emergency management of blinding eye injuries. Embodiments provide a controlled-release nanowafer drug delivery system that can release the drug from hours to a day to at least a week, thus enhancing the drug efficacy, minimizing the systemic loss of drug, and improving patient compliance.

1. Controlled Release Drug Delivery Nanowafer for Treating Corneal Diseases

By integrating the nanofabrication technologies and controlled release drug delivery technology, a nanopatterned hydrogel wafer (nanowafer) drug delivery system is provided that can surmount the limitations of the presently available ocular drug delivery systems. The nanowafer drug delivery system can release the drug in a therapeutically effective concentration for longer duration of time, i.e., from a day to a week (FIG. 12A). The nanowafer may be a tiny disc (2-4 mm diameter) that can be applied on the ocular surface, such as with a fingertip (FIG. 12D), and can withstand constant blinking without being displaced. Because the open faces of the nanoreservoirs are in close contact with the cornea, in certain embodiments, the drug molecules can diffuse from the nanowafer into the corneal tissue (FIG. 12B-F). The nanowafer can release the drug in a tightly controlled fashion to maintain the drug concentration in a therapeutically effective range. At the end of the stipulated period of drug release, the nanowafer will dissolve and fade away, in particular aspects.

Nanowafer Design

The nanowafers may be fabricated via hydrogel template strategy (Acharya et al., 2011; Acharya, Shin, Vedentham, et al., 2010; Acharya, Shin, McDermott, et al., 2010). Nanowafers may be fabricated by choosing polymers possessing the following attributes, for example: water-solubility, biocompatibility, transparency of the materials with refractive indices close to water, and mucoadhesive property so as to readily adhere and conform to the curvature of the eye. Nanowafers with reservoirs of a series of dimensions (200 nm to 3 μm) may be designed and fabricated by e-beam lithography and photolithography. The drug reservoir dimensions may define the drug content and release kinetics, in certain embodiments, thus imbuing the nanowafer with programmable attributes. In addition, the nanowafer drug delivery system controls the drug release to maximize the therapeutic efficiency and minimize the toxic side effects (FIG. 12E), in at least certain aspects. During the course of the drug release, the nanowafer slowly dissolves and fades away, in certain embodiments.

The nanowafer upon placement in the eye releases the drug for a longer duration of time (at least one day to one month) in a controlled release fashion, thus enhancing the drug efficacy and improving the patient compliance. Because the drug molecules slowly diffuse from the polymer matrix of the nanowafer, they are protected from degradation and rapid release. Because all of the components of the nanowafer (drugs and polymers) are FDA approved, it can be readily translated to the clinic for treating dry eye disease. Nanowafers may be fabricated with polymers that are currently used in commercial artificial tears and, therefore, nanowafers fabricated with these polymers may function both as a drug delivery system and also as lubricant. Furthermore, the nanowafer drug delivery system developed for dry eye and corneal inflammation is useful in treating other corneal diseases, including sight-threatening injuries.

In particular embodiments, the nanowafer enables the development of a biodegradable (dissolvable) nanowafer with high drug content with long term drug release attributes. The most significant advantage of this approach is that the nanowafers can be readily fabricated via the hydrogel template strategy. The polymer matrix of the nanowafer protects the drug molecules from oxidative degradation. The drug molecules slowly diffuse out from the nanowafer to the surrounding tissue, thus enabling the drug availability for a longer duration of time. The desired drug release profiles can be obtained by fabricating nanowafers containing drug reservoirs of different dimensions. The open faces of the drug reservoirs will be in constant contact with the conjunctiva and the released drug molecules slowly enter the conjunctival tissue, thus enhancing the constant bioavailability. The nanowafer material slowly dissolves during the course of drug release and eventually will disappear. The nanowafer material will be selected such that upon slow dissolution, it will function as a lubricant thus providing necessary relief and comfort, in at least some embodiments. The new programmable nanowafer drug delivery systems can provide simple, more efficacious and controlled release nano therapeutic systems for clinical use. The nanowafer drug delivery system, because of its simple fabrication method, long-term drug release ability, mucoadhesive nature, and broad applicability, is unique and provides a new mode of ocular drug delivery. The development of broadly applicable nanowafer drug delivery systems fulfills hitherto unmet need for a long-term release drug delivery system with high drug content that can release the drug in therapeutically effective concentrations for extended periods of time. Currently, there is no such device available and development of nanowafer drug delivery system is a major advancement in the field of ocular drug delivery.

Development of a long-term release nanowafer drug delivery system that can be readily instilled on the cornea, conjunctiva, or in the fornix of the eye (for example) by the individual's fingertip without any clinical procedure is not only very convenient, but also most desirable for treating at least corneal diseases, chronic dry eye, corneal inflammation and injuries, and neovascularization, glaucoma, and other ocular surface inflammations/infections.

2. Fabrication of Nanowafers Via Hydrogel Template Strategy

Figure 3:
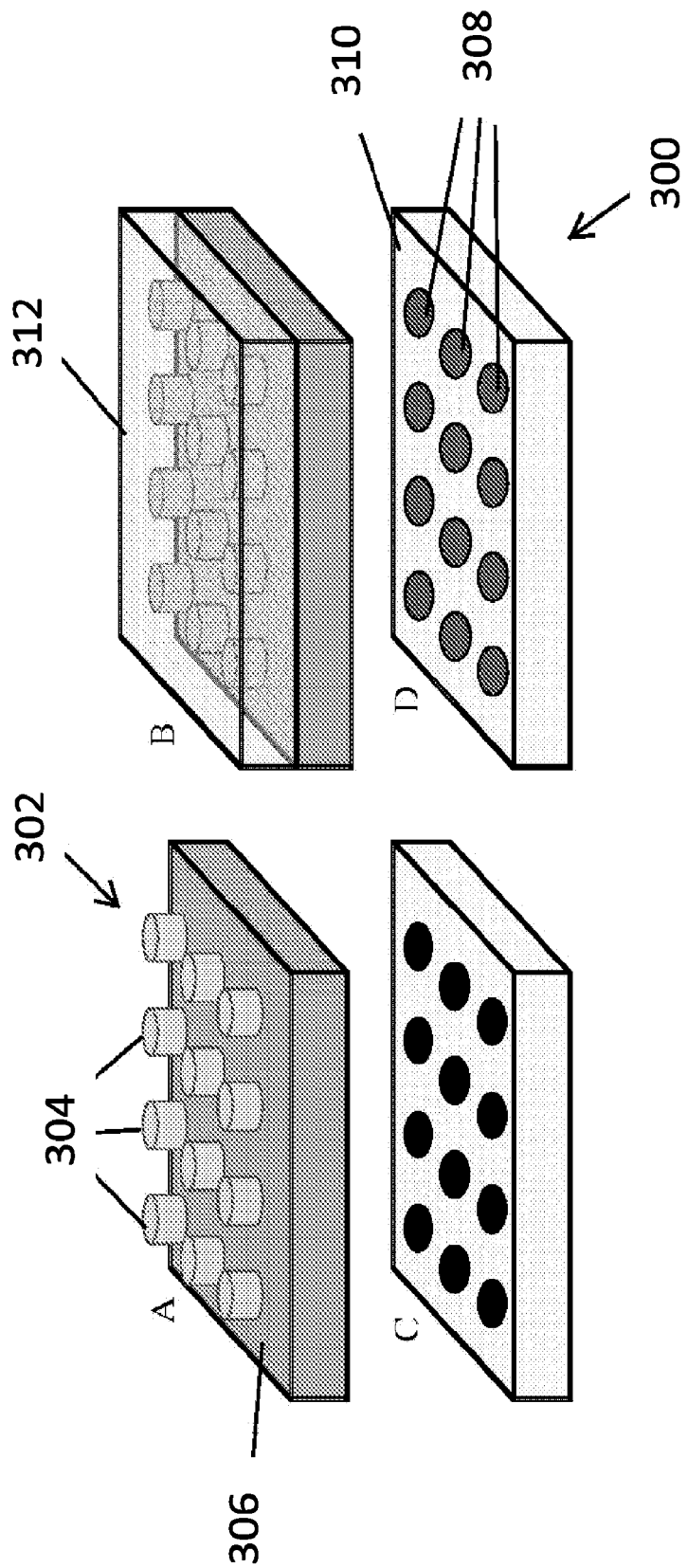
FIGS. 3A-3D are schematic illustrations of one embodiment to fabricate an exemplary therapeutics dispensing device according to the aspects of the present disclosure.
Figure 13:
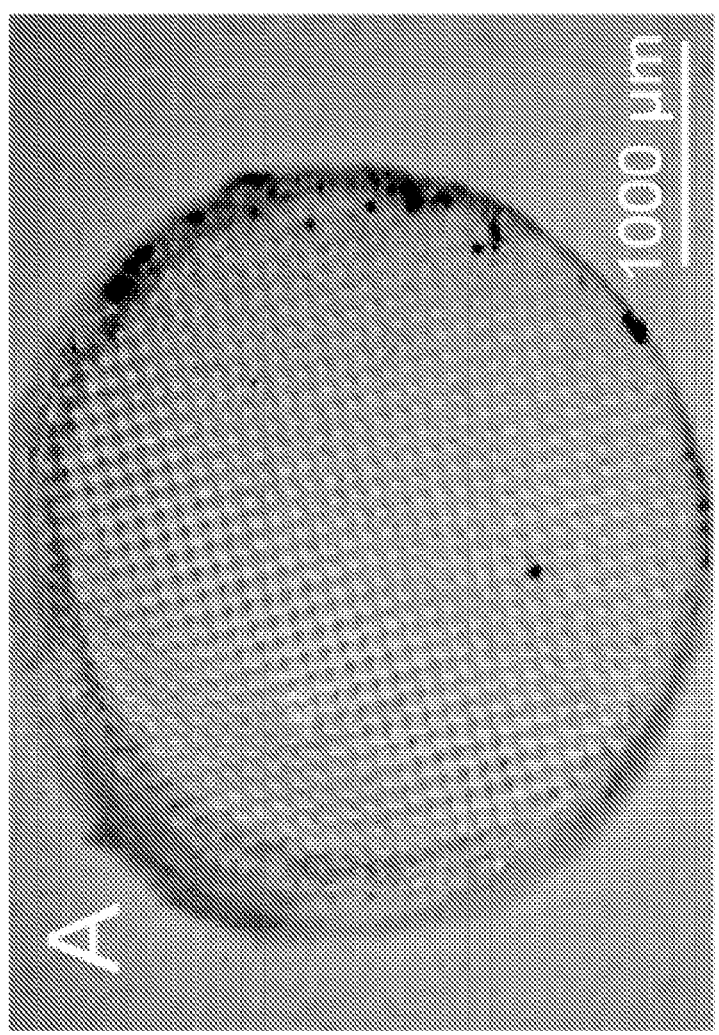
FIG. 13 shows nanowafer fabrication via hydrogel template strategy. Unfilled nanowafer containing empty wells (500 nm diameter and depth, respectively: (A) bright filed image; (B&C) atomic force micrograph; nanowafer filled with fluorescent drug doxycycline: (D) bright filled image; and (E) fluorescence image.
Figure 13:
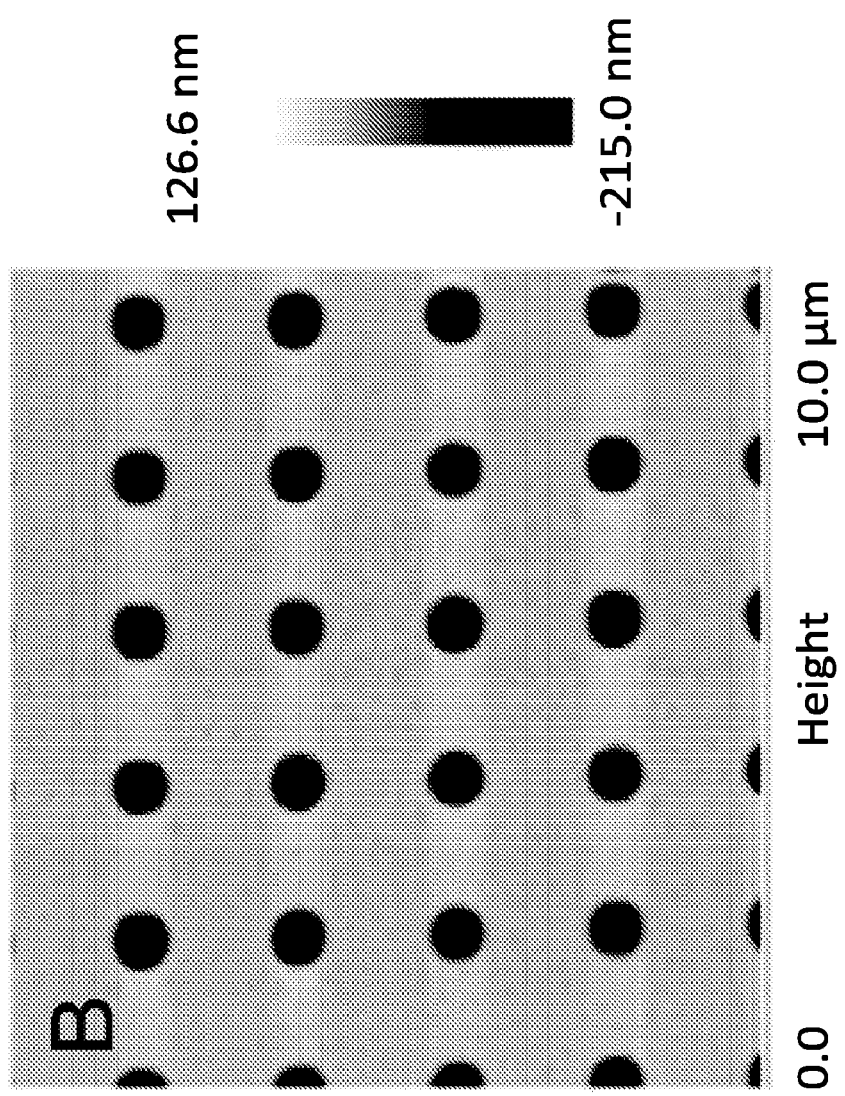
Figure 13:
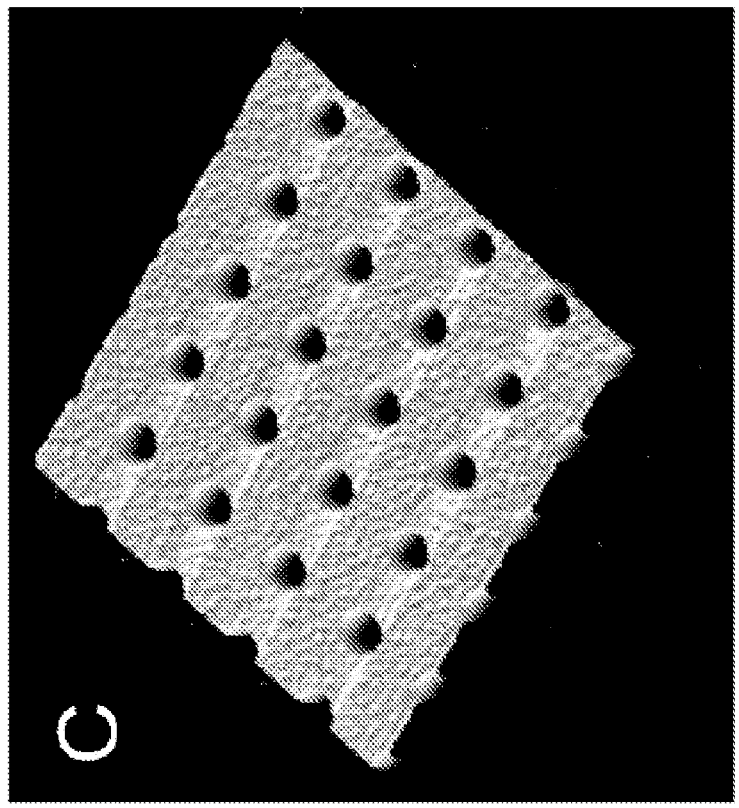
Figure 13:
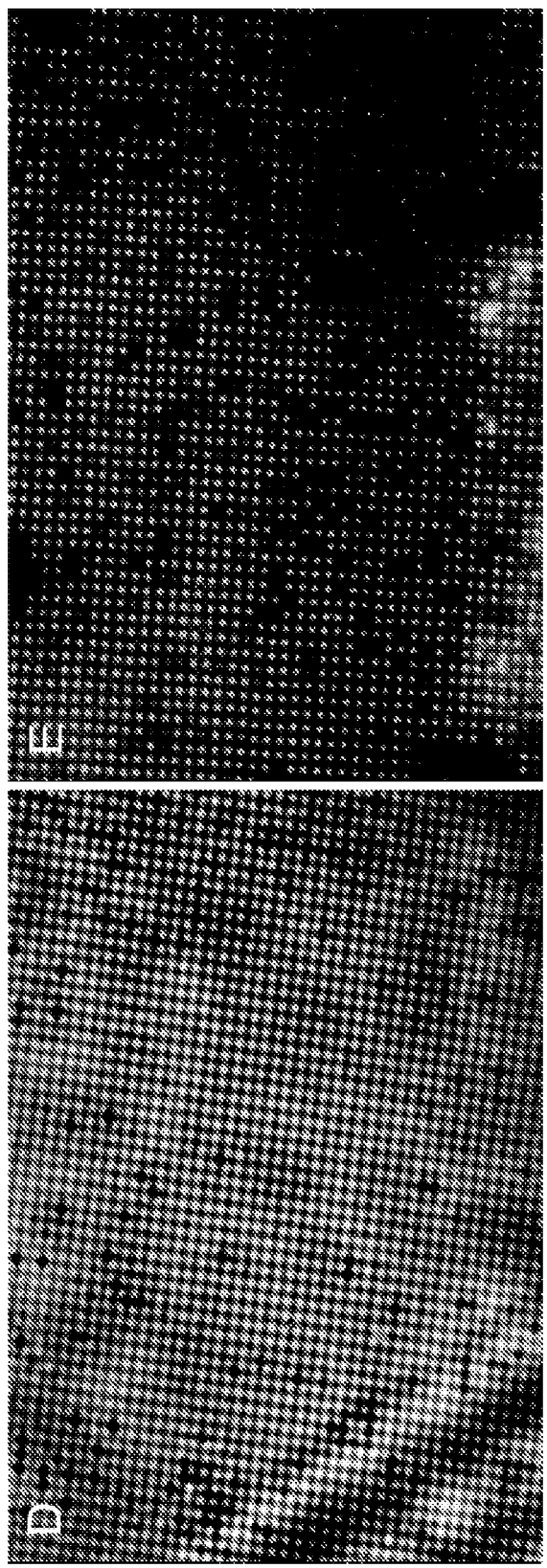

Phase reversible hydrogels have been used in tissue engineering, drug delivery, and as biosensors (Park et al., 1993; Peppas et al., 2006; He et al., 2008). Recently, the hydrogel template strategy has been developed for the fabrication of nanopatterned hydrogel wafers that can function as controlled release drug delivery systems (Acharya et al., 2011; Acharya, Shin, Vedentham, et al., 2010; Acharya, Shin, McDermott, et al., 2010). An aspect of the hydrogel template strategy is presented in FIG. 3. In some cases, the first step is the nanofabrication of arrays of vertical posts on a silicon wafer (FIG. 3A). The silicon wafers thus fabricated were used for the imprinting of hydrogel nanowafers. On top of the silicon wafer, a hydrogel forming polymer solution was poured and heated for 30 min at 70° C. (FIG. 3B). Once the polymer layer is solidified, it is peeled off from the silicon wafer (FIG. 3C). The nanoreservoirs are filled with drug-PLGA matrix, for example using an ultrasonic atomizing nozzle or by microinjection (FIG. 3D). Various natural and synthetic hydrogel forming materials were examined and PVA was selected as a useful system for the fabrication of nanopatterned wafers (nanowafer). PVA is an FDA approved material and has been used as a lubricant in eye drops. Silicon wafer having 500 nm features were fabricated by e-beam lithography. The nanowafer is a tiny disc (2-5 mm diameter) that can be applied on the cornea, conjunctiva or under the lower eye lid with a fingertip (FIG. 13A-C), in specific embodiments. The nanoreservoirs of the wafer were loaded with doxycycline-PLGA matrix (FIGS. 13D & 13E). The drug molecules slowly diffuse out thus enabling a constant availability of the drug in the eye.

3. Evaluation of In Vitro Drug Release Profiles

Figure 14:
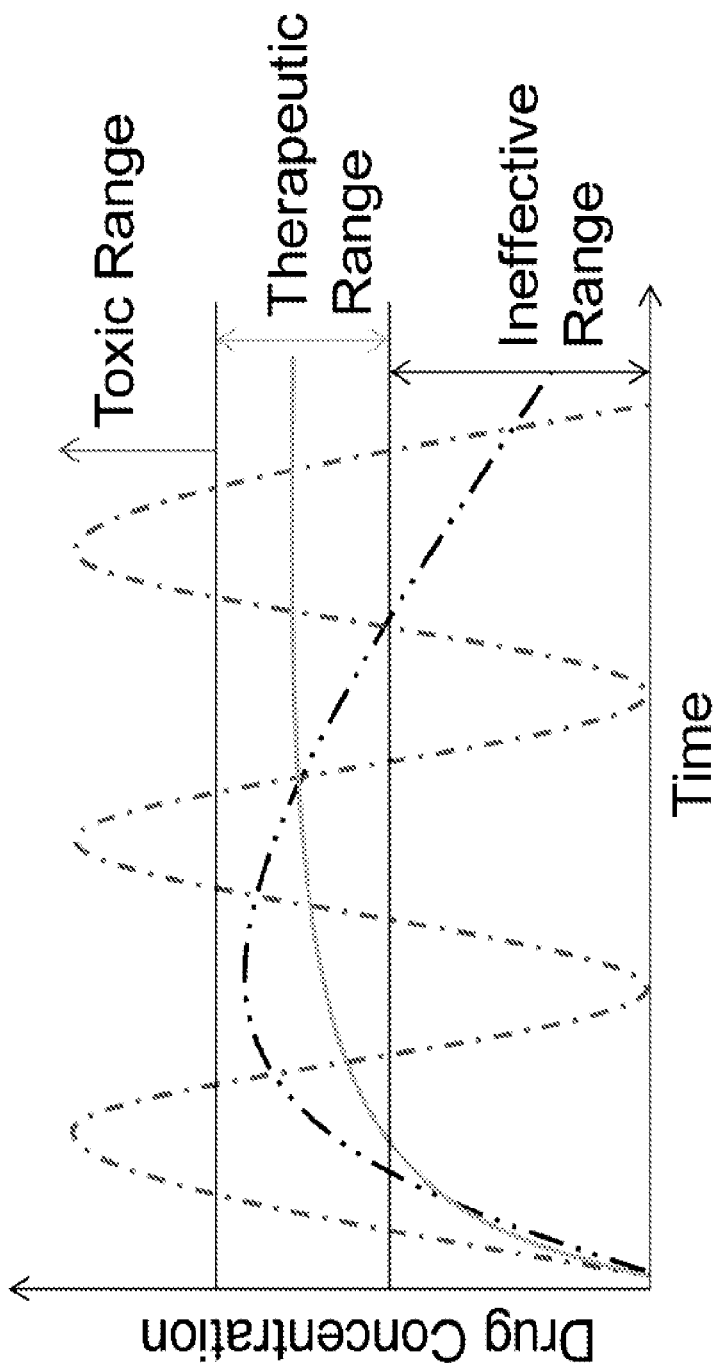
FIG. 14 illustrates drug release profiles of different drug delivery systems: peak and valley drug availability profile of eye drop formulation (short dash and dots); sustained drug release profile (long dashes and dots); and controlled drug release profile (solid line).

Drug release from the nanowafer can be programmed by selecting the right drug reservoir dimension and drug loading concentration, in at least certain cases. Smaller reservoir dimensions enable a slow diffusion of drug molecules and a slow release, while drug molecules diffuse rapidly from larger reservoirs. Similarly, a low drug loading concentration results in slower release while a higher concentration leads to rapid release. The drug release from the nanowafer can be classified into 2 categories based on 3 parameters: the magnitude of initial burst release, the extent of drug release, and the drug release kinetics followed by the initial burst release (FIG. 14). Presently available eye drop formulations will result in peak and valley drug concentrations on the ocular surface and only 1-5% of the drug will be absorbed into the cornea. In the case of sustained drug release nanoparticles, the drug concentration is in the therapeutic range for a short period of time followed by slow decline into the ineffective range. In the case of controlled drug release nanowafer, the drug concentration quickly reaches a therapeutic window and continues to remain there for a predefined period of time, such as from a day to a week, as required. Thus the drug release from controlled drug release nanowafer can programmed to have prolonged drug efficacy to suit patient's requirements.

Figure 12:
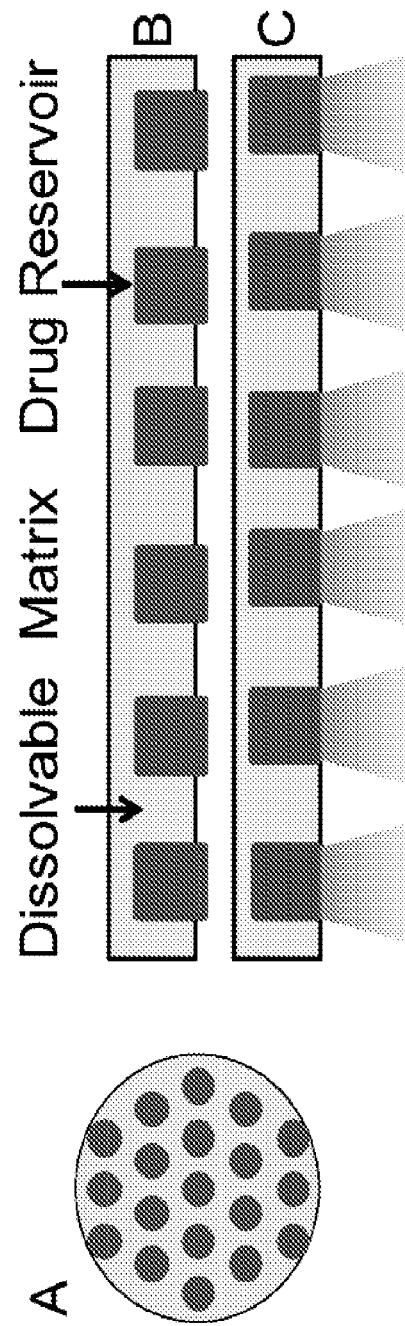
FIG. 12 shows controlled release nanowafer drug delivery system for corneal drug delivery. Schematic depicting: (A) nanowafer; (B) Cross section nanowafer; (C) drug release from the open faces of the nano drug reservoirs that are in direct contact with the cornea; (D) nanowafer instilled on the cornea; (E) cross section of the eye with a nanowafer instilled on the cornea; (F) diffusion of drug molecules from the nanowafer into the cornea; and (G) expected controlled drug release profile of the nanowafer.
Figure 12:
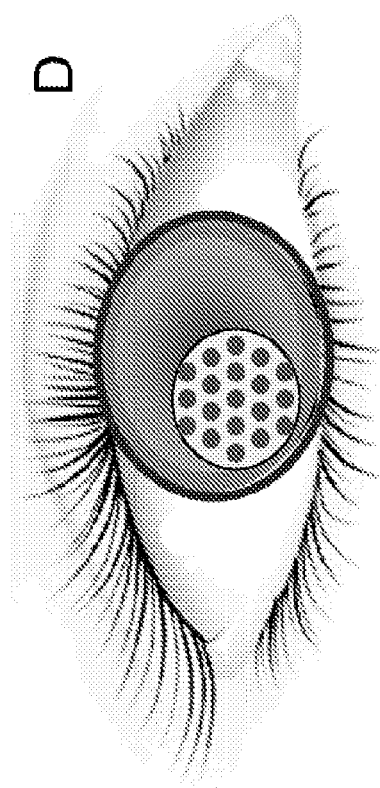
Figure 12:
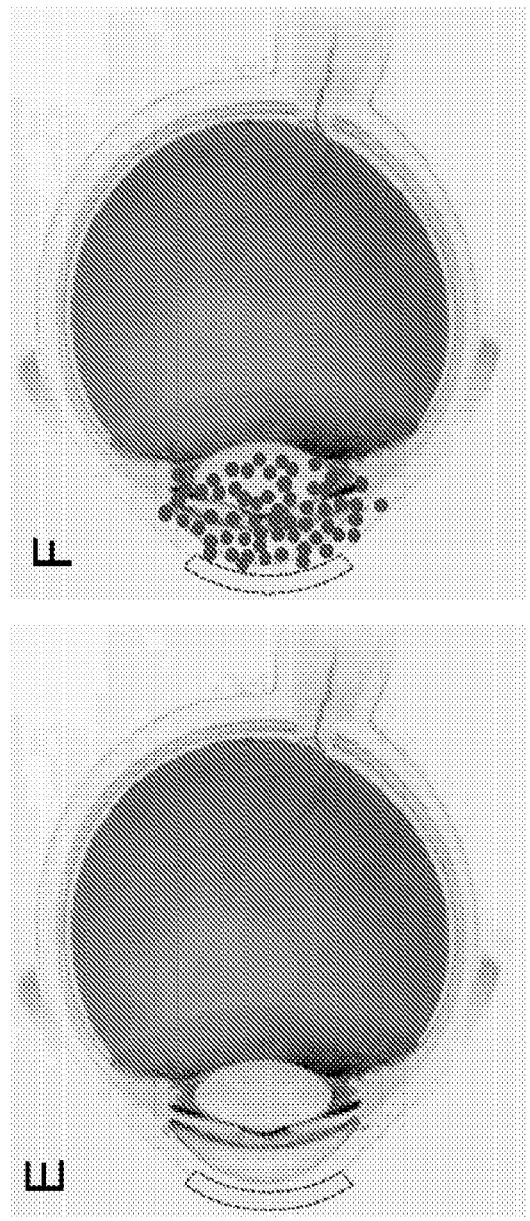
Figure 12:
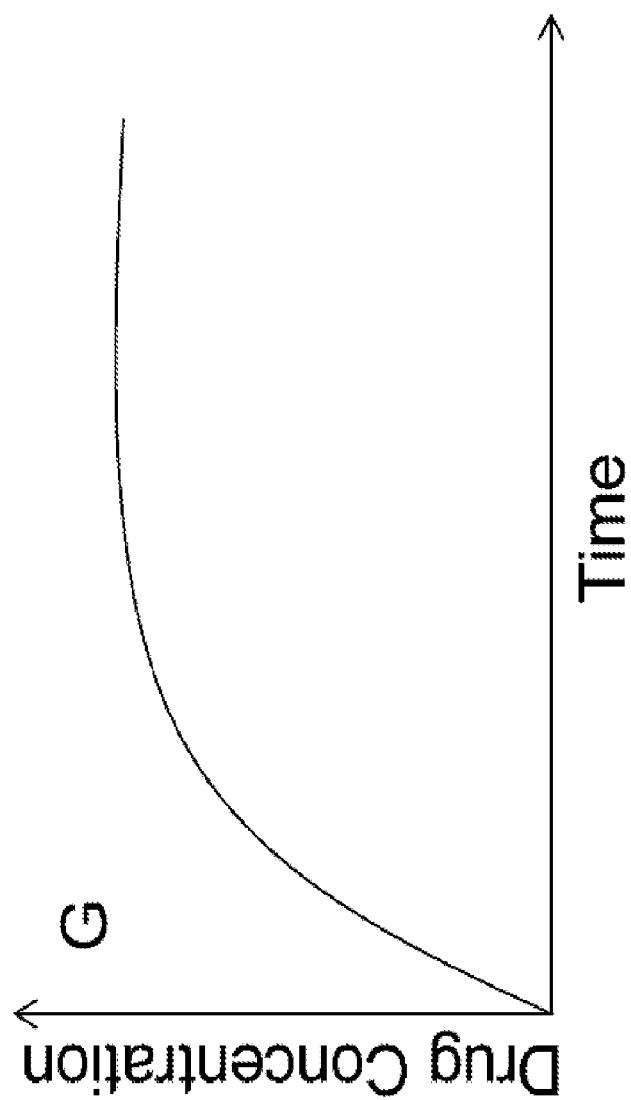
Figure 15:
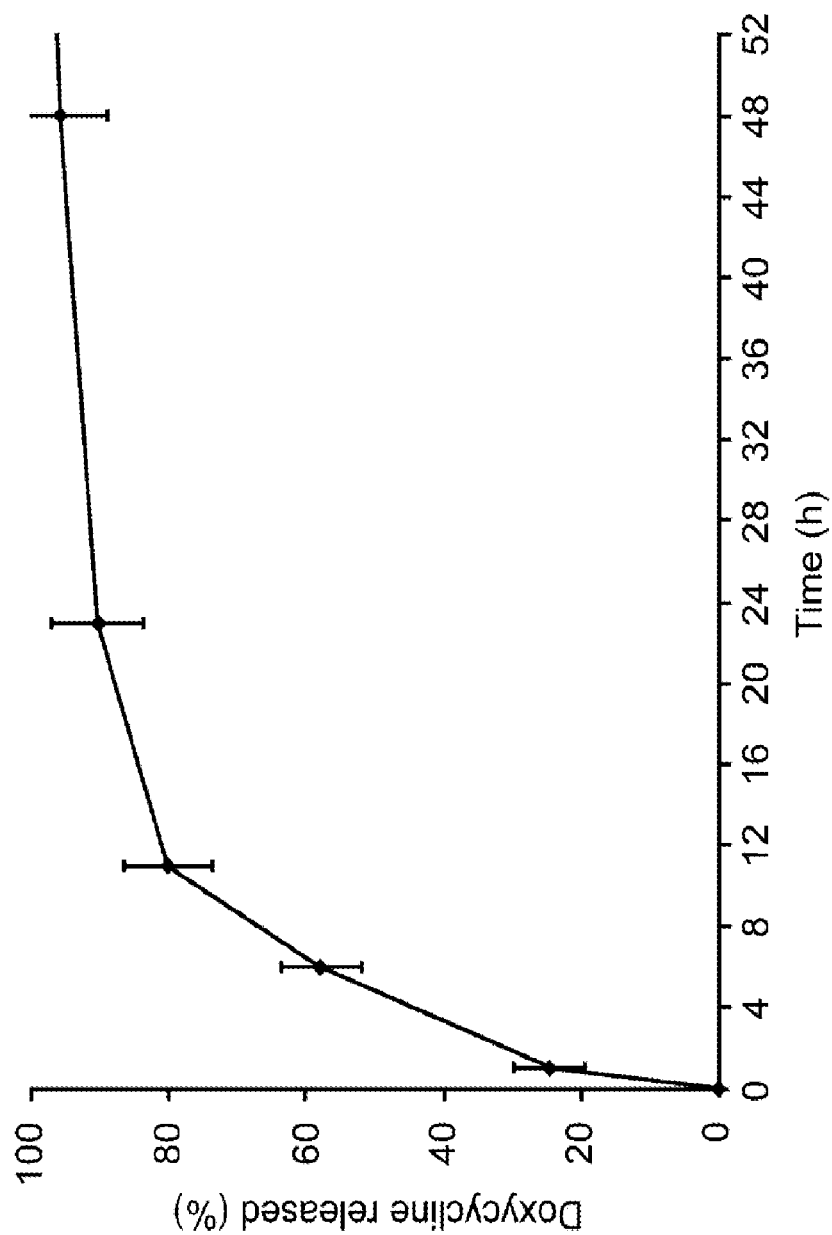
FIG. 15 shows an in vitro drug release profile of doxycycline from the nanowafer.

The drug release profiles of dexamethasone, doxycycline, riboflavin, topiramate, tacrolimus, sorafenib, sunitinib, avastin, and anti-IFNγ (as examples only) are examined as a function of the formulation parameters, such as the drug loading (i.e., the percentage of the total amount of the drug), properties of the active drug (molecular weight and hydrophobicity). In addition to the controlled drug release kinetics, the nanowafer also enables the drug release only from the surface in direct contact with the eye (FIG. 12). As a result, the released drug is in constant contact with the conjunctiva, thus enhancing the efficacy of the drug. In an initial study, nanowafers having an array of 500 nm diameter reservoirs were fabricated and filled with the exemplary drug doxycycline by microinjection. The drug release from doxycycline loaded nanowafer was studied by UV spectrophotometric analysis. As can be seen from FIG. 15, the doxycycline release after 4 hours was ~50% and quickly reaches the therapeutically effective concentration range followed by almost zero-order release for up to 2 days. One can optimize the fabrication and drug loading parameters for the nanowafer to accomplish dexamethasone release for a week, for example, in certain embodiments.

Figure 16:
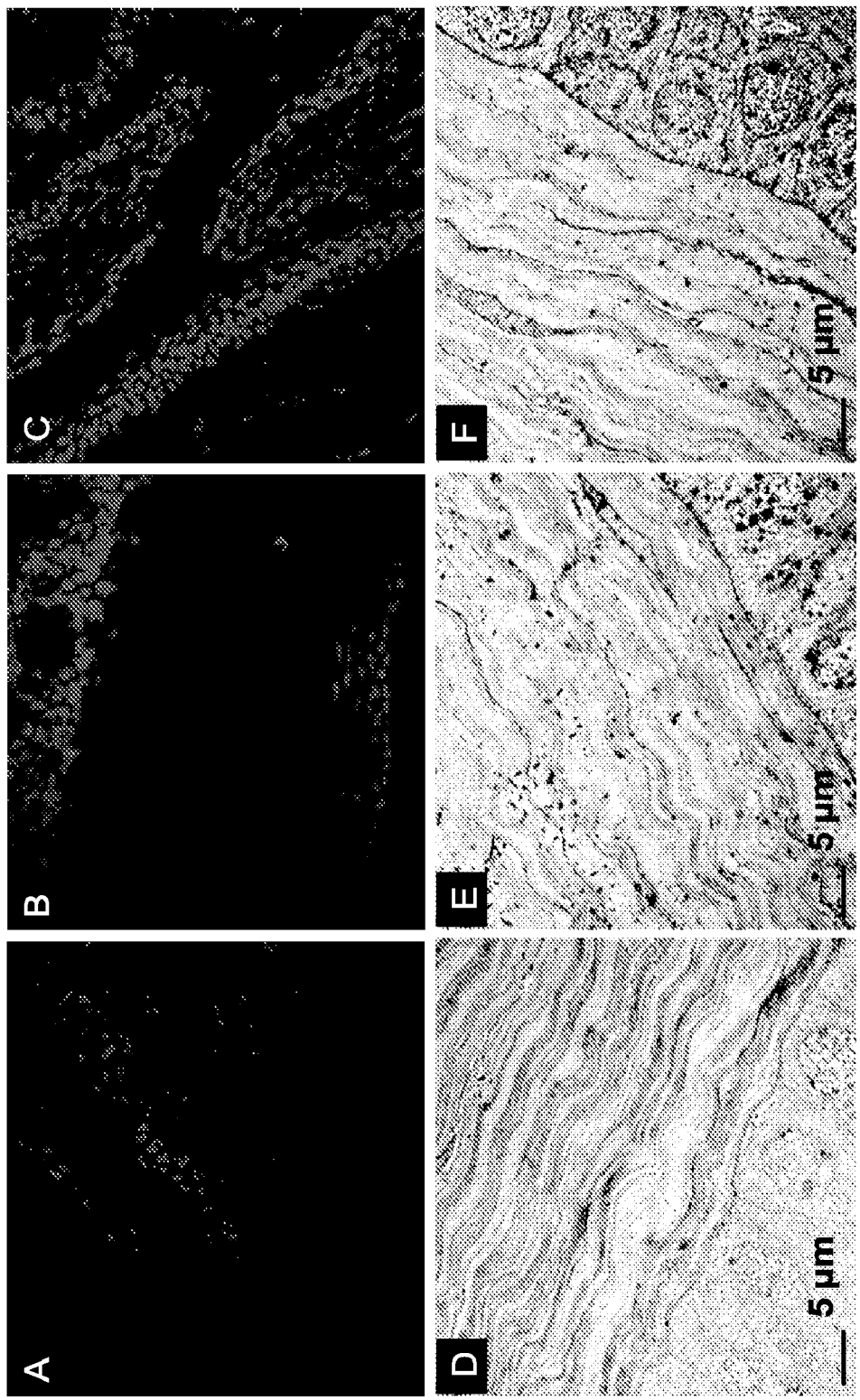
FIG. 16 shows diffusion of nanoparticles from the nanowafer into the cornea. Laser confocal fluorescence images of red fluorescent nanosphers (60 nm) diffused in the cornea: (A) control (without the nanowafer); (B) after 2 days; (C) after 5 days; and transmission electron micrographs (TEM) demonstrating the diffusion of gold nanospheres (60 nm) in the cornea: (D) control (without the nanowafer); (E) after 2 days; and (F) after 5 days.
Figure 17:
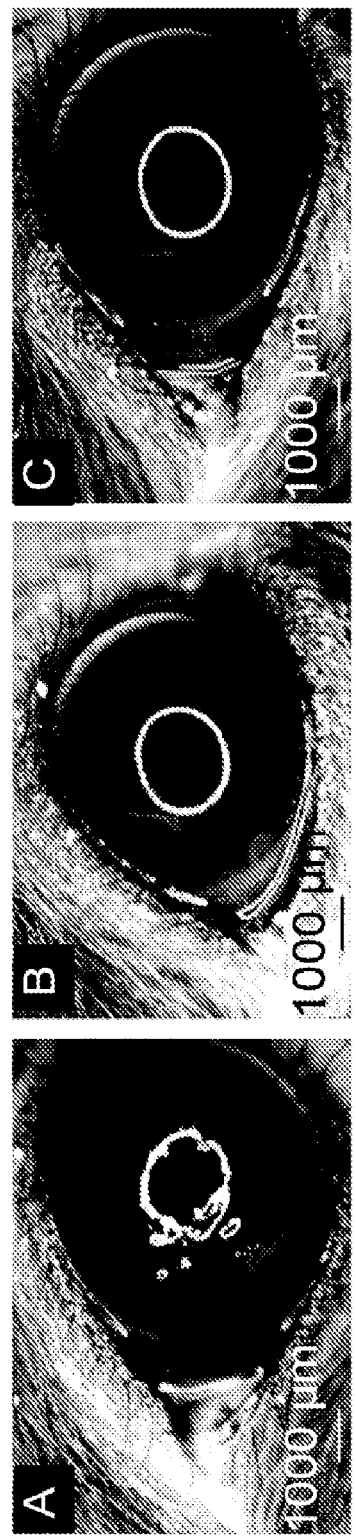
FIG. 17 provides evaluation of corneal smoothness by the reflection of a ring of white light in dry eye induced mice instilled with nanowafers in the fornix: (A) blank PVA nanowafer (control); (B) doxycycline loaded nanowafer; and (C) dexamethasone loaded nanowafer. Scale bar 1000 µm.
Figure 18:
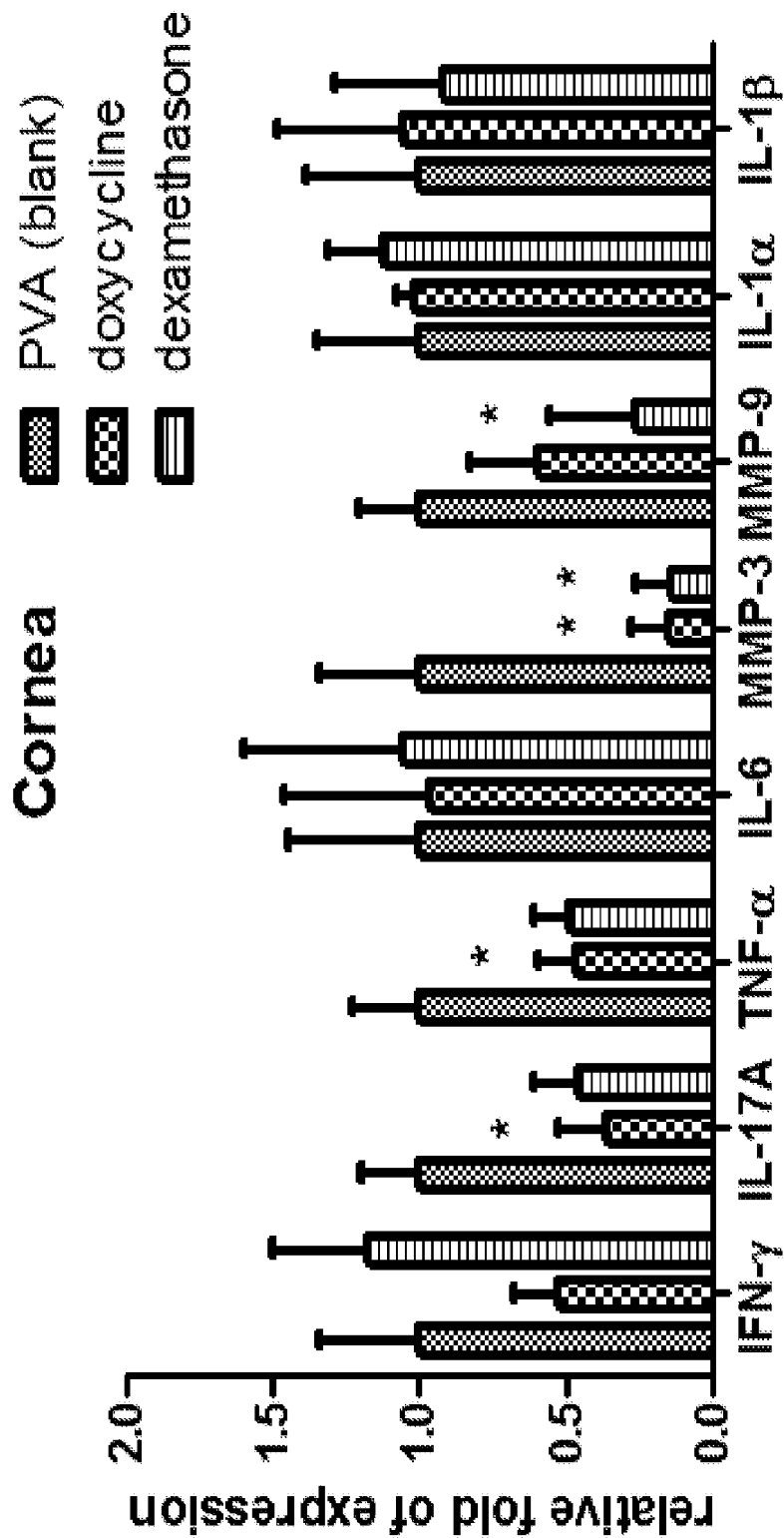
FIG. 18 demonstrates gene expression analysis of pro-inflammatory cytokines, MMPs, CCL20, and IL-17A. All inflammatory cytokines except IL-1α, IL-1β, and IL-6 had reduced corneal expression in dry groups that received nanowafer containing doxycycline or dexamethasone.

4. In Vivo Diffusion of Fluorescent Nanospheres from the Nanowafer into the Cornea and Conjunctiva In order to demonstrate the efficacy of the nanowafer in improving the diffusion of drug molecules and their increased residence times in the cornea, the following has been fabricated: (i) red fluorescent nanospheres (60 nm diameter)-loaded nanowafers and (ii) gold nanospheres (60 nm diameter)-loaded nanowafers. These nanowafers were instilled on the cornea of healthy mice. The mice were sacrificed after 2 and 5 days respectively and the eyes were collected. The eyes were microtomed to obtain 5 μm slices and were examined by confocal fluorescence imaging and transmission electron microscopy (TEM) to ascertain the diffusion and residence times of the nanospheres. As can be seen from FIGS. 16A-C, the red fluorescent nanospheres diffused into the cornea and remained there even after 5 days. To further confirm the nanoparticle diffusion in the cornea, gold nanosphere loaded nanowafers were placed on the corneas of healthy mice and the microtomed 5 μm slices were examined by TEM imaging. TEM analysis reaffirmed the results obtained by confocal fluorescence imaging. As can be seen from the FIGS. 16D-F, the gold nanoparticles (tiny black spots in the images) diffused into the corneal epithelium and stroma, and after 5 days the density of the gold nanoparticles was a little less. Taken together, these results confirm that the enhanced efficacy of the drug-loaded nanowafers in reducing the corneal roughness in the dry induced mice is because of the enhanced residence time and diffusion of the drug molecules into the conjunctiva and cornea (FIGS. 17 and 18). One characterizes the efficacy of nanowafer drug delivery systems in corneal would healing, nerve regeneration, and inhibiting corneal vascularization.

5. In Vivo Efficacy of the Nanowafers in Dry Eye Induced Mouse Model

In an exemplary study, the efficacy of drug released from the nanowafer was investigated in dry eye induced mouse model. Nanowafers having 500 nm nanoreservoirs loaded with drugs: dexamethasone and doxycycline were used in the study. A circular drug-nanowafer of ~1.5 mm diameter was placed under the lower and upper eyelids of a mouse under general anesthesia at baseline and subjected to desiccating stress for 5 days, with no topical treatment. Mice were euthanized and examined after 5 days for drug efficacy by optical microscopy and gene expression analysis. The regularity of a white-light ring reflecting off the mouse cornea was used to evaluate the corneal smoothness. The circularity of the ring is proportional to the smoothness of the corneal surface (de Paiva et al., 2006). Increase in corneal smoothness is indicative of the efficacy of the drug released from the nanowafer. As can be seen from FIG. 17A, the corneal ring is very irregular in experimental dry eye treated by the blank nanowafer (control), while in mice that received either doxycycline-nanowafer (FIG. 17B) or dexamethasone-nanowafer (FIG. 17C), the corneal surface was smooth and uniform. These results confirm that the controlled drug release from the nanowafer is effective in improving dry eye induced corneal irregularity.

To further evaluate the in vivo efficacy of the nanowafers, levels of inflammatory cytokines (ICK) and matrix metalloproteinase (MMPs) concentrations were analyzed by real time PCR analysis. There is an increased production of ICK and MMPs in the dry eye, hence, the in vivo efficacy of nanowafers can be evaluated by quantifying ICK and MMP expression (Luo et al., 2004; Solomon et al., 2001; Afonso et al., 1999; Pflugfelder et al., 2005; de Paiva et al., 2006; Luo et al., 2004; De Paiva et al., 2009). A decrease in ICK and MMP expression confirms an increased efficacy of the nanowafer drug delivery system. The initial studies demonstrate that a single administration of dexamethasone or doxycycline-loaded nanowafers in the conjunctiva of dry eye induced mice have significantly decreased the expression of pro-inflammatory cytokines, IL-1β, IL-6, MMP-3, MMP-9, CCL20 and the Th-17 signature cytokine, IL-17A in the corneal epithelium when compared to the blank nanowafer used as a control after 5 days of experimental dry eye (FIG. 18).

In Vivo Efficacy of the Nanowafers in Corneal Injury and Healing Mouse Model

Standard corneal abrasion studies were performed in C57BL/6J mice 2 and 4 months of age (Liu et al., 2012). Under general anesthesia, a central region of the cornea is demarcated in male or female mice using a 2 mm diameter trephine, and the epithelium and subbasal nerve plexus are removed with a golf club spud (Accutome, Inc., Malvern, Pa.). The natural healing response to this standardized lesion includes peak epithelial cell division at 18 hours, wound closure within 24 hours, return of full thickness stratification of the epithelium within 96 hours and ~20% recovery of subbasal nerve density in the wound area within 96 hours (Li et al., 2006; Byeseda et al., 2009; Li et al., 2011). By 3 hours after injury, the epithelium that is not directly injured by the abrasion upregulates expression of an array of proinflammatory cytokines, chemokines, adhesion molecules and growth factors, and limbal venules exhibit significant dilatation and neutrophil extravasation (Byeseda et al., 2009; Li, Burns, Han, et al., 2011; Li, Burns, Byeseda, et al., 2011; Li, Burns, Smith, et al., 2011). The neutrophils at 3 hours are mostly limited to the anterior limbus, continue to accumulate over time, and migrate in contact with keratocytes in the anterior stroma, arriving at the original wound margin within 6 hours and peaking in the cornea within 12 hours in male mice and 18 hours in females (Byeseda et al., 2009; Li, Burns, Han, et al., 2011; Li et al., 2006a; Li et al., 2006b; Petrescu et al., 2007; Gagen et al., 2010; Burns et al., 2005).

Figure 19:
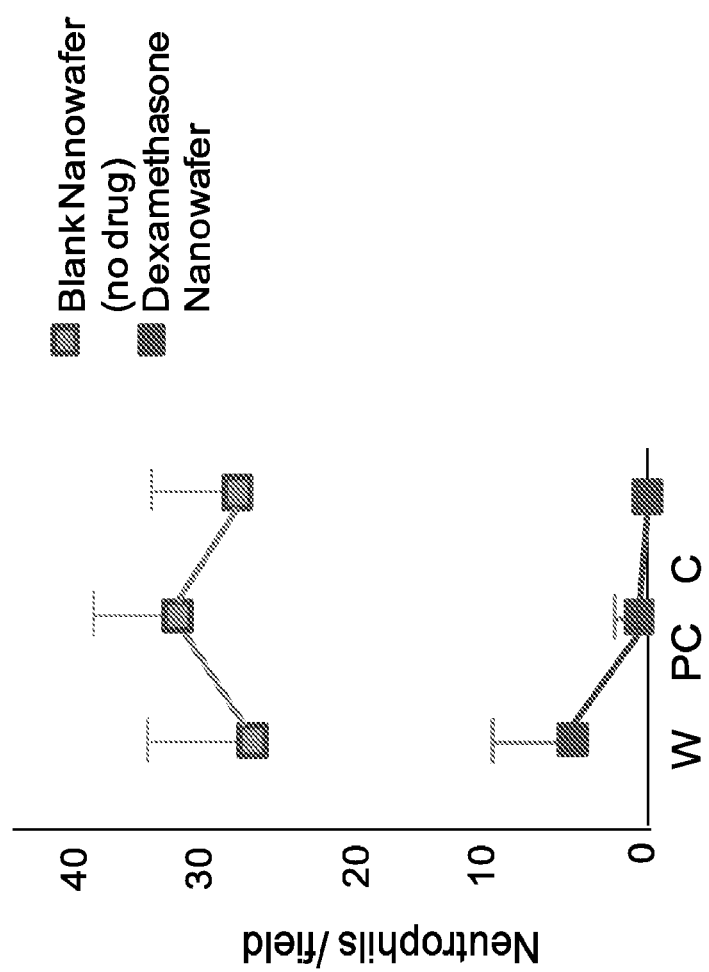
FIG. 19 shows efficacy of nanowafer on corneal injury healing. Inhibitor effect of dexamethasone loaded nanowafers on neutrophil accumulation in the wound, paracenter, and center of the cornea at 24 hours after epithelial abrasion compared to the blank nanowafers (containing no drug). P<0.01, n=4.

To investigate the effect of nanowafers on neutrophil migration and dividing epithelial cells, a blank polyvinyl alcohol (PVA) nanowafer was placed on the abrasion site of the cornea in a corneal abrasion mouse model. Corneal whole mounts collected at 24 hours after central epithelial abrasion were stained for neutrophils and dividing epithelial cells. Blank nanowafers (without drug) applied immediately after abrasion resulted in a significant reduction in neutrophils/field of view at the original wound margin (n=6) and altered distribution of dividing epithelial cells/field of view in the limbus (L), paralimbus (PL), original wound margin (W), paracenter (PC) and center (C) of the cornea (FIG. 19). Total dividing epithelial cells was not different from wounded corneas without treatment (total in 4 randomly selected fields of view in the paralimbal region per cornea). In the case of dexamethasone-loaded nanowafers, the migration of neutrophils to the site of the wound was strongly inhibited (FIG. 19). A small number of neutrophils migrated to the wound area and no neutrophils were observed in the paracentral and central regions of the wound. In comparison, blank nanowafer has no effect in inhibiting the neutrophil migration to the wound site. These nanowafers (both blank and dexamethasone-loaded) appear to influence epithelial healing, and will require detailed analysis of the extent of this effect with blank nanowafers (without drug) and drug loaded nanowafers (dexamethasone, tacrolimus).

In summary, these experimental results demonstrate: (i) feasibility of the research idea; (ii) nanowafer fabrication and controlled drug release attributes; (iii) mechanical compliance and mucoadhesiveness of the nanowafer; and (iv) single instillation of the nanowafers could significantly improve the ocular surface to smoothness after 5 days of experimental dry eye induced mice compared to twice a day topically administered Doxycycline and Dexamethasone drug solutions as eye drop formulations; and (v) dexamethasone loaded nanowafers decrease neutrophil infiltration of the cornea in a murine corneal abrasion model.

Fabrication of Nanowafers of Different Drug Reservoir Dimensions

The nanowafer can release the drug in a controlled release fashion for a longer duration of time (for example, from hours to a day to a week or more). In addition, the drug is released in therapeutically effective concentrations to elicit significant efficacy and minimize systemic toxicity. To maintain tight control over the drug release kinetics, the drug reservoir dimensions in the nanowafer must be carefully designed and optimized. As an initial study, nanowafers having 500 nm drug reservoirs were fabricated using PVA as a model system. While this demonstrated the feasibility of nanowafer fabrication, the drug content and drug release kinetics may be optimized for in vivo therapeutic efficacy. By choosing the right drug reservoir dimensions, the total drug content, drug release kinetics and the drug dosage can be controlled. A larger drug reservoir enables a higher drug loading and a longer duration of release, while less amount of drug can be loaded in smaller reservoirs for short-term release. In exemplary embodiments, nanowafers with drug reservoir dimensions of 100 nm, 250 nm, 500 nm, 1 µm, 1.5 µm and 3 µm are designed and fabricated by e-beam lithography and photolithography, for example. The drug reservoir dimensions can define the drug content and release kinetics thus imbuing the nanowafer with programmable attributes, in at least some embodiments. In addition, the nanowafer drug delivery system is expected to tightly control the drug release to maximize the therapeutic efficiency and minimize the toxic side effects (FIG. 12E). During the course of the drug release, the nanowafer slowly dissolves and fades away.

Polymers

In this study nanowafers are fabricated using different polymers. Screening different polymers enables selection of the right polymer for a specific drug. Different polymers interact differently with different drugs via hydrogen bonding, van der Waals interactions, hydrophobic interactions, etc. that will in turn affect the drug release kinetics. For example, if the drug is strongly hydrogen bonding with the polymer, then the drug release rate can be very slow and the bioavailability of the drug in the tissue can be very poor which will affect the drug efficacy. Also, in at least some cases for a successful nanowafer development, it should adhere well to the mucous layer of the conjunctiva and remain intact and withstand constant blinking. For the fabrication of hydrogel nanowafers, polymers having the following attributes will be chosen, in some embodiments: (i) water-soluble nature of the polymers, (ii) biocompatibility, (iii) transparency of the nanowafers, (iv) mucoadhesive property, (v) mechanical compliance so as to readily conform to the curvature of the eye, and (vi) FDA approved polymers that are in clinical use. In this study, the following synthetic and natural biopolymers aree examined, in specific embodiments: PVA, dextran, polyvinyl pyrrolidone, carboxymethyl cellulose, (hydroxypropyl)methyl cellulose, gelatin, and collagen will be used for the fabrication of nanowafers.

Drugs

In order to develop a broadly applicable nanowafer system, the nanowafer efficacy studies will be conducted using the following drugs/therapeutics: riboflavin, doxycycline, dexamethasone, phospho dexamethasone, tacrolimus, topiramate, etifoxine, vinaxanthone, and neotrofin, sorafenib, sunitinib, cyclosporin A, avastin, ciproflaxacin, levofloxacin, erythromycin, acyclovir, valacyclovir, ganciclovir, cysteamine, cysteamine hydrochloride, cysteamine tartrate, brucellamine, tiopronin, anti-IFNγ, and limbal stem cells.

Cyclosporin A eye drops are already in clinical use and the efficacy of cyclosporin A loaded nanowafer can be compared with the commercially available eye drop formulation. The effect of IFNγ in the pathologic apoptosis of conjunctiva and deterioration of dry eye condition is known (Cho et al., 2012; Gayton, 2009). In embodiments, therapeutic effect of anti-IFNγ-loaded nanowafers is provided for treating the dry eye disease. Dexamethasone is a corticosteroid and is an FDA approved anti-inflammatory drug. However, dexamethasone eye drops cause side effects such as an increase in the blood glucose level in diabetic patients. Dexamethasone loaded nanowafers, because of its controlled drug release and localized drug distribution in the cornea and conjunctiva, are examined for its efficacy and minimizing systemic side effects in a corneal abrasion mouse model. To stimulate nerve regeneration in the injured cornea, Tacrolimus-loaded nanowafers are investigated. Tacrolimus promotes nerve regeneration and recovery of neural functions, however, it also demonstrates a strong immunosuppressive tendency. As a consequence, tacrolimus eye drop and systemic injection are met with limited success. Because the nanowafer can deliver the drug locally at the injured corneal site in a controlled release fashion, therapeutic efficacy of tacrolimus-loaded nanowafer is utilized for the stimulation of nerve regeneration and minimizing the systemic side effects.

To inhibit corneal neovascularization after injury, nanowafer loaded with anti-angiogenic drugs: sorafenib, sunitinib, and avastin are utilized. These drugs are already in clinical use as anti-angiogenic therapeutics. However, delivering these drugs locally to the cornea in a controlled release fashion to prevent systemic side effects is a challenging task. Because the nanowafer can deliver these drugs locally at the site of corneal injury in a controlled release fashion, therapeutic efficacy of anti-angiogenic drug loaded nanowafer are utilized for the inhibition of angiogenesis and regression of neovasculature in corneal vascularization mouse model.

Investigation of Nanowafer Efficacy in Dry Eye Induced Mouse Model

Dry eye is a multifactorial disease that may result in an abnormal ocular surface accompanied by irritation, blurred and fluctuating vision, tear film instability, increased tear osmolarity and ocular surface epithelial disease (Pflugfelder et al., 2007). Dry eye disease severely impacts the quality of life by decreasing functional vision and the ability to perform normal daily activities (Zoukhri, 2006). The causative factors for dry eye include inflammation, hormonal imbalance, age, and environmental triggers, which set in motion a self-perpetuating series of events that affect the ocular surface, lacrimal glands, meibomian glands, and the neural network (Miljanoviae et al., 2007; Lpez and Ubels, 1991; Lopez and Ubels, 1993; Nagelhout et al., 2005). Tear gland malfunction leads to changes in tear composition such as hyperosmolarity which triggers the production of inflammatory cytokines that have been identified in the tear film of dry eye disease patients. Inflammation is considered to be an important pathogenic factor and treating it can restore the ocular surface. Mild dry eye is treated with artificial tear eye drops for temporary relief. Chronic dry eye as a consequence of inflammation are treated with eye drops containing topical anti-inflammatory drugs or immunosuppressants such as doxycycline, dexamethasone and cyclosporine, respectively (Avunduk et al., 2003).

Figure 10:
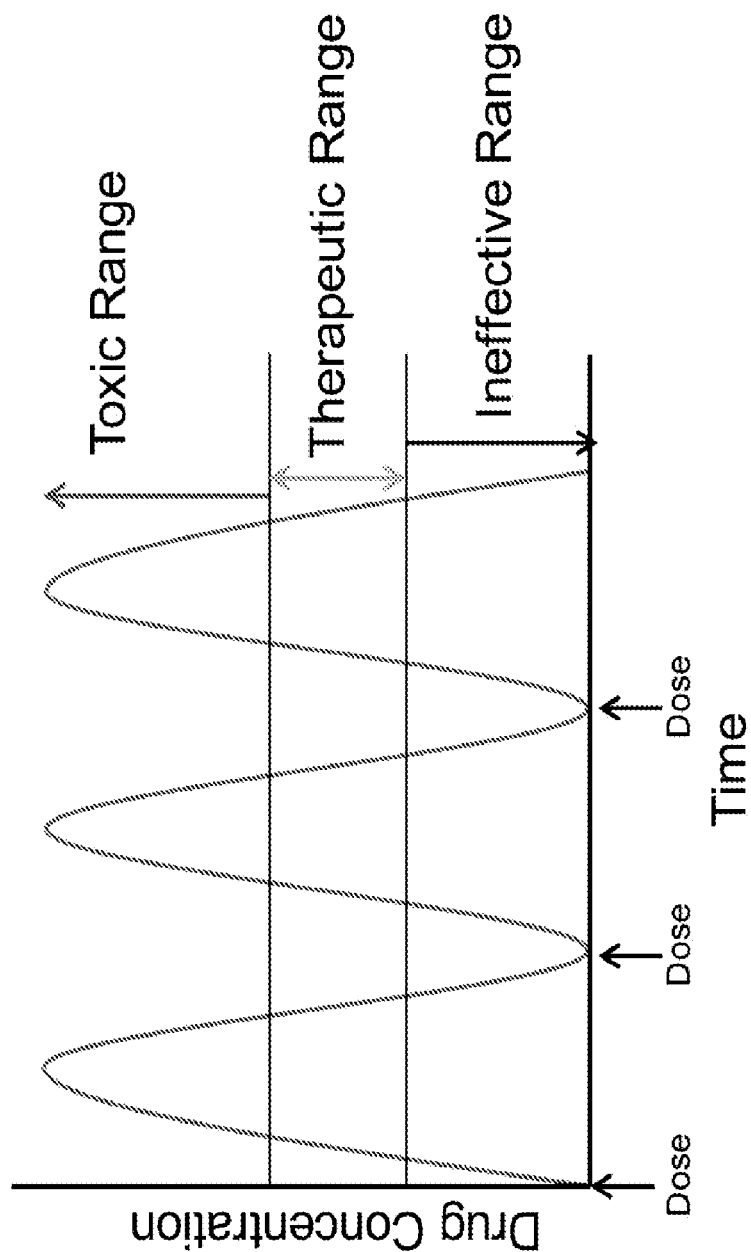
FIG. 10 illustrates a typical drug concentration profile for a conventional administration method.

The T helper cell cytokine IFN-γ has been identified as having a key role in promoting conjunctival squamous metaplasia, loss of mucus producing goblet cells, dry eye, and surface epithelial apoptosis. Topically or systemically administered anti-IFN-γ can prevent epithelial apoptosis and preserve goblet cells (Cho et al., 2012; Gayton, 2009). Use of biologics, such as IFN-γ for treatment of dry eye in a mouse dry eye model would be a major advancement, however the delivery of antibodies to the ocular surface has been a challenging task due to the instability of the formulation, proteolytic degradation, blinking and clearance into the lacrimal drainage system. As a consequence, multiple administrations of an expensive antibody solutions are required in the eye to obtain therapeutic effect. Administration of eye drops several times in a day result in high and low drug concentration profiles, i.e. high concentration in the toxic range and low concentration in the ineffective range, in addition to therapeutically effective range (FIG. 10). To characterize the therapeutic efficacy of anti-IFN-γ loaded nanowafers on ocular surface epithelial disease in dry eye, an experimental dry eye induced mouse model is utilized. This mouse model closely replicates dry eye disease conditions and certain parameters that verify efficacy of the anti-IFN-γ loaded nanowafers are well validated. Development of a novel drug delivery system to deliver biologics in a stable controlled release manner is a major advancement in the treatment of corneal and ocular surface diseases.

Investigation of Nanowafer Efficacy in Corneal Epithelial Healing and Nerve Regeneration One can analyze the influence of nanowafers, with and without incorporated drugs, on the status of inflammation and healing in the cornea. Healing includes epithelial restoration and regeneration of sensory nerves, and the status of inflammation in the cornea involves understanding pro- and anti-inflammatory responses to the drug-loaded nanowafers. The inflammatory response to injury involves a complex cascade of factors and cell types that critically influences healing. It contributes important aspects to recovery, but if dysregulated can enhance tissue damage and disrupt healing. Defining the status of key steps in the cascades provides useful insights for assessing the optimum nanowafer delivery system for wound healing and corneal nerve regeneration. One can consider two distinct test settings, for example: (i) influence of dexamethasone-loaded nanowafers on epithelial nerve density and wound healing; and (ii) influence of tacrolimus-loaded nanowafers on subbasal and epithelial sensory nerve regeneration.

Exemplary Devices

Nano and microparticles have been developed for systemic drug delivery however, not much progress has been made in the development of nanotechnology based drug delivery systems for treating ocular diseases. Recently, micro and nanoparticles have been used in ocular drug delivery with limited success. The nanoparticle suspensions were also rapidly cleared from the eye leading to limited drug efficacy. Micro-/nanoparticle-based delivery systems are easy to prepare, but exhibit limitations, such as: low drug loading, burst drug release kinetics, and clumping of the particles. Also, due to the very short period of drug release (~1-3 h), the therapeutic efficacy is very limited, requiring multiple administrations. To improve the drug retention time in the eye, in situ gel forming systems have been developed. A solution containing drug upon instillation as eye drops undergo sol-to-gel phase transition on the eye surface. The in situ formed gels are expected to hold the drug for a longer period of time thus enhancing its bioavailability. However, these in situ forming gels could increase the drug retention times to a few hours. Drug-loaded contact lenses have been developed to improve the drug retention time in the eye. Because contact lenses are in constant contact with the cornea, drug-loaded contact lenses are expected enhance the drug retention times to more than 30 min. The problem with these systems is that most of the drug diffuses out in an hour or more. As a further advancement, contact lenses loaded with drug filled liposomes, micelles, microemulsions or nanoparticles have been developed. These approaches have improved the drug retention times for a few hours, however are not well suited for extended release for a day to a week. Recently, drug-loaded polylactide-co-glycolide (PLGA) films were encapsulated inside the contact lenses for the long-term release of econazole. Although, these systems could deliver the drug for up to a month, are limited by reduced transparency and low oxygen permeability because of the thick PLGA film. Also, because of the biodegradable nature of PLGA, these contact lenses cannot be packaged in PBS. In summary, all these systems, although could extend the drug retention times by a few hours, they could not release the drug in a controlled release fashion for extended periods of time. Considering these limitations, development of a long-term release nanowafer drug delivery system that can be readily instilled on the cornea, conjunctiva, or in the fornix of the eye by the patient's fingertip without any clinical procedure will be not only very convenient, but also most desirable for treating chronic dry eye, glaucoma, corneal ulcers, and other ocular inflammations/infections.

The present disclosure provides certain embodiments of a drug delivery system that release the drug in a therapeutically effective concentration for a desired duration of time. In one aspect, the embodiments of the present disclosure releases a therapeutically effective concentration for a longer time period than other delivery systems, for instance from at least a day to a week. Certain embodiments of the drug delivery system of the present disclosure comprises a therapeutics dispensing device comprising a biodissolvable hydrogel matrix for long term drug release that allows the device to be placed directly at the diseased or injured site, e.g., onto the surface of the eye, and retained there rather than through topical administration or injection, whether locally or systematically.

Figure 2:
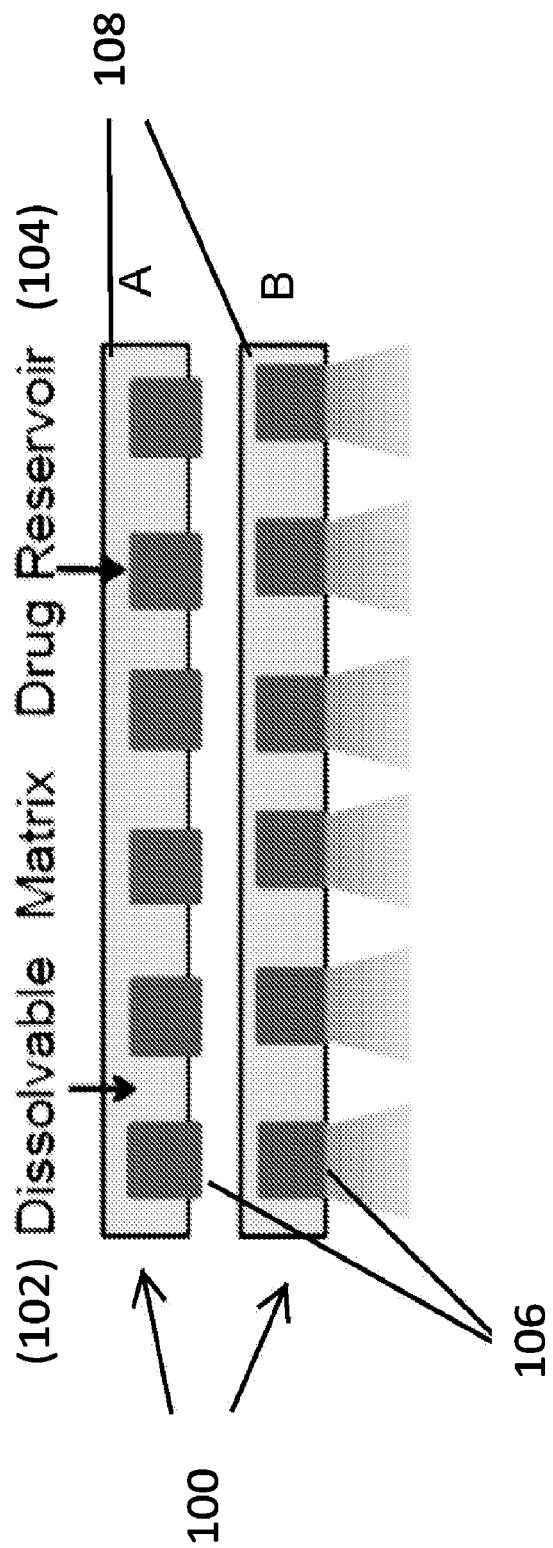
FIGS. 2A and 2B are a cross section view of the therapeutics dispensing device depicted in FIG. 1.

In a specific exemplary embodiment, FIG. 1 shows therapeutics dispensing device 100 with a hydrogel matrix 102 and drug reservoirs 104. While FIG. 1 shows therapeutics dispensing device 100 as being circular, it can have any shape, regular or irregular, as desired or dictated by the application and/or site of injury. In certain embodiments, the shape of therapeutics dispensing device 100 is based at least on the material of hydrogel matrix 102. Therapeutics dispensing device 100 can also be called a "nanowafer" if certain dimensions, such as reservoir depth, are in the nanometer range and a "microwafer" if the dimensions are in the micrometer range. In certain instances, these terms are used interchangeably and do not adhere to the size reference. FIGS. 2A-2B show a cross section of therapeutics dispensing device 100. Therapeutics dispensing device 100 comprises a series of drug reservoirs 104 disposed throughout hydrogel matrix 102. Drug reservoirs 104 are preferably arranged in a patterned array. Therapeutics dispensing device 100 has open face 106 with the top of drug reservoirs 104 exposed and closed face 108, toward which the bottom drug reservoirs 104 are located. Referring to FIG. 2B, in the preferred embodiment, open face 106 is placed adjacent to the diseased or injured site to deliver drugs from drug reservoirs 104 at a control manner as the portion of hydrogel matrix 102 around open face 106 is slowly cleared away by the circulation of fluid (e.g., tear) on the surface of the eye. Dissolution of open face 106 of therapeutics dispensing device 100 slowly exposes drug reservoirs 104 to the surrounding tissue, thus allowing for the duration of drug release to be controlled by configuring the materials of therapeutics dispensing device 100 to have a certain rate of dissolution. Hydrogel matrix 102 protects the drug not exposed to the surrounding tissue from being released or cleared by various systems in the body. In certain embodiments, the therapeutics contained in drug reservoirs 104 includes at least one of the following: various chemical compounds, drugs, including anti-inflammatory agents, as well as drug matrices, other small molecule drugs, antibodies, antibiotics, siRNAs, peptides, steroids, including corticosteroids, biologic antifungal agents, amino acids, mRNAs, proteins, nutrient supplements, or any combination thereof.

Hydrogel matrix 102 preferably comprises a biocompatible material that dissolves or degrades over a period of time to release the drug in the drug reservoirs. The biocompatible material preferably comprises dextran, polyvinyl alcohol, carboxy methyl cellulose, hydroxypropyl cellulose, polyvinylpyrrolidone, polyvinyl alcohol (PVA), Polylactide-co-glycolide (PLGA), polyhydroxy ethyl methacrylate (Poly-HEMA), Polyhydroxy ethylacrylate, gelatin materials, collagen materials, and any combination thereof. PVA, Poly-HEMA, and PLGA are FDA approved biopolymers with a history of safe human use in sutures, bone plates, contact lenses and extended-release pharmaceuticals. In an embodiment where hydrogel matrix 102 comprises PLGA, over time, the PLGA polymer breaks down into lactic acid and glycolic acid, which are completely metabolized by the body and eliminated as carbon dioxide and water, thereby releasing the medication in drug reservoirs 104. Not intended to be bound by theory, the PLGA matrix upon implantation begins to absorb water almost immediately, leading to swelling of hydrogel matrix 102. In the preferred embodiment, this process begins a phase in which a small amount of the drug from drug reservoirs 104 present at or near the surface of hydrogel matrix 102 is released. Over a period of time, fluid in the eye or on the surface of the eye, such as tears, slowly breaks down the polymer structure allowing release of the drug, resulting in a sustained supply of the drug at the implant site. The polymer matrix eventually breaks down into oligomers and monomers, resulting in the complete release of the drug at the end the desired duration. Further, hydrogel matrix 102 preferably protects drug reservoirs 104 from the proliferation of scar tissue around them.

In the preferred embodiment, hydrogel matrix 102 comprises a biodissolvable material, which breaks down into individual units in solution rather than a biodegradable material, which breaks down into relatively larger portions that are further divided over time. The dissolution of a matrix is preferred because it allows for control over the release of the drugs where only the portions exposed to solution would dissolve, leaving the rest of the device intact. Further, the dissolved particles pose a smaller risk of damage to the body, especially the injury site.

In the preferred embodiment, therapeutics dispensing device 100 has a diameter of about 2-9 mm. Drug reservoirs 104 preferably has a depth of between about 200 nanometer and 50 micrometers, preferably about 250 nm, 500 nm, 1 micrometer, 1.5 micrometers, and 3 micrometers. The shape of drug reservoirs 104 can vary as desired. The number, depth, shape, and other dimensions of drug reservoirs 104 can vary to achieve the desired amount of therapeutics to be placed on therapeutics dispensing device 100 of a certain size. That is the dimensions of therapeutics dispensing device 100 and drug reservoirs 104 can be adjusted based on a number of factors, including but not limited to, the type of drug, amount of drug desired, the material of hydrogel matrix 102, the organ or location where therapeutics dispensing device 100 will be placed.

Figure 11:
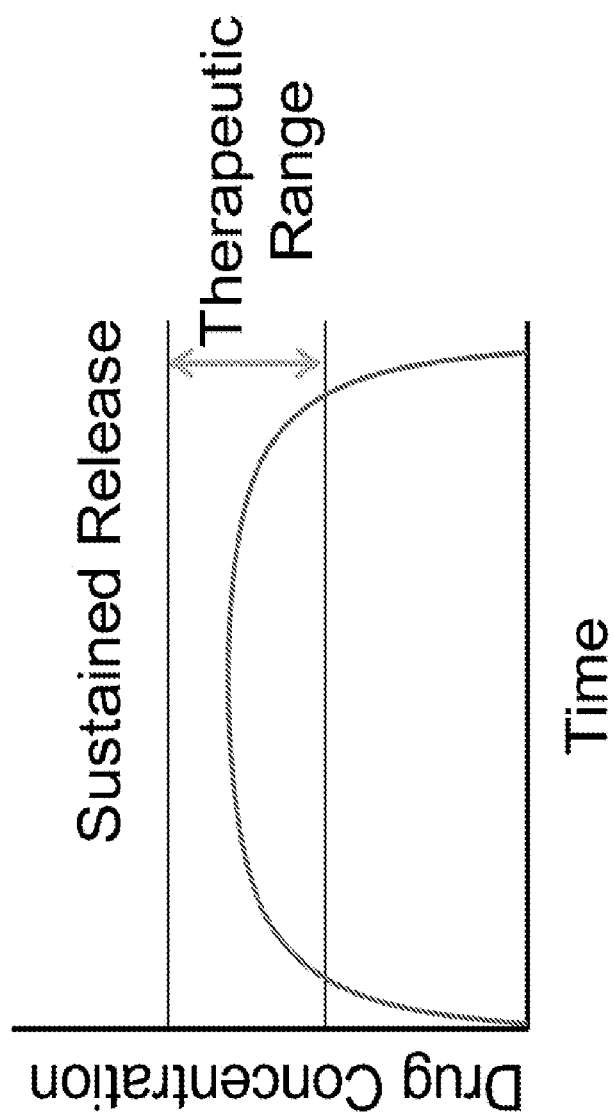
FIG. 11 illustrates an exemplary drug concentration profile for an embodiment of the therapeutic device of the present disclosure.

Because drug is only released as open face 106 of therapeutics dispensing device 100 is dissolved, certain embodiments of the present disclosure allows for longer terms drug release of at least one day (or 24 hours) when compared to other traditional drug release methods. For instance, drugs administered through ingestion remain in the system at therapeutically effective dose for only between 3-12 hours or drugs administered through eye drops remain effective in the eye for less than 1 hour. This is demonstrated by the drug concentration profile in FIG. 10, which shows the drug concentration peaks, as well as declines, rapidly, and subsequent dosages are required to bring the drug concentration to within the therapeutic range for treatment. Unlike conventional methods, the materials of therapeutics dispensing device 100 can be configured or programmed to suit the patient requirement. In addition, the desired drug release profiles (e.g., continuous or variable over a desired time period) can be obtained by fabricating hydrogel matrix 102 using different polymers, such as dextran, polyvinyl alcohol, carboxy methyl cellulose, hydroxypropyl cellulose, polyvinylpyrrolidone, polylactide-co-glycolide (PLGA), polyhydroxy ethyl methacrylate (PolyHEMA), Polyhydroxy ethylacrylate, or any combination thereof. FIG. 11 illustrates an exemplary drug profile concentration that can be achieved with certain embodiments of therapeutics dispensing device of the present disclosure where one dose can maintain a drug concentration within the therapeutic range over a prolonged period of time, such as hours, days, and/or weeks, where the rate of release and/or treatment period can be programmed (e.g., controlled).

One particular application for certain embodiments of the therapeutics dispensing device of the present disclosure is mild dry eye, which is treated with artificial tear eye drops with no biological activity that provide only mild temporary relief. Chronic dry eye and inflammation occurring in response to tear film hypertonicity are treated with eye drops containing topical steroids or immunosuppressants such as dexamethasone and cyclosporine, respectively. It is very difficult to maintain therapeutically effective concentration of the drug for extended periods of time because of its rapid clearance by blinking and lacrimal drainage system. As a consequence, multiple administrations are required in the eye to obtain therapeutic effect. Administration of eye drops several times in a day result in high and low drug concentration profiles, i.e. high drug concentration in the toxic range and low concentration in the ineffective range, in addition to therapeutically effective range (FIG. 10).

As mentioned above, drug release from the nanowafer can be programmed by choosing the right drug reservoir dimension and drug loading concentration. Smaller reservoir dimensions enable a slow diffusion of drug molecules and a slow release, while drug molecules diffuse rapidly from larger reservoirs. Similarly, a low drug loading concentration results in slower release while a higher concentration leads to rapid release. The drug release from the nanowafer may be classified into 4 categories based on three parameters: the magnitude of initial burst release, the extent of drug release, and the drug release kinetics followed by the burst release. The preferred release profile is one that involves a small burst release, which is typically smaller than 20% of the total loaded drug, followed by almost zero-order release for an extended period of time until most of the drug is released. The difference between the two profiles may be the extent of the initial burst release. One profile may have a high burst release followed by steady release of the drug.

Another aspect of the present disclosure provides methods to fabricate certain embodiments of the therapeutics dispensing device of the present disclosure. In the preferred embodiment, embodiments of the therapeutics dispensing device of the present disclosure are generated using e-beam lithography and biofabrication. Referring to FIG. 3, therapeutics dispensing device 300 is fabricated using template 302 having a series of posts 304 coupled to base 306. Drug reservoirs 308 of therapeutics dispensing device 300 have the same dimensions and arrangement as posts 304. Accordingly, posts 304 are configured with the desired dimensions of drug reservoirs 308. Further, the shape and dimensions of hydrogel matrix 310 of therapeutics dispensing device 300 are the same as base 306. For example, to fabricate a circular therapeutics dispensing device with a diameter of 2 mm having twenty drug reservoirs arranged in a pattern of four rows of five drug reservoirs, each reservoir of 1 micrometer depth, the template would have a circular base of 2 mm and the corresponding number of posts with the desired dimensions and pattern. Template 302 preferably comprises silicon or quartz glass. Template 302 can be microfabricated, preferably using e-beam lithography followed by plasma etching.

Referring to FIG. 3A, a first step comprises forming template 302 having a pattern of vertical posts 304 on substrate 306. In an alternative embodiment, a mold generally resembling the hydrogel matrix in FIG. 3C can be used to form an intermediate template (not shown). For instance, the mold can be made of a rigid material and has a plurality of reservoirs corresponding to the desired drug reservoirs. The material for the intermediate template can be flexible and can exist in liquid form prior to being solidified, such as silicone rubber or polydimethoxy silane (PDMS). The material of the intermediate template can be poured into the mold and allowed to be set to form the intermediate template, resembling template 302 of FIG. 3A. Referring to FIG. 3B, a solution of biocompatible material with the desired compositions for use as the hydrogel matrix is poured onto template 302 and allowed to solidify according to the compositions' properties. For instance, if PVA solution is used as the hydrogel matrix, the solution is preferably heated for about 30 minutes at about 70° C. Referring to FIG. 3C, once biocompatible material layer 312 is solidified, it is peeled off and attached to a flat glass plate to expose drug reservoirs 308. Referring to FIG. 3D, drug reservoirs 308 are filled with the desired substance such as therapeutics including various drugs, including anti-inflammatory agents, as well as drug matrices, other small molecule drugs, antibodies, antibiotics, siRNAs, peptides, steroids, including corticosteroids, biologic antifungal agents, amino acids, mRNAs, or any combination thereof, using microinjection, preferably, using an ultrasonic atomizing nozzle.

Figure 4:
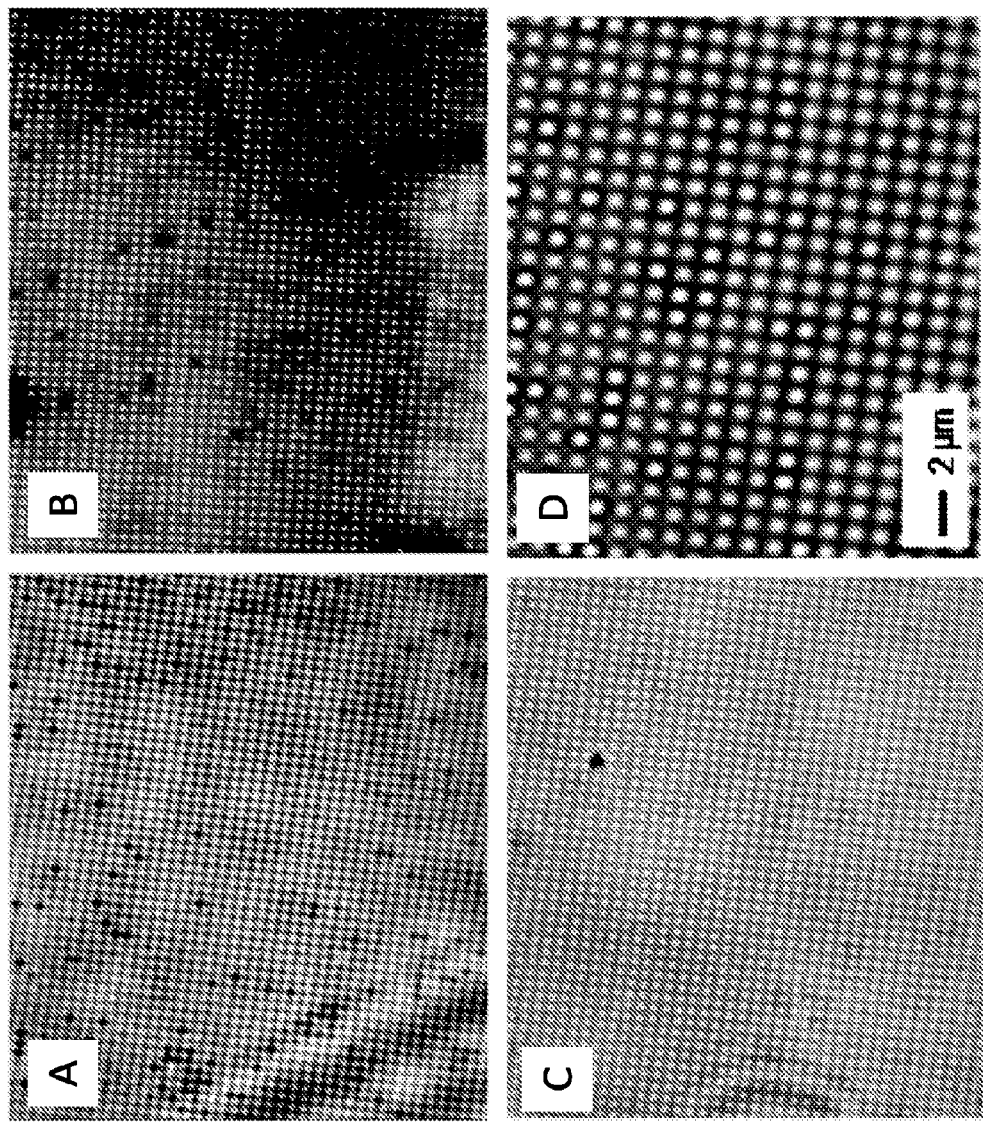
FIGS. 4A-4D are images of one embodiment of a therapeutics dispensing device of the present disclosure loaded with various substances.

The integrity of embodiments of the therapeutics dispensing device of the present disclosure can be characterized by confocal fluorescence and SEM imaging. FIG. 4A is a bright field image of a therapeutics dispensing device fabricated according to the aspects of the present disclosure using a PVA solution and filled with Oregon Green-Dextran fluorescent dye. The drug reservoirs dimensions are 500 nm diameter and 500 nm deep. FIG. 4B is a fluorescence image of the same device, which demonstrates that the disclosed process that fill the nano-size drug reservoirs. FIGS. 4C and 4D are bright field images of a therapeutics dispensing device fabricated according to the aspects of the present disclosure using a PVA solution and filled with dexamethasone drug at different magnifications.

Figure 5:
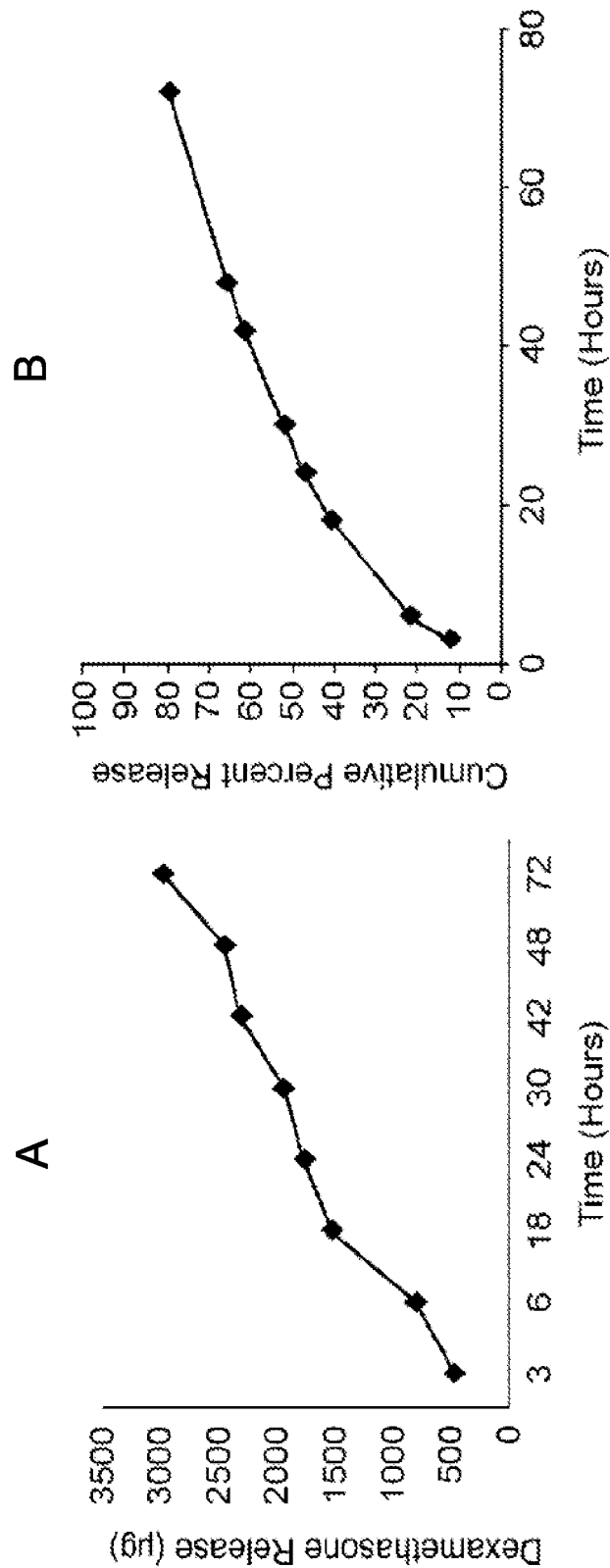
FIGS. 5A and 5B are drug release profiles of dexamethasone from an embodiment of a therapeutics dispensing device of the present disclosure.

FIGS. 5A-5B show the drug release kinetics of therapeutics dispensing devices of the present disclosure loaded with dexamethasone. The tested devices were formed according to the following protocol, which is intended to be exemplary and not limiting.

Filling the Reservoirs with Dexamethasone

A therapeutics dispensing device fabricated is filled with Dexamethasone solution by microinjection. A 5% Dexamethasone solution was used to fill the device. The concentration of the drug solution (1-20%) can be adjusted to suit the required dosage and duration of release.

Filling the Reservoirs with Doxycycline

Another therapeutics dispensing device fabricated is filled with Doxycycline solution by microinjection. A 5% Doxycycline solution was used to fill the nanowafers. The concentration of the drug solution (1-20%) can be adjusted to suit the required dosage and duration of release.

In Vitro Release of Dexamethasone from Devices

In a typical experiment, three Dexamethasone-loaded nanowafers (1 cm×1 cm) were separately weighed into three 10 ml glass vials, and 5 ml of PBS/Tween-20 (pH 7.4)

release medium was transferred into each vial. These vials were kept in an orbital shaker maintained at 37° C. with constant agitation. At 2 hour time intervals, 5 ml of the release medium was withdrawn from the vials and replaced with the same amount of the fresh medium. Thus collected samples were transferred into glass vials and stored in the refrigerator. Sampling of the release medium was continued for 5 days. Each sample was filtered through a 0.5 μm syringe filter and subjected to HPLC analysis. In this study, a mixture of methanol (90%) and ammonium acetate (10%, pH 7) was used as a mobile phase after filtration through 0.22 μm membrane filter.

Determination of Total Dexamethasone Content in Dex-Nanowafers

The total amount of a Dexamethasone loaded in the nanowafer was determined by dissolving an accurately weighed Dexamethasone-loaded nanowafer (1 cm×1 cm) in 5 ml water, followed by addition of ethanol (9 ml). The precipitated PVA was removed by centrifugation. The clear solution was rotary evaporated and the solid formed was redissolved in 10 ml of the mobile phase (90% methanol and 10% ammonium acetate, pH 7). An aliquot of this solution was filtered through a 0.5 μm syringe filter, analyzed by HPLC, and compared with the standard curve to quantify the Dexamethasone content.

As can be seen from FIGS. 5A-5B, the initial release after 6 hours is less than 20%. Because of the relatively low initial release, the therapeutics dispensing device can remain at the insertion site and continue to release the drug in the drug reservoirs for at least 3 days.

Figure 6:
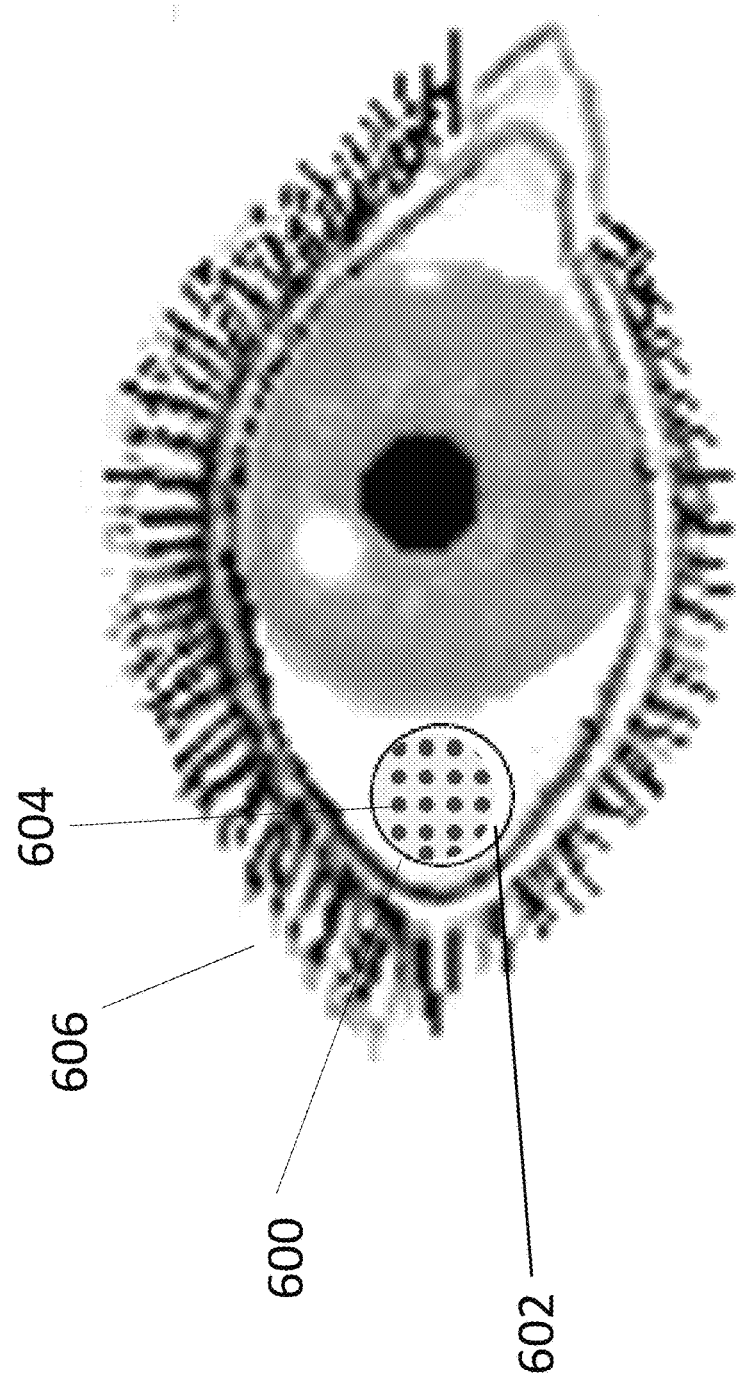
FIG. 6 is an illustration of an exemplary application of certain embodiments of the therapeutics dispensing device of the present disclosure.

Referring to FIG. 6, while the embodiments of the therapeutics dispensing device of the present disclosure have many applications, they are particularly applicable to provide controlled release of therapeutics in the eye for a prolonged duration (e.g., at least 1 day). In FIG. 6, therapeutics dispensing device 600 is inserted in eye 606 and delivers the substance in drug reservoirs 604 as hydrogel matrix 602 dissolves in a predetermined manner and duration. The composition of hydrogel matrix 602 is configured so that therapeutics dispensing device 600 remains in eye 606 for a predetermined amount of time to retain the drug in a protected environment and only release it to the surrounding tissue as hydrogel matrix 602 dissolves in a predetermined manner. In the preferred embodiment, device 600 is configured to dissolve completely within the predetermined time period. In another embodiment, device 600 can be removed after a predetermined period of time.

The prolonged release period at the target is an advantage over delivery through eye drops where the drug is available only for a short period of time (~20 mins), and most of the drug will be lost. Further, eye drops are inconvenient, especially when repeated dosing is required to treat chronic conditions. The embodiments of the therapeutics dispensing device of the present disclosure also provide benefits over the presently available ocular drug delivery implants include: Ocusert, Vitrasert, Retisert, and Iluvien. Ocusert drug delivery system, which were was developed by Alza Corporation for the delivery of pilocarpine to treat glaucoma and other ocular implants such as Vitrasert and Retisert developed by Bausch & Lomb. All these implants are made of non-biodegradable materials and require surgical implantation.

The embodiments of the therapeutics dispensing device of the present disclosure also have advantages over injection of drug-loaded micro or nanoparticles, which allow for local delivery but suffer from other drawbacks. For instance, injected micro or nanoparticles are limited because they can only hold a low amount of drug. Further, their release kinetics that are not easily controlled (e.g., they release the drug in bursts). In addition, their injections can lead to clumping of the particles at the injection site or growth of scar tissue around these clumps leading to cyst formation. Because the injected particles are rapidly cleared from the eye, they provide a short period of drug release (~1-3 h). As such, the therapeutic efficacy of the injected micro or nano particles is very limited, thereby requiring repeated dosing.

The embodiments of the therapeutics dispensing device of the present disclosure provide the prolonged release period of at least six hours, something that other systems have not been able to achieve. For instance, in situ gel forming systems with a solution or suspension containing drug upon instillation as eye drops that undergo sol-to-gel phase transition on the surface of the cornea or conjunctiva only increase the drug retention duration to a few hours. Also, drug-loaded contact lenses can only enhance the drug retention duration to more than 30 min. Even the more recent system of drug-loaded PLGA films, which are encapsulated inside the Poly(2-hydroxyethyl methacrylate) contact lenses are limited by reduced transparency and low oxygen permeability because of the thick PLGA film.

As described, the therapeutics dispensing device of the present disclosure has a high drug loading capability, predefined drug release kinetics, and prolonged delivery period, as compared to other delivery systems. For instance, at least 20% and preferably 25% of the composition of the therapeutics dispensing device can comprise the substance to be delivered, e.g., medication, which is higher than other systems, such as injected micro or nanoparticles.

Figure 7:
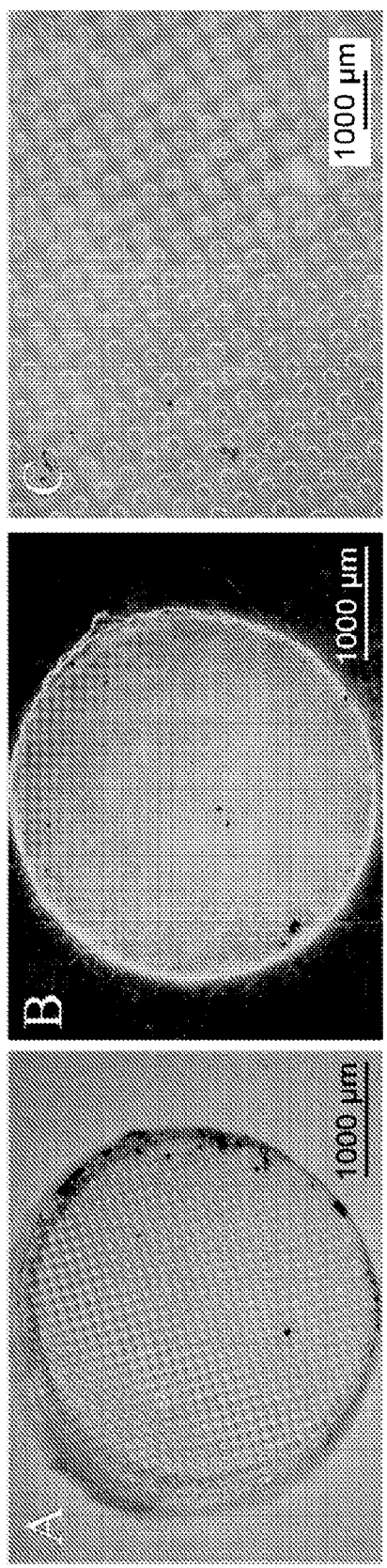
FIGS. 7A-7C are images of one embodiment of a therapeutics dispensing device of the present disclosure loaded with doxycycline.
Figure 8:
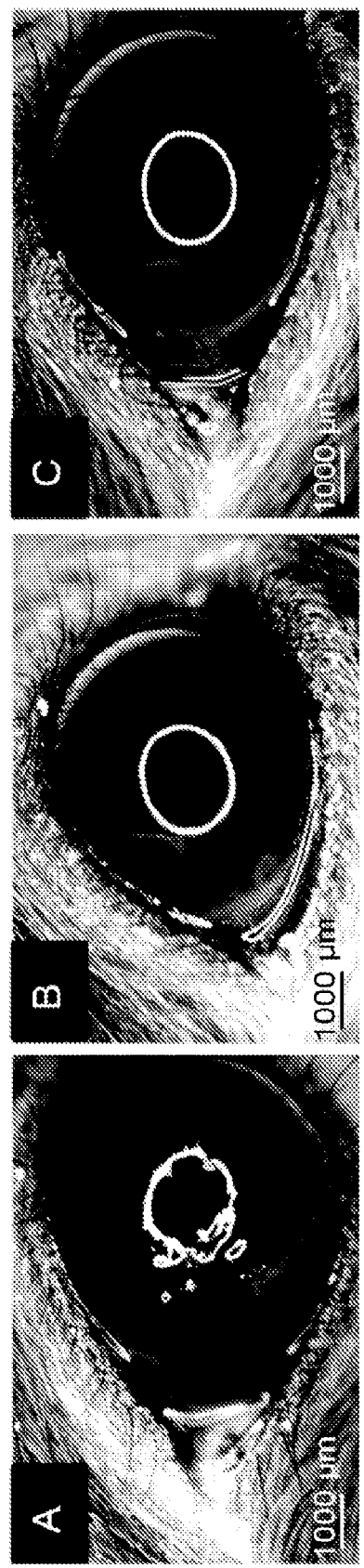
FIGS. 8A-8C are images of corneal smoothness evaluation in dry eye induced mice treated with one embodiment of the therapeutics dispensing device of the present disclosure loaded with: (A) blank PVA nanowafer (control); (B) doxycycline loaded nanowafer; and (C) dexamethasone loaded nanowafer.

While the therapeutics dispensing device of the present disclosure can be formed in any shape, the preferred shape for an ocular insert is a circular disc, as shown in FIGS. 7A, 7B, and 8A. It is preferred that the disc has a surface area that adequately covers the entire cornea without sticking to the eyelids or move with blinking for treatment of corneal disease or adheres to the bulbar or tarsal conjunctiva for treatment of ocular surface diseases, glaucoma, or ocular inflammatory diseases. The preferred diameter for achieving these objectives is about 9 mm.

In FIG. 7, nanowafers loaded with Docycycline (5%) were presented. Each wafer is ~3 mm in diameter. Representative pictures of doxycycline-loaded microwafer. (A) bright field image (2×); (B) fluorescence image (2×); C Image in B visualized under higher magnification (5×).

Using a fast (3-5 days) degradable doxycycline microwafer, sequential imaging of eyes were performed from 6 hours to 7 days after the placement of the microwafer. Intensity of autofluorescence of doxy-microwafer was measured in digital images by delineating the total area occupied by the microwafer and the results averaged within the group. The initial dissolution of a 3-mm doxy-wafer can be seen at 6 hours after placement and its disappearance over a period of 7 days. Autofluorescent is inversely proportional to the drug content in the microwafer.

In one exemplary study, the efficacy of drug released from the nanowafer was investigated in dry eye induced mouse model. The drug loaded nanowafers: (1) dexamethasone-nanowafer, and (2) doxycycline-nanowafer were used in this study. A circular drug-nanowafer of ~2 mm diameter was placed under the lower eyelid of a mouse and examined after 5 days for drug efficacy by optical microscopy. Corneal smoothness was evaluated in an image of a reflected light ring taken microscopically. The circularity of the ring is proportional to the smoothness of the corneal surface. Increase in corneal smoothness is indicative of the efficacy of the drug released from the nanowafer. As can be seen from the FIG. 7A, the cornea is very uneven in experimental dry eye treated by an instilled blank microwafer as a control. In the case of mice instilled with doxycycline-nanowafer (FIG. 7B) and dexamethasone-nanowafer (FIG. 7C), the corneal surface was smooth and uniform, confirming that the controlled drug release from the nanowafer is effective in improving dry eye induced corneal epithelial disease. In comparison, the dry eye induced in mice administered twice a day with doxycycline and dexamethasone eye drops did not show as much improvement in smoothening of the corneal surface after 5 days. This study confirms that one single nanowafer instillation is very efficacious for 5 days or even more compared to several daily doses of eye drops.

FIGS. 8A-8C show images taken in a study to evaluate the efficacy of drug released from an exemplary embodiment of the nanowafer of the present disclosure. In this particular study, dry eye induced mouse model was used. The following drug loaded nanowafers were used in the study: (1) dexamethasone-nanowafer, and (2) doxycycline-nanowafer. A circular drug-nanowafer of ~2 mm diameter was placed under the lower eyelid of a mouse and examined after 5 days for drug efficacy by optical microscopy. Corneal smoothness was evaluated in an image of a reflected light ring taken microscopically. The circularity of the ring is proportional to the smoothness of the corneal surface. Increase in corneal smoothness is indicative of the efficacy of the drug released from the nanowafer. As can be seen from the FIG. 8A, the cornea is very uneven in experimental dry eye treated by an exemplary embodiment not filled with any therapeutics to serve as a control. In the case of mice instilled with doxycycline-nanowafer (FIG. 8B) and dexamethasone-nanowafer (FIG. 8C), the corneal surface was smooth and uniform, confirming that the controlled drug release from exemplary embodiments of the nanowafer of the present disclosure is effective in improving dry eye induced corneal epithelial disease. In comparison, the dry eye induced in mice administered twice a day with doxycycline and dexamethasone eye drops did not show as much improvement in smoothening of the corneal surface after 5 days. This study confirms that one single exemplary nanowafer instillation is very efficacious for 5 days or even more compared to several daily doses of eye drops.

Figure 9:
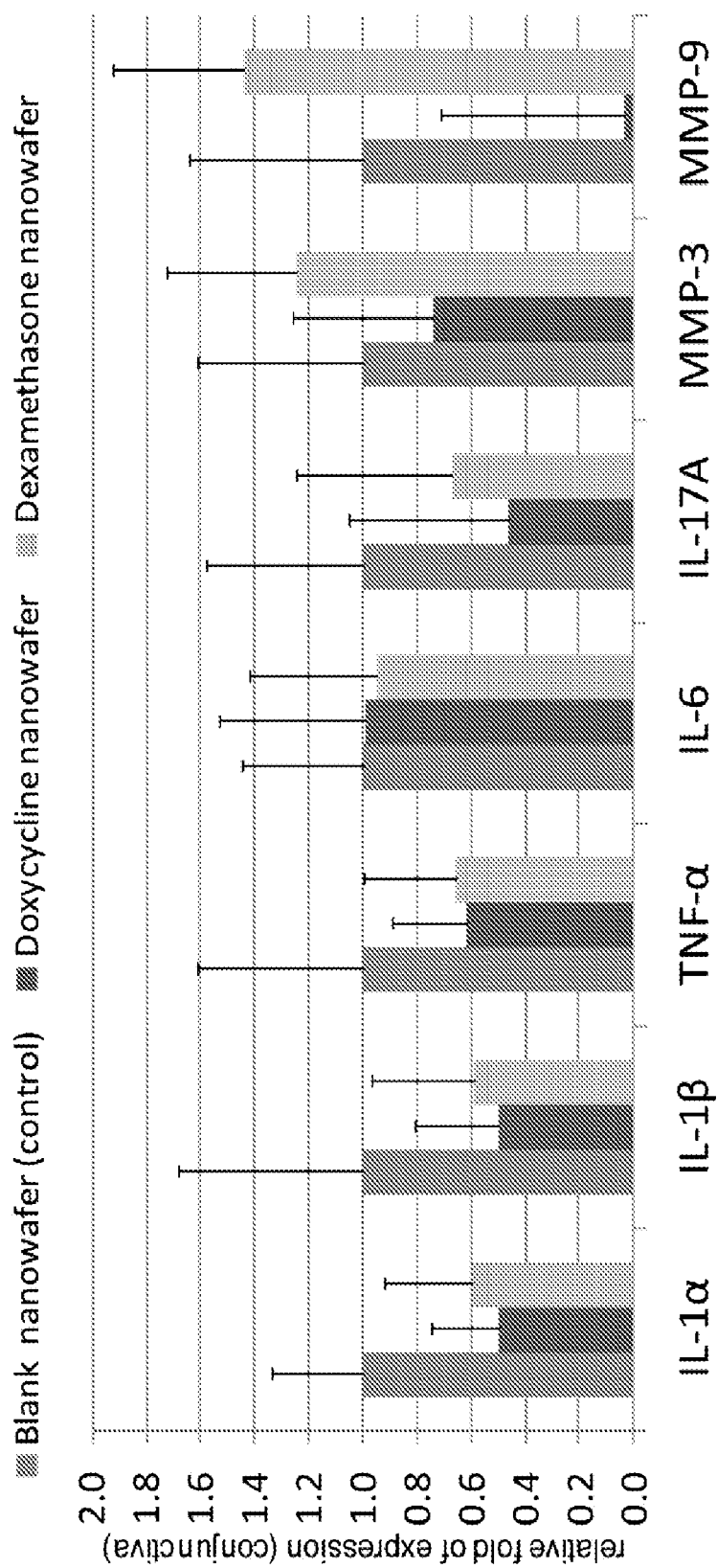
FIG. 9 is a graph showing gene expression analysis of pro-inflammatory cytokines, MMPs and IL-17A in certain mice treated with one embodiment of the therapeutics dispensing device of the present disclosure loaded with Doxocycline or Dexamethasone.

FIG. 9, shows the analysis obtained in another exemplary study of the effect of treatment with exemplary embodiments of the nanowafer of the present disclosure on gene expression of pro-inflammatory cytokines and matrix metalloproteinases (MMPs). Pro-inflammatory cytokines and MMPs have been found to be responsible for the altered corneal barrier function and surface irregularity in dry eye. Increased production and activation of pro-inflammatory cytokines (interleukin (IL)-1, tumor necrosis factor (TNF)-$\alpha$) and proteolytic enzymes by stressed ocular surface and glandular epithelial cells, as well as by the inflammatory cells that infiltrate these tissues have been reported in dry eye. These enzymes, such as MMP-9, lyse a variety of different substrates including components of the corneal epithelial basement membrane and tight junction proteins (such as ZO-1 and occludin) that maintain corneal epithelial barrier function. The increased MMP-9 activity in dry eye is associated with deranged corneal epithelial barrier function, increased corneal epithelial desquamation and corneal surface irregularity. As shown in FIG. 9, the study demonstrate that exemplary embodiments of dexamethasone or doxycycline-loaded nanowafers decreased expression of pro-inflammatory cytokines IL-1$\alpha$, IL-1$\beta$, TNF-$\alpha$ and matrix metalloproteinases (MMP)-3 and MMP-9 and the Th-17 signature cytokine, IL-17A. All inflammatory cytokines except IL-6 had reduced conjunctival expression in the dry eye groups that received exemplary embodiments of nanowafers containing either Doxy or Dexamethasone. These pilot studies had just a 50% chance to reach statistical significance but were useful to calculate sample size. Using a StateMate® software, an ideal sample size was calculated to be 12 animals per group. The following assumptions were made: a=0.05, a 50% difference in gene expression in IL-1$\alpha$ between the blank nanowafer and the doxycycline will be considered meaningful and the power will be ³90%.

EXAMPLES

The following paragraphs provide exemplary, non-limiting, embodiments of the therapeutics dispensing device of the present disclosure.

Example 1

Fabrication of Polyvinyl Alcohol Microwafers

A clear polyvinyl alcohol (PVA) solution (15% w/v in water, 5 ml) was transferred with a pipette onto a PDMS template (3" diameter) containing circular pillars (e.g., of 500 nm diameter and 500 nm height). The PVA solution was evenly spread to form a thin film completely covering the PDMS template and kept in an oven at 70° C. for 30 min. This step resulted in the formation of a thin and mechanically strong PVA template. The PVA template was peeled away from the PDMS template. The obtained PVA template was ~3" in diameter, contained circular wells (e.g., of 500 nm diameter and 500 nm depth). The PVA template was examined under a bright field reflectance microscope to determine its structural integrity.

Example 2

Fabrication of Polyacrylic Acid Microwafers

A clear polyacrylic acid (PAA) solution (10% w/v in ethanol, 5 ml) was transferred with a pipette onto a PDMS template (3" diameter) containing circular pillars (e.g., of 500 nm diameter and 500 nm height). The PAA solution was evenly spread to form a thin film completely covering the PDMS template and kept in an oven at 70° C. for 30 min. This step resulted in the formation of a thin and mechanically strong PAA template. The PAA template was peeled away from the PDMS template. The obtained PAA template was ~3" in diameter, contained circular wells (e.g., of 500 nm diameter and 500 nm depth). The PVA template was examined under a bright field reflectance microscope to determine its structural integrity.

Example 3

Fabrication of Polyhydroxyethylmethacrylate Microwafers

A clear polyHEMA solution (12% w/v in ethanol, 5 ml) was transferred with a pipette onto a PDMS template (3" diameter) containing circular pillars (e.g., of 500 nm diameter and 500 nm height). The PVA solution was evenly spread to form a thin film completely covering the PDMS template and kept in an oven at 70° C. for 30 min. This step resulted in the formation of a thin and mechanically strong polyHEMA template. The polyHEMA template was peeled away from the PDMS template. The obtained polyHEMA template was ~3" in diameter, contained circular wells (e.g., of 500 nm diameter and 500 nm depth). The polyHEMA template was examined under a bright field reflectance microscope to determine its structural integrity.

Example 4

Fabrication of Gelatin Microwafers

A clear gelatin solution (20% w/v in aqueous solution, 3 ml) at 50-55° C. was transferred with a pipette onto a silicon master template (3 in. diameter) containing circular pillars (e.g., of 500 nm diameter and 500 nm height). The gelatin solution was evenly spread to form a thin film completely covering the master template and cooled to 4° C. for 15 min by keeping it in a refrigerator. Cooling resulted in formation of a gelatin template which was subsequently peeled away from the master template. The obtained gelatin template was ~3 in. in diameter, and contained circular wells (e.g., of 500 nm diameter and 500 nm depth).

As provided, the present disclosure provides certain embodiments of a therapeutics dispensing device that can be configured to release a substance at the site of implantation or insertion as it dissolves in a predefined period of time. The therapeutics dispensing device of the present disclosure is particularly applicable to deliver therapeutics to the eye where it can be instilled on the eye (cornea or conjunctiva) or in the fornix with a fingertip (just like a contact lens) without any surgical procedure, which is not only very convenient but also most desirable. The therapeutics dispensing device of the present disclosure does not require surgery for implantation, does not introduce any discomfort to the patient, does not hinder or obstruct the eye sight of the patient, and does not require inconvenient excessive repeated dosage.

Fabrication of Drug-loaded Nanowafers

Embodiments provide polymer wafer patterned with nanoreservoirs filled with drug matrix. A useful aspect of the new approaches in this project is the use of a hydrogel template strategy that not only serves as a template for the fabrication of the nanowafer, but also functions as a stabilizing component for drug matrix for long term release. The key processing step in the approach is the use of a water-soluble polymer to fabricate nanowafers via the hydrogel template strategy (Acharya et al., 2011; Acharya, Shin, Vedentham, et al., 2010; Acharya, Shin, McDermott et al., 2010). Nanowafers are fabricated using the following polymers that are already in clinical use: PVA, dextran, carboxy methyl cellulose, polyvinylpyrrolidone, and (hydroxypropyl)methyl cellulose. From these, the best performing polymer-drug combinations may be selected. As a model system, fabrication of PVA nanowafer is described in detail herein.

Example 5

Fabrication of PVA Nanowafers

A clear PVA solution (10% w/v, 10 ml) is transferred with a pipette onto a silicon master template (3" diameter) containing square posts (e.g., of 500 nm×500 nm square and 500 nm high) placed on a spin coating system (SCS P6708 Spin Coater, Specialty Coating Systems). The spin speed is adjusted to 500 rpm and spun for 45 sec to obtain a 150 μm thick nanowafer. The concentration of the polymer solution, speed and time of a spin coater can be varied to obtain the required thickness of the nanowafer. After spin coating, the wafer is baked at 70° C. for 30 min and at the end of this period, the formed PVA nanowafer is carefully peeled away from the silicon wafer master template. The PVA nanowafer thus obtained is ~3" diameter and has nanoreservoirs of predefined dimensions (500 nm 500 nm×500 nm square and 500 nm deep). The nanowafer is characterized by bright field microscopy and FESEM to determine its structural integrity. Initial studies show that a solution of 15% polymer forms nanowafers that are mechanically strong enough to enable further processing.

Example 6

Filling the Reservoirs of the Nanowafer with Drug-PLGA Matrix

The nanowafer thus fabricated is filled with drug-PLGA solution by ultrasonic atomizer or by microinjection. For drug concentrations in the 1~5% range, the solution can be easily atomized by an ultrasonic atomizer. Filling the nanoreservoirs using an ultrasonic atomizer will form a thin film of excess drug-PLGA solution on the surface of the PVA nanowafer that can be removed by swiping the surface with a razorblade. In this process, using the right solvent is critical to prevent premature formation of a drug film by fast evaporation. For higher drug concentrations (5-20%), the solution is thick and the nanowafers are filled by microinjection. The concentration of the drug-PLGA solution (1-20%) can be adjusted to suit the required dosage and duration of release.

Example 7

In Vitro Release of Dexamethasone from Dex-nanowafer

In a typical study, Dex-nanowafers (1 cm×1 cm) are separately weighed into three 10 ml glass vials, and 5 ml of PBS/Tween-20 (pH 7.4) release medium is transferred into each vial. These vials are kept in an orbital shaker maintained at 37° C. with constant agitation. At 2 hour time intervals, 5 ml of the release medium is withdrawn from the vials and replaced with the same amount of the fresh medium. Thus collected samples are transferred into glass vials and stored in the refrigerator. Sampling of the release medium may be continued for 5 days. Each sample is filtered through a 0.5 μm syringe filter and subjected to HPLC analysis. In this study, a mixture of methanol (90%) and ammonium acetate (10%, pH 7) is used as a mobile phase after filtration through 0.22 μm membrane filter.

Example 8

Determination of Total Dexamethasone Content in Dex-nanowafers

The total amount of a dexamethasone loaded in the nanowafer is determined by dissolving an accurately weighed Dexamethasone-nanowafer (1 cm×1 cm) in 5 ml water, followed by addition of ethanol (9 ml). The precipitated PVA is removed by centrifugation. The clear solution is rotary evaporated and the solid formed is redissolved in the 10 ml of the mobile phase (90% methanol and 10% ammonium acetate, pH 7). An aliquot of this solution is filtered through a 0.5 μm syringe filter, analyzed by HPLC, and compared with the standard curve to quantify the content. This study may be performed in triplicate. From this study, the amount of dexamethasone per unit area of the nanowafer may be determined.

HPLC Analysis

HPLC experiments are performed on a Hitachi LaChrom-7000 HPLC system. The analytical column is X-Terra C-18 (250 mm×4.6 mm) from Waters. The system is equipped with auto sampler, in line degasser, and column oven set at room temperature. The mobile phase is a mixture of methanol (90%) and ammonium acetate (10%, pH 7), will be used after filtration through 0.22 µm membrane filter. Injection volume 65 µl flow rate was 1.0 ml/min and the pressure 1200 mm. Dexamethasone will be detected by UV absorption at 280 nm and the retention time is approximately 2.1±0.1 min. Dexamethasone concentration is calculated by comparing the peak area of standard and sample.

Accuracy and Precision

Accuracy and precision are assessed using 200 µg/ml concentration of dexamethasone. At the beginning and end of each set of studies conducted, replicate samples are evaluated. For accurate and precise method % RSD (Relative standard deviation) is less than 2.0%, in at least certain aspects.

Linearity of the Standard Curve of Dexamethasone Concentrations

Linearity study is performed by single measurement of dexamethasone solutions of a series of concentrations in increasing order from the limit of quantification. The obtained data is treated statistically for calculation of regression coefficient ($R^2$). Under most circumstances $R^2$=0.999. The linear range of detection that obeys Lambert Beer's Law is dependent on the drug analyzed and detector used. The $R^2$ value for drug in the concentration range of 0.5 µg/ml and 50 µg/ml is calculated. The standard curve shows a perfect linearity between 1 and 50 µg/ml concentrations of Dexamethasone, in at least certain aspects.

Example 9

Drug Stability Analysis

The dexamethasone-loaded nanowafer was analyzed at different time intervals to assess any change in peak area of drug whilst the solution is protected from physical and chemical stress. For this study 28 dexamethasone nanowafers (1 cm×1 cm) were kept in refrigerated condition and analyzed at 24 hr intervals for 28 days. HPLC analysis revealed that Dexamethasone in PBS/Tween-20 is stable for 28 days as no additional peaks, besides dexamethasone were observed.

Example 10

Collection of Mouse Tear Fluid Washings

Tear fluid washings are collected by a previously reported method (Grass et al., 1988). Briefly, 1.5 µL of PBS containing 0.1% bovine serum albumin (BSA) is instilled into the conjunctival sac. The tear fluid is collected with a 1 µL volume glass capillary tube (Drummond Scientific Co., Broomhall, Pa.) by capillary action from the tear meniscus in the lateral canthus. The tear washings are stored at −80° C. until tear assays are performed. For oregon green dextran loaded nanowafers, the concentration in tear washings are compared to a standard curve of oregon green dextran (from 50 µg/µl). The drug release from dexamethasone nanowafers into tears is measured using Dexamethasone standard curves.

Example 11

Creation of Dry Eye in Mice by Cholinergic Receptor Blockade and Desiccating Environment The desiccating stress (DS) mouse model of dry eye is created as previously reported. Subcutaneous injections of 2.5 mg/mL scopolamine hydrobromide, (Sigma-Aldrich, St. Louis, Mo.) is given in alternating flanks 4 times per day (Cho et al., 2012; Gayton, 2009). Female C57BL/6 aged 6-8 weeks will be placed in specially designed cages with screens on both sides then placed 6 inches in front of a fan located in a chamber for 16 hours per day for 5 or 10 days. The room humidity is maintained at or below 30%.

Example 12

Evaluation of In Vivo Efficacy of Drug-nanowafers in Dry Eye Induced Mice

In vivo efficacy of nanowafers is evaluated in the murine dry eye model using anti-IFN-γ that has been found to inhibit corneal and conjunctival epithelial apoptosis (Cho et al., 2012; Gayton, 2009). Prior to induction of dry eye, mice are anesthetized with Avertin and a 2 mm circular nanowafers are applied to the inferior bulbar conjunctiva adjacent to the fornix using forceps. The nanowafers adhere to the conjunctiva and do not move with blinking. After anesthesia recovery, DS is induced as described above. Control mice receive no ocular topical treatment. Efficacy parameters include conjunctival goblet cell density, goblet cell mucin MUC5AC expression and markers of apoptosis (TUNEL and activated caspase 3 staining) in cornea and conjunctival tissue sections and lysates (caspase 3 activity) obtained after 10 days of DS. Nanowafers containing 1 mg/ml of anti-IFNγ are initially evaluated, and higher or lower concentrations are evaluated based on the biological response.

Control Study

Another group of dry eye mice receive blank nanowafers as a control for dexamethasone or rat IgG, 1 mg/mL (Vector Laboratories) as a control for anti-IFN-γ to assess the effects of the nanowafer material alone on development of dry eye induced ocular surface disease. The blank and IgG-loaded nanowafers are prepared by the same methodology as the drug-loaded nanowafers. The efficacy measures used for the drug-loaded groups are evaluated and results compared with those obtained from drug-nanowafer treatment.

Example 13

Topical Treatment of Dry Eye Induced Mice with Eye Drops

Groups of dry eye mice are treated with dexamethasone 0.1% or anti-IFNγ eye drops (10 µL of anti-IFNγ hybridoma-1 mg/mL, R4-6A2; catalog no. HB-170; American Type Culture Collection, Rockville, Md.) twice a day for 10 days. The same GC and apoptosis markers assessed in the nanowafer treated groups are evaluated at 10 days.

Example 14

An Example of Efficacy Parameters

Periodic Acid Schiff Staining and Goblet Cell Measurement

Enucleated mouse eyes are fixed in 10% formalin, and embedded in paraffin. Ocular sections are cut at the center of the eye, where the lens has its maximum diameter. Sections are stained with periodic-Schiff (PAS) reagent for measuring goblet cell density and examined and photographed with a microscope equipped with a digital camera (Eclipse E400 with a DS-Fi1; Nikon). The number of goblet cells in the superior and inferior conjunctiva are measured in 3 sections from each eye that are 300 mm apart, using image-analysis software (NIS Elements Software, version 3.0, BR, Nikon) and expressed as number of goblet cells/mm.

MUC5AC ELISA

A commercially available mouse MUC5 subtype AC ELISA kit may be used to measure the concentration of MUC5AC protein in conjunctival lysates. The results are normalized by protein concentration of the lysate. There is an excellent correlation between the level of MUC5AC protein and conjunctival goblet cell density measured in histologic sections in the mouse dry eye model.

Assessment of Ocular Surface Epithelial Apoptosis

TUNEL Assay and Caspase-3 Immunostaining

The TUNEL assay is performed using a commercially available kit (ApopTag; Intergen Co, Purchase, N.Y.). Cryosections stained for activated caspase-3 (5 g/mL; BD Pharmingen), caspase-8 (neat serum, 1:100; Novus Biologicals, Littleton, Colo.), and caspase-9 (neat serum, 1:100; Novus Biologicals) is developed using goat anti-rabbit Alexa-Fluor 488-conjugated antibody. Negative controls performed at the same time consist of sections incubated with PBS in place of primary antibody. Digital images (512×512 pixels) of representative areas of the central cornea and goblet cell rich area of the conjunctiva are captured with a laser scanning confocal microscope (Zeiss, Thornwood, N.Y.). The intensity of the staining is measured using NIS Elements (Nikon).

Fluorometric Assays for Activated Caspases 3, 8, and 9

The activity of caspases 3, 8, and 9 is measured in corneal epithelium and conjunctival biopsies according to the protocol provided by the manufacturer of their respective fluorometric kits (Biovision K105-25, K112-25, and K189-100, respectively). Corneal epithelium are scraped and conjunctiva surgically excised and placed in the lysis buffer provided with the kits. Protein concentration of lysates is measured using a Micro BSA protein assay kit (Thermo Fisher Scientific, Austin, Tex.), and 50 µg of corneal/conjunctival lysate is used for each assay. Lysis buffer without any protein serves as a blank control. Five samples per group/strain are used, and each sample consists of pooled corneal or conjunctival samples from four mice. Fluorescence is read using a Tecan Spectra Fluorophotometer with 400-nm excitation and 505-nm emission filters.

TUNEL and MUC5AC Immunostaining

TUNEL assay is performed using a commercially available kit (ApopTag; Intergen Co., Purchase, N.Y.). Cryosections are fixed in 1% paraformaldehyde and permeabilized with 2:1 ethanol/acetic acid solution. The samples are incubated with TdT enzyme and 11-digoxigenin dUTP at 37° C. for 4 hours. After quenching the reaction, samples are blocked with blocking solution and incubated with anti-digoxigenin FITC-conjugated antibody for 60 mins at room temperature. After completion of the initial TUNEL procedure, the cryosections are stained for expression of MUC5AC (rabbit anti-MUC5AC primary antibody; 1:100, sc-20118; Santa Cruz Biotechnology), as described. Digital images (512×512 pixels) of representative areas of the tarsal conjunctiva are captured, and the TUNEL-positive cells in the conjunctival epithelia in 200 µm length segments are counted.

Example 15

Controlled Release Cysteamine Nanowafer for Treating Corneal Cystinosis

Figure 20:
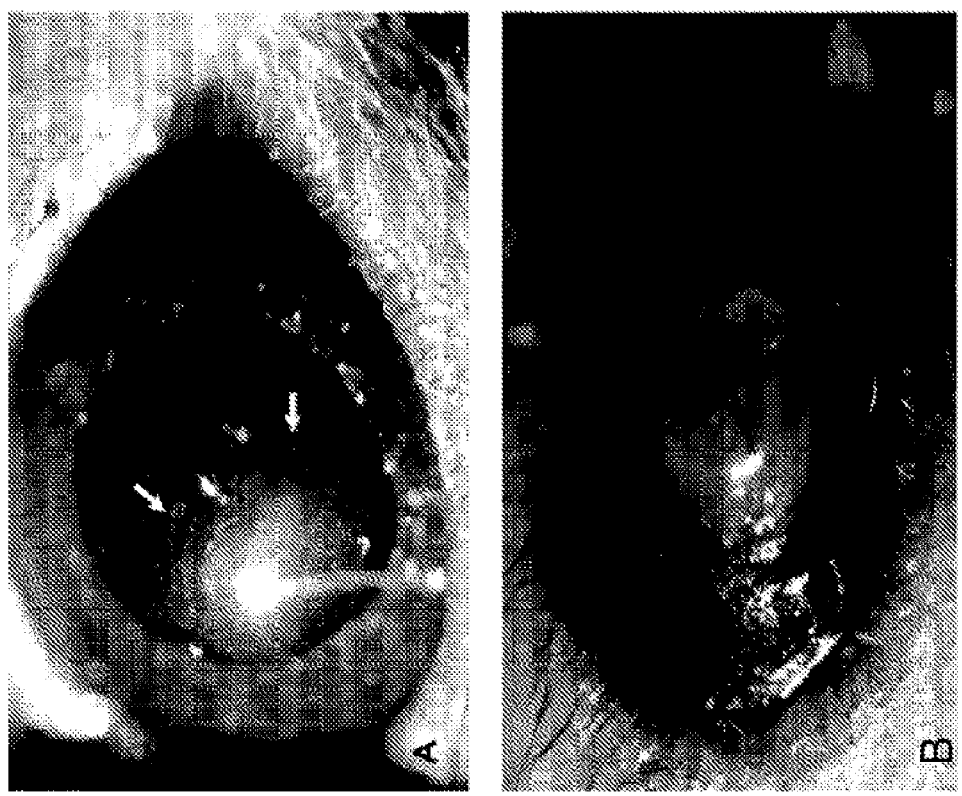
FIGS. 20A-20B show corneal crystal growth progression in cystinosin (Ctns$^{-/-}$) mouse model.
Figure 21:
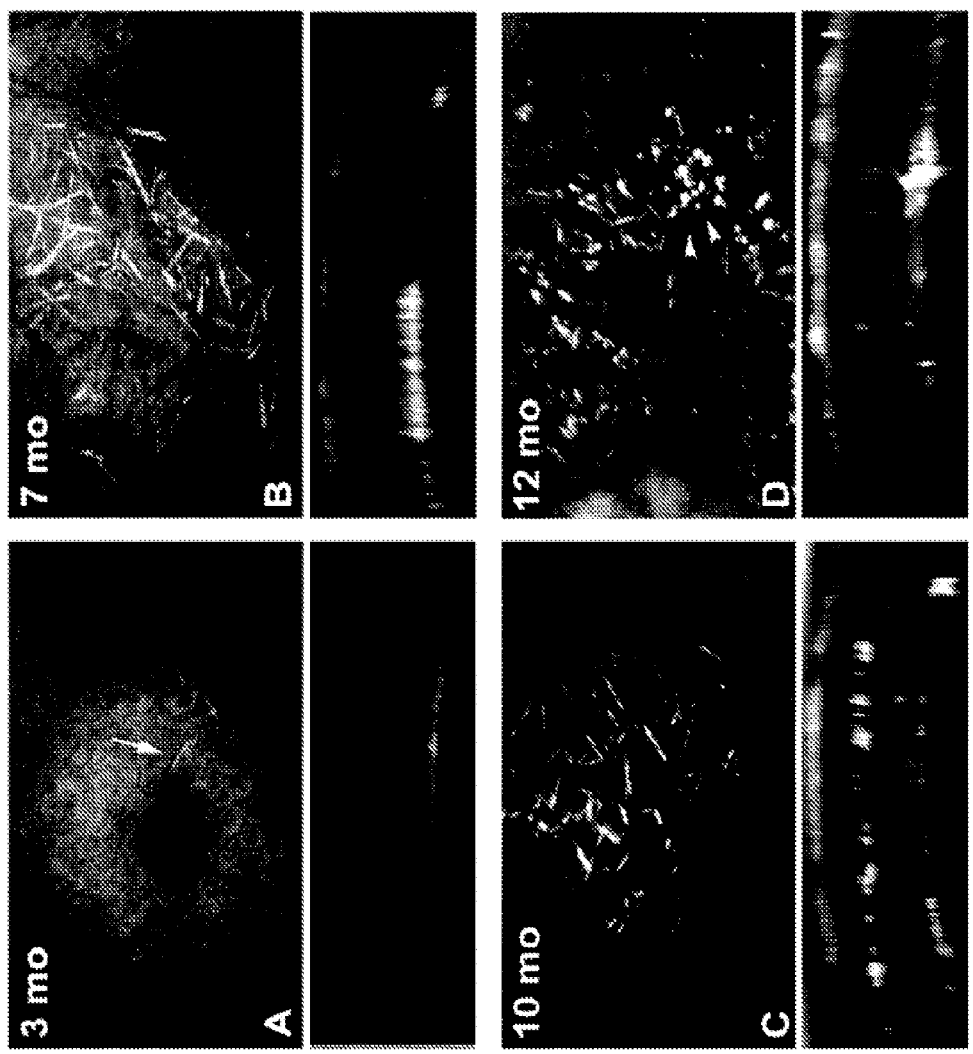
FIG. 21 demonstrates corneal Cystinosis in Ctns$^{-/-}$ Mouse: (A) at 3 months, highly reflective needle shaped crystals in posterior central/peripheral stroma; (B) At 7 months, more abundant needle-shaped crystals in mid posterior central/peripheral stroma; (C) at 10 months: crystals shorter, thicker; posterior and anterior stroma; and (D) at 12 months, Crystals are more punctate and fewer needle-shaped.

Cystinosis is an autosomal recessive lysosomal storage disease characterized by accumulation of cystine crystals in various tissues, including kidney, thyroid, brain and eye. The disease has been linked to mutations in the CTNS gene (17p13) that codes for cystinosin, a trans-membrane protein that is responsible for transport of the disulfide cystine amino acid out of the lysosome. Different CTNS mutations are associated with a spectrum of clinical disease, however corneal crystals are present in all forms of the disease. (FIGS. 20 & 21).

Oral cysteamine (HS-CH2-CH2-NH3) has been the mainstay of therapy for over 20 years. A free thiol group in cysteamine reacts with cystine to produce the single sulfide amino acid cysteine, plus a cysteine-cysteamine mixed disulfide, thereby circumventing the transporter defect. Oral cysteamine has significantly improved overall prognosis, but no improvement in ocular manifestations of the disease have been demonstrated with systemic treatment. Topical cysteamine applied every hour is effective in reducing corneal crystals, but is impractical due increased inflammation, redness and other side effects, leading to poor compliance. Progressive photophobia, recurrent corneal erosions and visual deterioration associated with increasing concentrations of corneal crystals have therefore become the major long-term burden for individuals suffering from corneal cystinosis. In this present example, the development of a nanowafer drug delivery system that can overcome shortcomings of conventional eye drop formulations and release cysteamine for an extended period of time (1-7 days) is described.

Exemplary polyvinyl alcohol (PVA) nanowafers containing 500 nm diameter wells were filled with cysteamine and cysteamine-PLGA matrix. Thus fabricated nanowafers were tested for in vivo efficacy in Cystinosin (Ctns−/−) knockout mice. The potential corneal toxicity (corneal stromal opacity, corneal neovascularization or corneal epithelial changes) of the cysteamine nanowafer in mouse corneas was evaluated by testing five cysteamine concentrations in the nanowafers: 500, 200, 100, 50 and 0 ng/wafer (0=blank wafer). 25 CTNS$^{+/-}$ mice ages 3-5 months were divided into 5 groups with 5 animals per group. A cysteamine nanowafer was applied to the right cornea of each animal every third day for one week. No visible corneal toxicity was noted in blank wafers, or at 50 or 100 ng/wafer doses. At day four, 50% of the 500 ng/wafer corneas displayed corneal stromal opacity and at day seven 100% displayed stromal opacity. For the 200 ng cysteamine/wafer group, one cornea displayed subtle questionable corneal opacity at Day 7 (FIG. 22).

Figure 23:
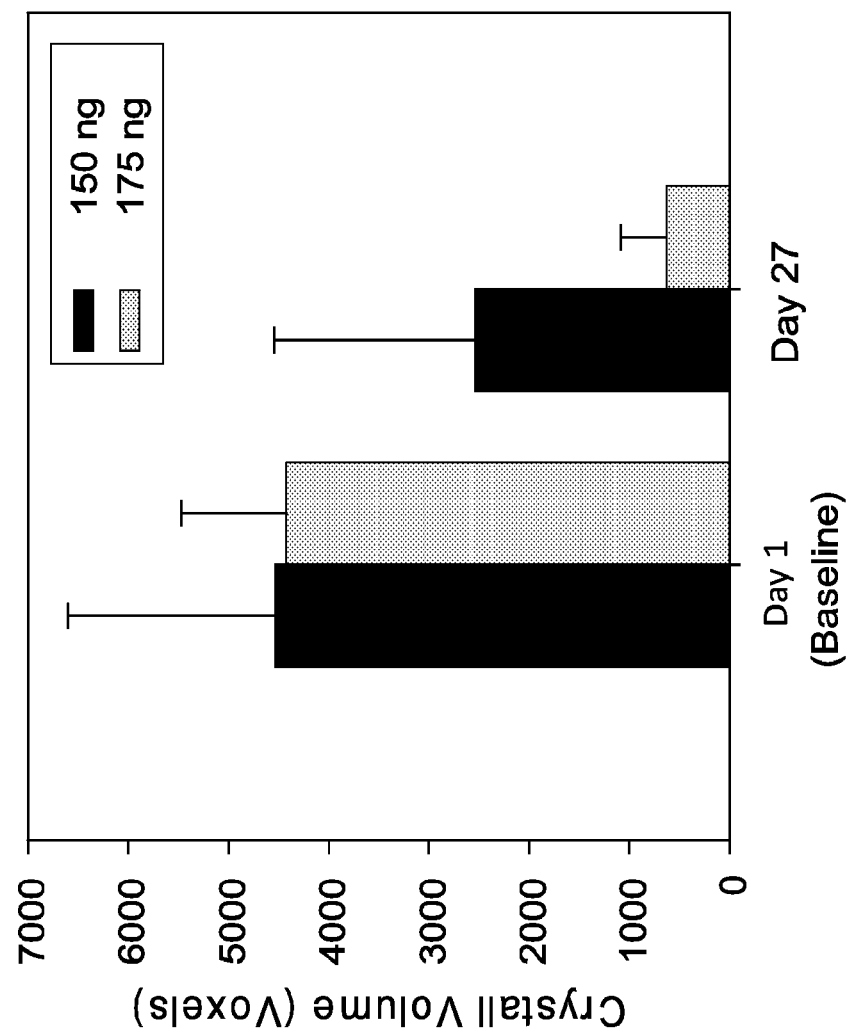
FIG. 23 provides cysteamine nanowafer efficacy in cystinosis knockout mice.
Figure 24:
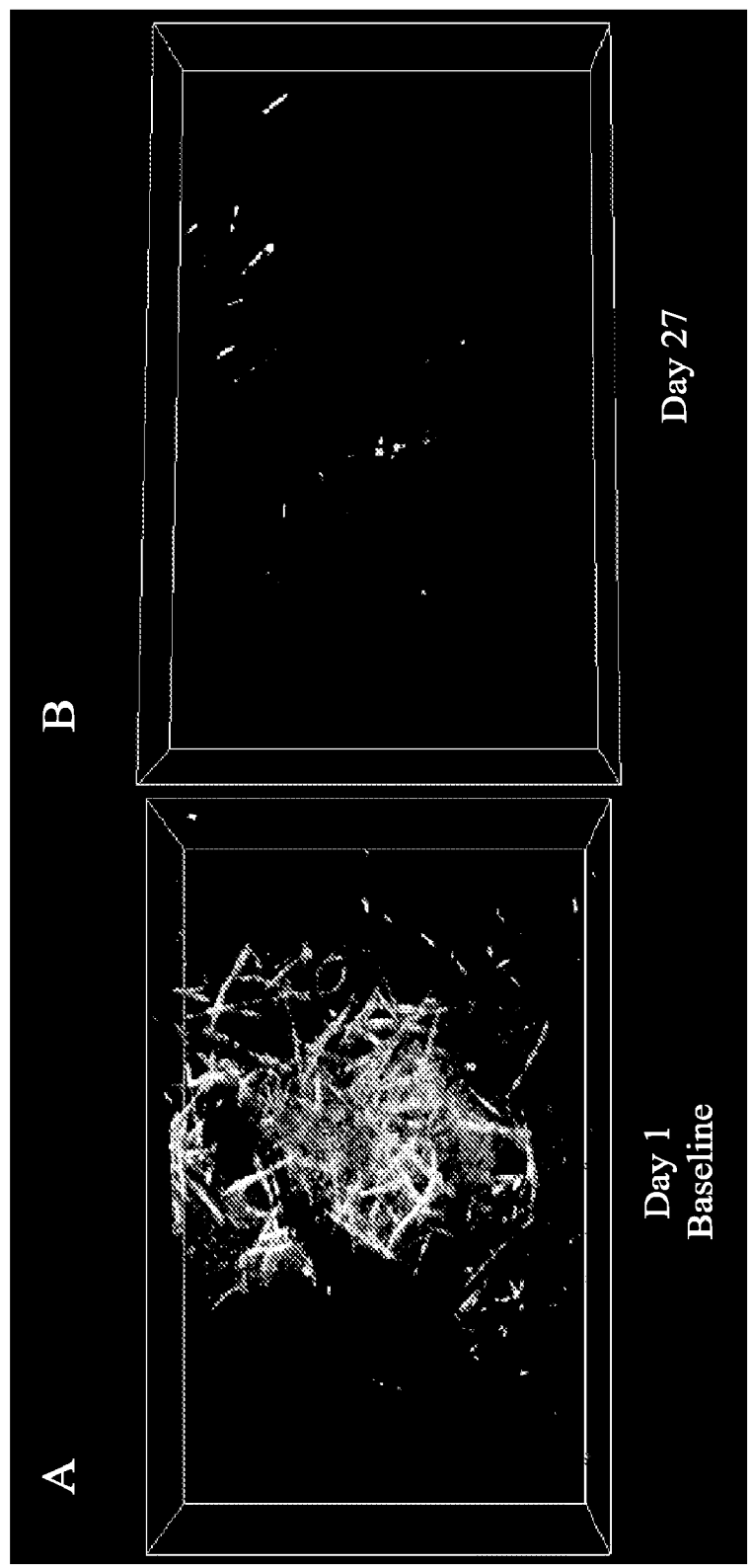
FIG. 24 shows in vivo Cysteamine-nanowafer efficacy in cystinosis knockout mice. Confocal fluorescence imaging demonstrating: (A) At day 1: there is maximum crystal density; (B) treatment with cysteamine loaded nanowafer, once every 4 days, has dissolved most of the crystal in 27 days.

Based on these results, nanowafers with cysteamine concentrations of 150 and 175 ng/wafer to evaluate the effect on corneal crystal concentration (FIG. 22). Seven month-old CTNS$^{-/-}$ mice were divided into two groups of 5. Baseline corneal cystine crystal volume was quantified using in-vivo confocal microscopy at time zero in the right eye of each animal. A cysteamine nanowafer of either 150 or 175 ng/wafer was placed on the right eye every third day for 27 days. At day 27 corneal crystal volume was re-measured using in-vivo confocal microscopy. The results demonstrated a drastic reduction (~90%) in the corneal crystal volume resulting in a significantly enhanced efficacy of the nanowafers compared to cysteamine hourly administrated cysteamine eye drops (FIGS. 23 and 24).

Example 16

Controlled Release Nanowafer for Ocular Burn Injury

Chemical and thermal injuries to the surface of the eye have a high potential to cause blindness. These injuries often damage the epithelium covering the cornea, conjunctiva, and eyelid margins and in more severe cases destroy the stem cells that renew these epithelia. An alkali burn to the cornea is a serious problem that may cause severe and permanent visual impairment. In many cases, the supporting stromal cells and matrix are damaged and chronic inflammation is induced. The influx of inflammatory cells (monocytes/macrophages, neutrophils), activation of corneal cells (mainly keratinocytes), and epithelial cells, and subsequent stromal neovascularization are involved in the post-alkali tissue damage in the cornea (Saika et al., 2005). Furthermore, most patients with severe ocular surface injuries develop a secondary dry eye due to destruction of tear producing cells which worsens the outcome. In addition to lubricating the ocular surface, the tears contain numerous growth and anti-inflammatory factors that are essential for wound repair and suppressing inflammation and tissue destruction. The immediate or acute phase occurs at the time of the injury and results in corneal and conjunctival epithelium damage or necrolitic death and chemical invasion into stroma, the anterior chamber, the ciliary body, and the iris. The later phases of eye burns (intermediate and chronic) occur over the subsequent days to months and require medical and surgical management by ophthalmologic and plastic surgery specialists to control the robust inflammatory and wound healing response to the injury.

Ocular surface trauma induces release/activation of metalloproteinases: It has been recognized for decades that ocular surface chemical/thermal injury stimulates production of tissue degrading enzymes as part of the wound healing cascade (Sosne et al., 2005, Takahashi et al., 2007). Matrix degrading enzymes, including metalloproteinases (MMPs) have been identified as important factors in the inflammatory and wound healing response of the ocular surface, particularly in dry eye and ocular burns. Their induction during wound healing is thought to play a role in extracellular matrix remodeling, cytokine activation, and regulation of angiogenesis (Corrales et al. 2006). The MMP family includes more than 25 members that can be divided into collagenases that degrade fibrillar collagen types I, II, and III (MMP-1,-8,-13); gelatinases that degrade collagen types IV, V, and VII and X as well as decorin, fibronectin, and laminin, that are found in basement membranes (MMP-2, -9); stromelysins (MMP-3, and -10); matrilysins that degrade proteoglycans, laminin, and glycoproteins (MMP-7 and -26); and the membrane-type MMPs that are bound to epithelial cell membranes, and can activate MMPs, according to their structure and substrate specificity (MMP-14, to -17 and -24).[9-12] Collectively they are able to degrade the entire extracellular matrix and basement membranes components. Barely detected in an unwounded cornea, MMPs are strongly induced during wound healing. Among these, MMP-9 play a prominent role being produced by stressed cornea and conjunctival epithelial cells and has both matrix degrading and pro-inflammatory activities (Fini et al, 1992; Matsubara et al., 1991).

New treatment strategies for ocular injuries are necessary: Therapeutic strategies for ocular surface chemical/thermal injuries have been directed towards promoting epithelial healing and suppressing inflammation and tissue destruction, during the acute phase (Reim et al., 2001). Treatment of the chronic phases, including the anatomical sequelae, sometimes requires a multi-disciplinary approach and very often, surgical procedures, such as amniotic transplantation or stem cell transplantation.[28] Although these approaches have slightly improved visual outcomes, the visual outcomes from these injuries still remain poor in large part due to inadequate control of inflammatory and proteolytic components of the wound healing response.

Need for the development of nanowafer ocular drug delivery systems: Delivery of therapeutic agents to the eye in the form of eye drops is by far the most effective mode of treatment. Although this is a very simple mode of drug delivery, the drug is available only for a short period of time (~30 mins), and most of the drug will be lost from the corners of the eye or by absorption into the draining ducts into the nose. Localized delivery can also be achieved by using eye drop suspensions containing drug loaded particles. Micro-/nanoparticle-based delivery systems are easy to prepare, but exhibit certain limitations: (a) low drug loading; (b) burst drug release kinetics; (c) clumping of the nano-/microparticles in the eye potentially leading to infections; and (d) growth of scar tissue around these clumps leading to cyst formation. Hence there is a strong need for the development of programmable drug delivery systems with high drug content and long term drug release attributes.

A controlled release nanowafer drug delivery system for the long-term administration of anti-inflammatory agents would be a major advance in the management of the blinding eye injuries and infections. Development of a nanowafer drug delivery device that can serve as a controlled release drug delivery system, provide mechanical barrier to protect the eye from infections, and fade away (biodegrade/dissolve) is most desired. Although there are several bandage contact lenses in the market, there is no device presently available that can effectively perform these functions. To address these issues, we have developed a nanowafer drug delivery systems and evaluated its efficacy in ocular burn mouse model.

Figure 25:
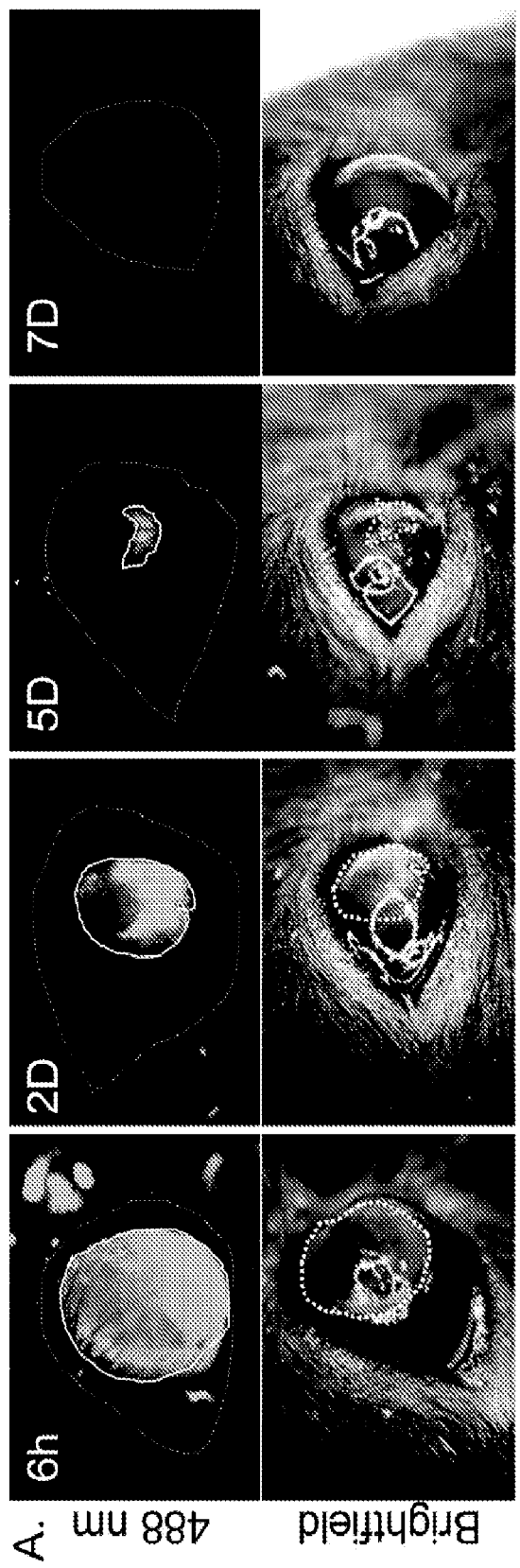
FIG. 25. (A) Representative digital images of eyes subjected to both ocular burn+desiccating stress. 3 mm-diameter doxycycline-loaded nanowafers were applied to the surface of the ocular burn. Images taken from 6 hours (h) to 7 days (D) after the initial lesion. Doxycycline is auto fluorescent under 488 nm excitation. Note decreasing size of nanowafer autofluorescence in top panel (circumscribed by solid white line) over time. Red line delineates the lid margin. Bottom panel shows the same eye photographed under bright field conditions. Dotted line shows the nanowafer membrane. (B) Mean±standard deviation of intensity (gray levels)/mm$^2$ of doxycycline-nanowafer membranes measured on the cornea at the same time points as images in A.
Figure 25:
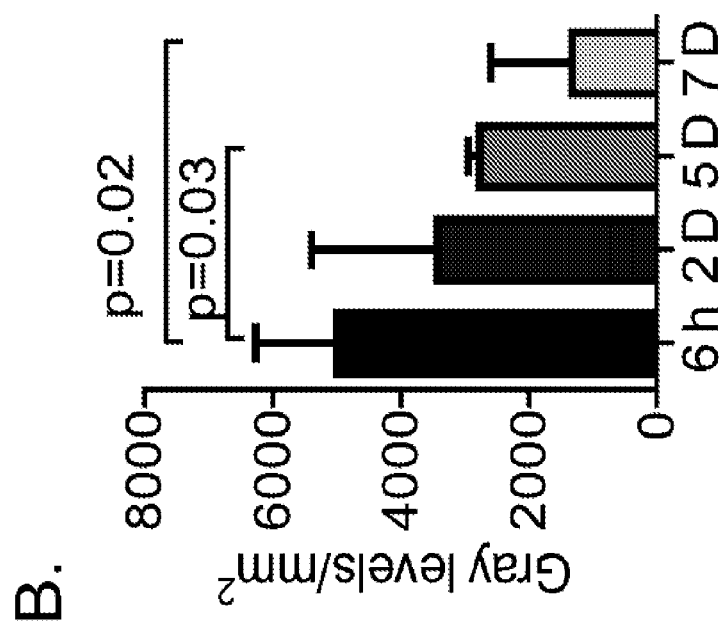

Drug release in vivo from the nanowafer: Using a fast (3-5 days) degradable doxycycline nanowafer, we performed sequential imaging of eyes from 6 hours to 7 days after the placement of the nanowafer. Intensity of autofluorescence of doxy-nanowafer was measured in digital images by delineating the total area occupied by the microwafer and the results averaged within the group. Our results are shown in FIG. 25, where the initial dissolution of a 3-mm doxy-nanowafer can be seen at 6 hours after placement and its disappearance over a period of 7 days. Autofluorescence is inversely proportional to the drug content in the nanowafer.

Figure 26:
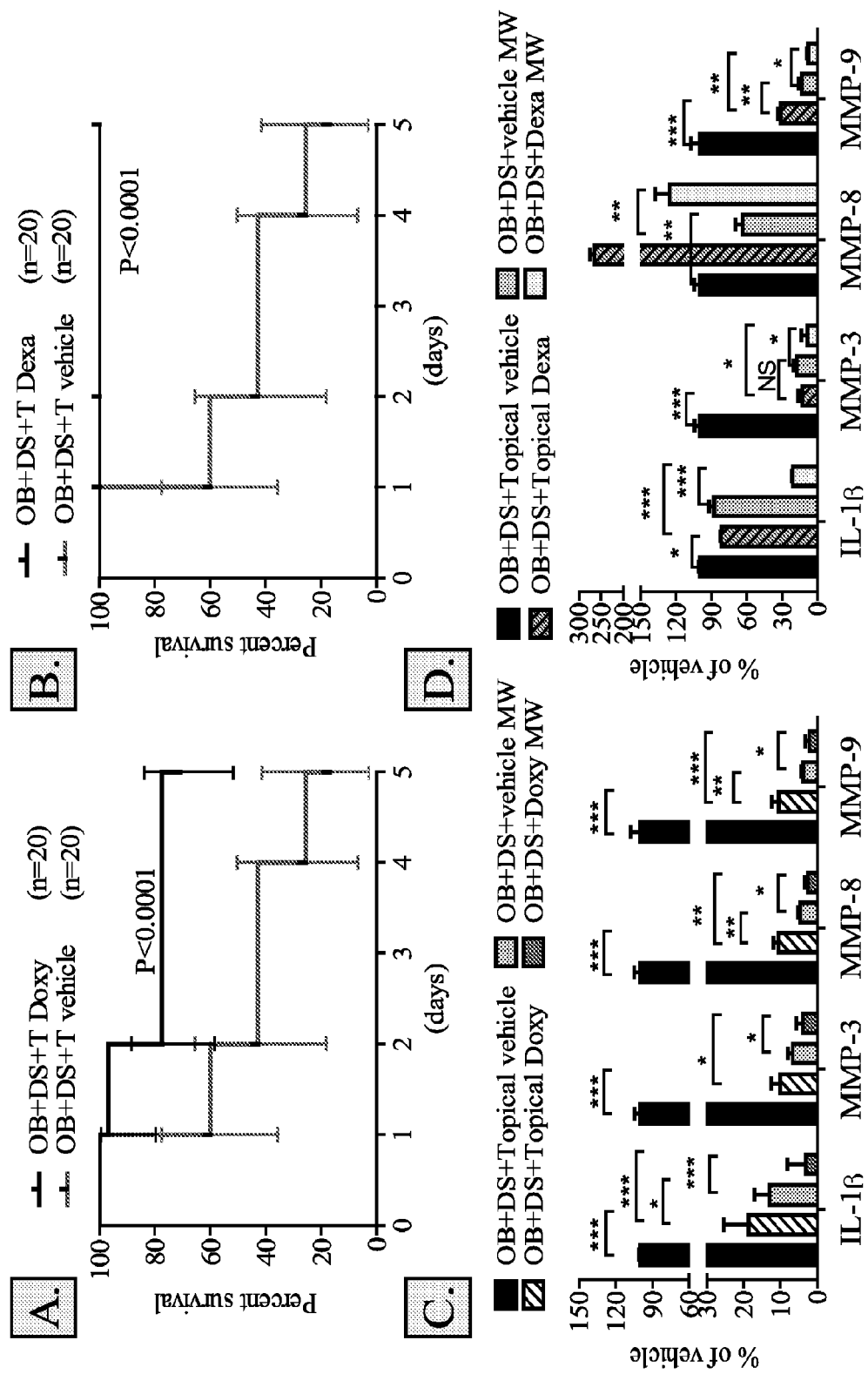
FIGS. 26. A and 26B demonstrate rate of ocular perforation in eyes subjected to ocular burn (OB) with concomitant desiccating stress (DS) treated either with topical (T) doxycycline (Doxy, in A), Dexamethasone (Dexa, in B) or its vehicle. C&D. Gene expression of inflammatory cytokines and MMPs in corneas subjected to ocular burn (OB)+ desiccating stress (DS) topically treated with either Doxycycline (in C) or Dexamethasone (in D) loaded–microwafer (MW).*p<0.05; P<0.01,*P<0.001; NS=non-significant.

Topical treatment with either doxycycline or dexamethasone significantly changes the fate of corneas subjected to OB+DS: Corneas subjected to conventional topical doxycycline eye drops four times/day had significantly lower number of corneal perforations and significantly decreased IL-1β, MMP3,-8,-9 expression after 2 days of initial insult (FIG. 26). These results indicate that early therapy is mandatory in the management of ocular injuries.

Nanowafers work as contact bandage lens: Our results show that use of nanowafer with PVA vehicle offers further protection than conventional eye drops (FIG. 25B) due to mechanical barrier, protecting the healing epithelium of proteases and inflammatory cytokines in the ocular surface.

These results indicate a further advantage of using the nanowafer-loaded drugs than conventional eye drop therapy.

Doxycycline or dexamethasone-loaded microwafers further decreases gene expression of corneas subjected to OB+DS when compared to topical drugs. Drug-loaded nanowafer provide further protection to the corneas subjected to OB+DS by further decreasing expression of inflammatory/protease mediators when compared to topical treatment of vehicle microwafer (FIGS. 25C and 25D).

Although the present disclosure and its advantages have been described in detail, it should be understood that various changes, substitutions and alterations can be made herein without departing from the spirit and scope of the disclosure as defined by the appended claims. Additionally, the methods and apparatus taught by this disclosure have clear and obvious application in the field of hydrogenation of minerals and fluids in-situ. Moreover, the scope of the present application is not intended to be limited to the particular embodiments of the process, machine, manufacture, composition of matter, means, methods and steps described in the specification. As one of ordinary skill in the arts will readily appreciate from the disclosure of the present disclosure, processes, devices, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, devices, manufacture, compositions of matter, means, methods, or steps.

REFERENCES

The following publications are herein incorporated by reference to the same extent as if each individual publication was specifically and individually indicated to be incorporated by reference.

Acharya G, McDermott M, Shin S J, Park H, Park K. Hydrogel Templates for the Fabrication of Homogeneous Polymer Microparticles. Biomedical Nanotechnology, *Methods Mol Biol.* 2011; 726:179-185.

Acharya G, Shin C S, McDermott M, Mishra H, Park H, Kwon I C, Park K. The hydrogel template method for fabrication of homogeneous nano/micro particles. *J. Control. Release.* 2010; 141:314-319.

Acharya G, Shin C S, Vedantham K, McDermott M, Rish T, Hansen K, Fu Y, Park K, A Study of Drug Release from Homogeneous PLGA Microstructures. *J. Control. Release.* 2010; 146:201-206.

Afonso A A, Sobrin L, Monroy D C, Selzer M, Lokeshwar B, Pflugfelder S C. Tear fluid gelatinase B activity correlates with IL-1alpha concentration and fluorescein clearance in ocular rosacea. *Invest Ophthalmol Vis Sci.* 1999; 40:2506-2512.

Ahmed I, Gokhale R D, Shah M V, Patton T F. Physicochemical determinants of drug diffusion across the conjunctiva, sclera. and cornea. *J. Pharm. Sci.* 1987; 76, 583-586.

Ahmed, I. et al. (1987) Disposition of timolol and inulin in the rabbit eye following corneal versus noncorneal absorption. Int. J. Pharm. 38, 9-21.

Alonso, M. J. et al. (1989) New ophthalmic drug release systems: formulation and ocular disposition of amikacin-loaded nanoparticles. 5th Int. Conf. Pharm. Tech. 1, 77-83.

Araki K, Ohashi Y, Kinoshita S, Hayashi K, Kuwayama Y, Tano Y: Epithelial wound healing in the denervated cornea. Curr Eye Res. 1994, 13:203-211.

Avunduk A M, Avunduk M C, Varnell E D, Kaufman H E. The comparison of efficacies of topical corticosteroids and nonsteroidal anti-inflammatory drops on dry eye patients: a clinical and immunocytochemical study. *Am J Ophthalmol.* 2003; 136:593-602.

Azar D T. Corneal angiogenic privilege: angiogenic and antiangiogenic factors in corneal avascularity, vasculogenesis, and wound healing (an American Ophthalmological Society thesis). Trans Am Ophthalmol Soc. 2006; 104:264-302.

Bausch&Lomb, Fluocinolone acetonide ophthalmic—Bausch & Lomb: fluocinolone acetonide Envision T D implant. Drugs R D, 2005. 6(2): p. 116-9.

Bausch&Lomb, http://www.retisert.com/professional_home.html

Bochot, A. et al. (1998) Liposomes dispersed within a thermosensitive gel: a new dosage form for ocular delivery of oligonucleotides. Pharm. Res. 15, 1364-1369.

Borchardt R T. Assessment of transport barriers using cell and tissue culture systems. *Drug. Dev. Ind. Pharm.* 1990; 16:2595-2612.

Brechue W F, Maren T H. pH and drug ionization affects ocular pressure lowering of topical carbonic anhydrase inhibitors. *Invest. Ophthalmol. Vis. Sci.* 1993; 34:2581-2587.

Burns A R, Li Z, Smith C W. Neutrophil migration in the wounded cornea: The role of the keratocyte. Ocular Surface 2005; 3:S-173-S-176.

Byeseda S E, Burns A R, Dieffenbaugher S, Rumbaut R E, Smith C W, Li Z. ICAM-1 is necessary for epithelial recruitment of gammadelta T cells and efficient corneal wound healing. Am J Pathol 2009; 175:571-9.

Cadman, J., *Ganciclovir implants: one year later*. GMHC Treat Issues, 1997. 11(4/5): p. 3-6.

Chang E, McClellan, A J, Farley W J, Li D-Q, Pflugfelder S C, De Paiva, C. Biodegradable PLGA-based drug delivery systems for modulating ocular surface disease under experimental murine dry eye. J Clinic Experiment Ophthalmol. 2011; 2:191. doi:10.4172/2155-9570.1000191

Chang J H, Gabison E E, Kato T, Azar D T. Corneal neovascularization. Curr Opin Ophthalmol. 2001; 12:242-249.

Cho, Y. K., Uehara, H., Young, J. R., Archer, B., Zhang, X. and Ambati, B. K. (2012) 'Vascular endothelial growth factor receptor 1 morpholino decreases angiogenesis in a murine corneal suture model', *Investigative ophthalmology & visual science* 53(2): 685-92.

Choy Y B, Park J-H, McCarey B E, Edelhauser H F, Prausnitz M R. Mucoadhesive microdiscs engineered for ophthalmic drug delivery: effect of particle geometry and formulation on preocular residence time. *Invest Ophthalmol Vis Sci.* 2008; 49:4808-4815.

Chrai S S, Patton T F, Mehta A, Robinson J R. Lacrimal and instilled fluid dynamics in rabbit eye. J. Pharm. Sci. 1973; 62:1112-1121.

Ciolino J B, Hudson S P, Mobbs A N, Hoare T R, Iwata N G, Fink G R, Kohane D S. A prototype antifungal contact lens. *Invest Ophthalmol Vis Sci.* 2011; 52: 6286-629.

Condeelis, J. and Pollard, J. W. (2006) 'Macrophages: obligate partners for tumor cell migration, invasion, and metastasis', *Cell* 124(2): 263-6.

Corrales R M, Stern M E, de Paiva C S, Welch J, Li D Q, Pflugfelder S C. Desiccating stress stimulates expression of matrix metalloproteinases by the corneal epithelium. *Invest Ophthalmol Vis Sci.* 2006; 47:3293-3302.

Craig, J. Structure and function of the preocular tear film. In *The tear film*; Korb, D. R., Craig, J., Doughty, M., Guillon, J., Smith, G., Tomlinson, A., Eds.; Butterworth-Heinemann: Oxford, UK, 2002; pp. 18-50.

Cursiefen C. Immune privilege and angiogenic privilege of the cornea. Chem Immunol Allergy. 2007; 92:50-57.

Dartt D A, Hodges R R, Zoukhri D. Tears and their secretion. In: Fischbarg J. (editor) The Biology of the Eye. Academic Press, New York, 21-82.

De Campos, A. M. et al. (2001) Chitosan nanoparticles: a new vehicle for the improvement of the delivery of drugs to the ocular surface. Application to cyclosporin A. Int. J. Pharm. 224, 159-168.

de la Fuente M. et al. Chitosan-based nanostructures: a delivery platform for ocular therapeutics. *Adv. Drug Deliv. Rev.* 2010; 62:100-117.

De Paiva C S, Chotikavanich S, Pangelinan S B, et al. IL-17 disrupts corneal barrier following desiccating stress. *Mucosal Immunology* 2009; 2:243-53.

de Paiva C S, Corrales R M, Villarreal A L, et al. Corticosteroid and doxycycline suppress MMP-9 and inflammatory cytokine expression, MAPK activation in the corneal epithelium in experimental dry eye. *Exp Eye Res.* 2006; 83:526-535.

de Paiva C S, Corrales R M, Villarreal A L, Farley W, Li D-Q, Stern M E, Pflugfelder S C. Apical corneal barrier disruption in experimental murine dry eye is abrogated by methylprednisolone and doxycycline. *Invest Ophthalmol Vis Sci.* 2006; 47:2847-2856.

DeStafeno J J, Kim T. Topical bevacizumab therapy for corneal neovascularization. Arch Ophthalmol. 2007; 125: 834-836.

Diebold Y, Calonge M. Applications of nanoparticles in ophthalmology. Prog Retina Eye Res 2010; 29:596-609.

El-Gazayerly, O. N. et al. (1997) Preparation and evaluation of acetazolamide liposomes as ocular delivery systems. Int. J. Pharm. 158, 121-127.

Eye health statistics at a glance, Compiled by American Academy of Ophthalmology, April 2011 http://www.aao.org/newsroom/upload/Eye-Health-Statistics-April-2011.pdf Fantin, A., Vieira, J. M., Gestri, G., Denti, L., Schwarz, Q., Prykhozhij, S., Peri, F., Wilson, S. W. and Ruhrberg, C. (2010) 'Tissue macrophages act as cellular chaperones for vascular anastomosis downstream of VEGF-mediated endothelial tip cell induction', *Blood* 116(5): 829-840.

FDA, *Chiron Vision files FDA application to market intraocular implant for CMV retinitis. Food and Drug Administration.* J Int Assoc Physicians AIDS Care, 1995. 1(6): p. 37.

Fialho, S. L. et al. (2004) New vehicle based on a microemulsion for topical ocular administration of dexamethasone. Clin. Exp. Ophthalmol. 32, 626-632.

Flach, A., *The pilocarpine Ocusert Delivery System.* Trans Pac Coast Otoophthalmol Soc Annu Meet, 1974. 55: p. 179-208.

Francouer M, Ahmed I, Sitek S, Patton T F. Age-related differences in ophthalmic drug disposition. III. Corneal permeability of pilocarpine in rabbits. *Int. J. Pharm.* 1983; 16:203-213.

Friedrich S W, Cheng Y-L, Saville B A. Theoretical corneal permeation model for ionizable drugs. J. Ocul. Pharmacol. 1993; 9:229-249.

Gagen D, Laubinger S, Li Z et al. ICAM-1 mediates surface contact between neutrophils and keratocytes following corneal epithelial abrasion in the mouse. Exp Eye Res 2010; 91:676-84.

Garcia-Hirschfeld J, Lopez-Briones L G, Belmonte C: Neurotrophic influences on corneal epithelial cells. Exp Eye Res 1994, 59:597-605.

Garhwal R, Shady S F, Ellis E J, Ellis J Y, Leahy C D, McCarthy S P, Crawford K S, Gaines P. Sustained ocular delivery of Ciprofloxacin using nanospheres and conventional contact lens materials. *Invest Ophthalmol Vis Sci.* 2012; 53: 1341-1352.

Garty, N. et al. (1994) Pilocarpine in submicron emulsion formulation for treatment of ocular hypertension: a phase II clinical trial. Invest. Ophthalmol. Vis. Sci. 35, 2175.

Gaudana R, Ananthula H K, Parenky A, Mitra A K. Ocular drug delivery. *Am Assoc Pharm Sci J.* 2010; 12:348-360.

Gaudana R, Jwala J, Boddu SHS, Mitra A K. Recent perspectives in ocular drug delivery. *Pharm. Res.* 2008; 26:1197-1216.

Gayton, J L. Etiology, prevalence, and treatment of dry eye disease. Clinical Ophthalmol. 3:405-412, 2009.

Gershkovich P. et al. A review of the application of lipid-based systems in systemic, dermal, transdermal, and ocular drug delivery. Crit. Rev. Ther. Drug 2008; 25:545-584.

Gerten G. Bevacizumab (avastin) and argon laser to treat neovascularization in corneal transplant surgery. Cornea. 2008; 27:1195-1199.

Gipson I. K, Argueso P. Role of mucins in the function of the corneal and conjunctival epithelia. *Int. Rev. Cytol.* 2003; 231:1-49.

Gipson I K. The ocular surface: The challenge to enable and protect vision. *Invest. Ophthalmol. Visual Sci.* 2007; 48:4391-4398.

Gould, D. J., Vadakkan, T. J., Poche, R. A. and Dickinson, M. E. (2011) 'Multifractal and lacunarity analysis of microvascular morphology and remodeling', *Microcirculation* 18(2): 136-51.

Grass G M, Robinson J. R. Mechanisms of corneal drug penetration II: Ultrastructural analysis of potential pathways for drug movement. *J. Pharm. Sci.* 1988; 77, 15-23.

Gulsen D, Chauhan A. Ophthalmic drug delivery through contact lenses. Invest Ophthalmol Vis Sci. 45: 2342-2347, 2004.

Harmia, T. et al. (1986) A solid colloidal drug delivery system for the eye: encapsulation of pilocarpin in nanoparticles. J. Microencapsul. 3, 3-12.

He C, Kim S W, Lee D S, In situ gelling stimuli-sensitive block copolymer hydrogels for drug delivery, *J. Control. Release* 2008; 127:189-207.

Hitzenberger C K, Baumgartner A, Drexler W, Fercher A F. Interferometric measurement of corneal thickness with micrometer precision. Am. J. Ophthalmol. 1994; 118:468-476.

Huang A J W, Tseng S C G, Kenyon K R. Paracellular permeability of corneal and conjunctival epithelia. Invest. Ophthalmol. Vis. Sci. 1989; 30:684-689.

Irache, J. M. et al. (2005) Albumin nanoparticles for the intravitreal delivery of anticytomegaloviral drugs. Mini. Rev. Med. Chem. 5, 293-305.

Jaffe, G. J., et al., Fluocinolone acetonide implant (Retisert) for noninfectious posterior uveitis: thirty-four-week results of a multicenter randomized clinical study. Ophthalmology, 2006. 113(6): p. 1020-7.

Jung H J, Chauhan A. Temperature sensitive contact lenses for triggered ophthalmic drug delivery. *Biomaterials* 2012; 33:2289-2300.

Kane, F. E., et al., Iluvien: a new sustained delivery technology for posterior eye disease. Expert Opin Drug Deliv, 2008. 5(9): p. 1039-46.

Kapoor Y, Chauhan A. Ophthalmic delivery of cyclosporine A from Brij-97 microemulsion and surfactant-laden p-HEMA hydrogels. Int. J. Pharm. 2008; 361:222-229.

Khalil, R. M. et al. (1992) Pilocarpine hydrochloride liposomal ophthalmic drug delivery system. Egypt. J. Pharma. Sci. 33, 667-668

Kristinsson J K. et al. (1996) Dexamethasone-cyclodextrin-polymer co-complexes in aqueous eye drops. Aqueous humor pharmacokinetics in humans. Invest. Ophthalmol. Vis. Sci. 37, 1199-120.

Kubilus J K, Linsenmayer T F: Developmental corneal innervation: interactions between nerves and specialized apical corneal epithelial cells. Invest Ophthalmol Vis Sci 2010, 51:782-789.

Kuno N, Fujii S. Recent advances in ocular drug delivery systems. *Polymers* 2011; 3:193-22.

Lederer C M, Harold R E. Drop size of commercial glaucoma medications. *Am. J. Ophthalmol.* 1986; 101: 691-694.

Lee Y-H, Kompella U B, Lee V H L. Systemic absorption pathways of topically applied β-adrenergic antagonists in the pigmented rabbit. *Exp Eye Res*. 1993; 57:341-349.

Lee, P., Y. Shen, and M. Eberle, *The long-acting Ocusert-pilocarpine system in the management of glaucoma*. Invest Ophthalmol, 1975. 14(1): p. 43-6.

Leslie-Barbick, J. E., Saik, J. E., Gould, D. J., Dickinson, M. E. and West, J. L. (2011) 'The promotion of microvasculature formation in poly(ethylene glycol) diacrylate hydrogels by an immobilized VEGF-mimetic peptide', *Biomaterials* 32(25): 5782-9.

Li X. et al. A controlled-release ocular delivery system for ibuprofen based on nanostructured lipid carriers. Int. J. Pharm. 2008; 363:177-182.

Li Z, Burns A R, Byeseda M S, Smith C W. CCL20, {gamma}{delta} T cells, and IL-22 in corneal epithelial healing. FASEB J 2011; 25:2659-68.

Li Z, Burns A R, Han L, Rumbaut R E, Smith C W. IL-17 and VEGF are necessary for efficient corneal nerve regeneration. Amer J Pathol 2011; 178:1106-16.

Li Z, Burns A R, Smith C W. Lymphocyte function-associated antigen-1-dependent inhibition of corneal wound healing. Am J Pathol 2006; 169:1590-600.

Li Z, Burns A R, Smith C W. Two waves of neutrophil emigration in response to corneal epithelial abrasion: distinct adhesion molecule requirements. Invest Ophthalmol Vis Sci 2006; 47:1947-55.

Li Z, Rumbaut R E, Burns A R, Smith C W. Platelet Response to Corneal Abrasion Is Necessary for Acute Inflammation and Efficient Re-epithelialization. Invest Ophthalmol Vis Sci 2006; 47:4794-802.

Liaw J, Robinson J R. (1992) The effect of polyethylene glycol molecular weight on corneal transport and the related influence of penetration enhancers. Int. J. Pharm. 1992; 88:125-140.

Liaw J, Rojanasakul Y, Robinson J R. The effect of drug charge type and charge density on corneal transport. *Int. J. Pharm*. 1992; 88:111-124.

Lim, L. L., J. R. Smith, and J. T. Rosenbaum, *Retisert (Bausch & Lomb/Control Delivery Systems)*. Curr Opin Investig Drugs, 2005. 6(11): p. 1159-67.

Liu Q, Smith C W, Zhang W, Burns A R, Li Z. N K Cells Modulate the Inflammatory Response to Corneal Epithelial Abrasion and Thereby Support Wound Healing. Am J Pathol 2012.

Loftsson, T. et al. (1994) The effect of hydroxypropyl methylcellulose on release of dexamethasone from aqueous 2-hydroxypropyl-β-cyclodextrin formulations. Int. J. Pharm. 104, 181-184.

Lopez B D, Ubels J L. Artificial tear composition and promotion of recovery of the damaged corneal epithelium. *Cornea*. 1993; 12:115-120.

Lopez B D, Ubels J L. Quantitative evaluation of the corneal epithelial barrier: effect of artificial tears and preservatives. *Curr Eye Res*. 1991; 10:645-656.

Luo L, Li D Q, Doshi A, Farley W, Corrales R M, Pflugfelder S C. Experimental dry eye stimulates production of inflammatory cytokines and MMP-9 and activates MAPK signaling pathways on the ocular surface. *Invest Ophthalmol Vis Sci*. 2004; 45:4293-4301.

Mack B C, Wright K W, Davis, M E. A biodegradable filament for controlled drug delivery. J. Control. Release 2009; 139:205-211

Mackie I A: Role of the corneal nerves in destructive disease of the cornea. Trans Ophthalmol Soc UK 1978, 98:343-347.

Macoul, K. L. and D. Pavan-Langston, *Pilocarpine ocusert system for sustained control of ocular hypertension*. Arch Ophthalmol, 1975. 93(8): p. 587-90.

Mahmoud S S. et al. Liposomal phospholipid preparations of chloramphenicol for ophthalmic applications. J. Pharm. Sci. 2008; 97:2691-2701

Mannermaa E, Vellonen K-S, Urtti A. Drug transport in corneal epithelium and blood-retina barrier: Emerging role of transporters in ocular pharmacokinetics. *Adv Drug Deliv Rev*. 2006; 58:1136-1163.

Maren T H, Jankowska L. Ocular pharmacology of sulfonamides: the cornea as barrier and depot. *Curr. Eye Res*. 1985; 4:399-408.

Maurice D M, Mishima S. Ocular pharmacokinetics. Sears, M C (Ed.), Handbook of Experimental Pharmacology. Vol. 69, Pharmacology of the Eye. Springer-Verlag, Berlin-Heidelberg 1984; 19-116.

Meseguer G, Gurny R, Burl P, Rozier A, Plazonnet B. Gamma scintigraphic study of precorneal drainage and assessment of miotic response in rabbits of various ophthalmic formulations containing pilocarpine. Int. J. Pharm. 1993; 95:229-234.

Miljanoviae B, Dana R, Sullivan D A, Schaumber D A. Impact of dry eye syndrome on vision-related quality of life. *Am J Ophthalmol*. 2007; 143:409-415.

Mishima S. et al. Determination of tear volume and tear flow. Invest. Ophthalmol. 1966; 5:264-276.

Mitra A K, Mikkelson T J. Mechanism of transcorneal permeation of pilocarpine. *J. Pharm. Sci*. 1988; 77:771-775.

Moon, J. J., Saik, J. E., Poche, R. A., Leslie-Barbick, J. E., Lee, S. H., Smith, A. A., Dickinson, M. E. and West, J. L. (2010) 'Biomimetic hydrogels with pro-angiogenic properties', *Biomaterials* 31(14): 3840-7.

Muller L J, Marfurt C F, Kruse F, Tervo T M: Corneal nerves: structure, contents and function. Exp Eye Res 2003, 76:521-542.

Nagelhout T J, Gamache D A, Roberts L, et al. Preservation of tear film integrity and inhibition of corneal injury by dexamethasone in a rabbit model of lacrimal gland inflammation-induced dry eye. *J Ocu Pharmaco Ther*. 2005; 21:139-148.

Newell F W. Ophthalmology, Principles and Concepts, 6th edn. 1986; C. V Mosby Co., St. Louis, Mo.

Park K, Shalaby W S W, Park H. Biodegradable Hydrogels for Drug Delivery, Technomic Publishing, Lancaster, Pa., 1993.

Peng C-C, Chauhan A. Extended cyclosporine delivery by silicone-hydrogel contact lenses. *J Control Release* 2011; 154: 267-274.

Peppas N A, Hilt J Z, Khademhosseini A, Langer R. Hydrogels in biology and medicine: molecular principles to bionanotechnology, *Adv. Mater* 2006; 18: 1345-1360.

Petrescu M S, Larry C L, Bowden R A et al. Neutrophil interactions with keratocytes during corneal epithelial wound healing: a role for CD18 integrins. Invest Ophthalmol Vis Sci 2007; 48:5023-9.

Pflugfelder S C, Farley W, Luo L, et al. Matrix metalloproteinase-9 knockout confers resistance to corneal epithelial barrier disruption in experimental dry eye. *Am J Pathol.* 2005; 166:61-71.

Pflugfelder S C, Geerling G, Kinoshita S, Lemp M A, McCulley J, Nelson D, Novack G N, Shimazaki J, Wilson C. Management and therapy of dry eye disease: Report of the management and therapy subcommittee of the international dry eye workshop. Ocul Surf 5:163-178, 2007.

Pignatello, R. et al. (2002) Flurbiprofen-loaded acrylate polymer nanosuspensions for ophthalmic application. Biomaterials 23, 3247-3255.

Poche, R. A., Larina, I. V., Scott, M. L., Saik, J. E., West, J. L. and Dickinson, M. E. (2009) 'The Flk1-myr::mCherry mouse as a useful reporter to characterize multiple aspects of ocular blood vessel development and disease', *Developmental dynamics: an official publication of the American Association of Anatomists* 238(9): 2318-26.

Poche, R. A., Saik, J. E., West, J. L. and Dickinson, M. E. (2010) 'The mouse cornea as a transplantation site for live imaging of engineered tissue constructs', Cold Spring Harbor protocols 2010(4): pdb prot5416.

Qian, B., Deng, Y., Im, J. H., Muschel, R. J., Zou, Y., Li, J., Lang, R. A. and Pollard, J. W. (2009) 'A distinct macrophage population mediates metastatic breast cancer cell extravasation, establishment and growth', *PloS one* 4(8): e6562.

Rae, F., Woods, K., Sasmono, T., Campanale, N., Taylor, D., Ovchinnikov, D. A., Grimmond, S. M., Hume, D. A., Ricardo, S. D. and Little, M. H. (2007) 'Characterisation and trophic functions of murine embryonic macrophages based upon the use of a Csf1r-EGFP transgene reporter', *Developmental biology* 308(1): 232-46.

Reim M, Redbrake C, Schrage N. Chemical and thermal injuries of the eyes. Surgical and medical treatment based on clinical and pathophysiological findings. *Arch Soc Esp Oftalmol.* 2001; 76:79-124.

Reinstein D Z, Silverman R H, Rondeau M J, Coleman D J. Epithelial and corneal thickness measurements by high-frequency ultrasound digital signal processing. *Ophthalmology* 1994; 101:140-146.

Rojanasakul Y, Wang L-Y, Bhat M, Glover D D, Malanga C, Ma J K H. The transport barrier of epithelia: a comparative study on membrane permeability and charge selectivity in the rabbit. Pharm. Res. 1992; 9:1029-1034.

Saik, J. E., Gould, D. J., Keswani, A. H., Dickinson, M. E. and West, J. L. (2011a) 'Biomimetic hydrogels with immobilized ephrinA1 for therapeutic angiogenesis', *Biomacromolecules* 12(7): 2715-22.

Saik, J. E., Gould, D. J., Watkins, E. M., Dickinson, M. E. and West, J. L. (2011b) 'Covalently immobilized platelet-derived growth factor-BB promotes angiogenesis in biomimetic poly(ethylene glycol) hydrogels', *Acta biomaterialia* 7(1): 133-43.

Saika S, Ikeda K, Yamanaka O, et al. Therapeutic effects of adenoviral gene transfer of bone morphogenic protein-7 on a corneal alkali injury model in mice. *Lab Invest.* 2005; 85:474-486.

Sasmono, R. T., Oceandy, D., Pollard, J. W., Tong, W., Pavli, P., Wainwright, B. J., Ostrowski, M. C., Himes, S. R. and Hume, D. A. (2003) 'A macrophage colony-stimulating factor receptor-green fluorescent protein transgene is expressed throughout the mononuclear phagocyte system of the mouse', *Blood* 101(3): 1155-63.

Schoenwald R D, Huang H-S. (1983) Corneal penetration behavior of β-blocking agents I: physicochemical factors. *J. Pharm. Sci.* 1983; 72, 1266-1272.

Seyfoddin A. et al. Solid lipid nanoparticles for ocular drug delivery. Drug Deliv. 2010; 17:467-489.

Shell J W. Ophthalmic drug delivery systems. *Surv. Ophthalmol.* 1984; 29:117-128.

Shih R-L, Lee V H L. Rate limiting barrier to the penetration of ocular hypotensive β-blockers across the corneal epithelium in the pigmented rabbit. *J. Ocul. Pharmacol.* 1990; 6:329-336.

Sieg J W, Robinson J R. Mechanistic studies on transcorneal permeation of pilocarpine, *J. Pharm. Sci.* 1976; 65:1816-1822.

Sieg J W, Robinson, J R. (1977) Vehicle effects on ocular drug bioavailability II: Evaluation of pilocarpine. J. Pharm. Sci. 1977; 66:1222-1228.

Singh K, Nair A B, Kumar A, Kumria R. Novel approaches in formulation and drug delivery using contact lenses. J Basic Clin Pharmacy 2011; 2:87-101.

Singh V, Ahmad R, Heming T. The challenges of ophthalmic drug delivery: A review. Int J Drug Discovery. 2011; 3:56-62.

Solomon A, Dursun D, Liu Z, Xie Y, Macri A, Pflugfelder S C. Pro- and anti-inflammatory forms of interleukin-1 in the tear fluid and conjunctiva of patients with dry-eye disease. *Invest Ophthalmol Vis Sci.* 2001; 42:2283-2292.

Souto E B. et al. Feasibility of lipid nanoparticles for ocular delivery of anti-inflammatory drugs. Curr. Eye Res. 2010; 35:537-552.

Sultana Y, Aqil M, Ali A, Samad A. Advances in the topical ocular drug delivery, *Expert Rev Ophthalmology*, 2007; 2(2):309-23.

Sultana, Y. et al. Nanotechnology in ocular delivery: current and future directions. Drugs Today 2011; 47:441-455.

Sweet, M. J. and Hume, D. A. (2003) 'CSF-1 as a regulator of macrophage activation and immune responses', *Archivum immunologiae et therapiae experimentalis* 51(3): 169-77.

Ufret-Vincenty, R. L., et al., *Cytomegalovirus retinitis after fluocinolone acetonide (Retisert) implant.* Am J Ophthalmol, 2007. 143(2): p. 334-5.

Urtti A, Pipkin J D, Rork G, Sendo T, Finne U, Repta A J. Controlled drug delivery devices for experimental ocular studies with timolol 2. Ocular and systemic absorption in rabbits, *Int. J. Pharm.* 1990; 61:241-249.

Urtti A, Salminen L. Minimizing systemic absorption of topically administered ophthalmic drugs. *Surv. Ophthalmol.* 1993; 37:435-456.

Urtti A. Challenges and obstacles of ocular pharmacokinetics and drug delivery. *Adv Drug Deliv Rev.* 2006; 58:1131-1135.

Vandamme, T. F. A. et al. (2005) Poly(amidoamine) dendrimers as ophthalmic vehicles for ocular delivery of pilocarpine nitrate and tropicamide. J. Contr. Rel. 102, 23-38.

Vandervoort J, Ludwig A. Ocular drug delivery: nanomedicine applications. Nanomed 2007; 2:11-21.

Watsky M A, Jablonski M M, Edelhauser H F. Comparison of conjunctival and corneal surface areas in rabbit and human. *Curr. Eye Res*. 1988; 7:483-486.

Yanez F, Martikainen L, Braga MEM, Alvarez-Lorenzo C, Concheiro A, Duarte C M M, Gil M H, de Sousa H C. Supercritical fluid-assisted preparation of imprinted contact lenses for drug delivery. *Acta Biomaterialia* 2011; 7: 1019-1030.

Zaki I, Fitzgerald P, Hardy J G, Wilson C G. A comparison of the effect of viscosity on the precorneal residence of solutions in rabbit and man. *J. Pharm. Pharmacol*. 1986; 38:463-466.

Zhang, J., Cao, R., Zhang, Y., Jia, T., Cao, Y. and Wahlberg, E. (2009) 'Differential roles of PDGFR-alpha and PDGFR-beta in angiogenesis and vessel stability', *The FASEB journal: official publication of the Federation of American Societies for Experimental Biology* 23(1): 153-63.

Zoukhri D. Effect of inflammation on lacrimal gland function. *Exp Eye Res*. 2006; 82:885-898.

What is claimed is:

1. A device for delivering therapeutics to an eye comprising:
    a hydrogel matrix comprising at least one biocompatible material; and
    a plurality of reservoirs disposed in the hydrogel matrix;
    wherein at least a portion of a surface of the hydrogel matrix containing an open end of the plurality of reservoirs is configured to contact an exterior a surface of a user's eye and dissolves upon contact with the exterior surface of the user's eye.

2. The device of claim 1 wherein dissolution of the surface portion of hydrogel matrix occurs at a predetermined rate.

3. The device of claim 2 wherein the predetermined rate of dissolution is based at least on the biocompatible material.

4. The device of claim 1 wherein the at least one biocompatible material comprises at least one of the following: dextran, polyvinyl alcohol, carboxy methyl cellulose, hydroxypropyl cellulose, polyvinylpyrrolidone, polyvinyl alcohol (PVA), Polylactide-co-glycolide (PLGA), polyhydroxy ethyl methacrylate (PolyHEMA), Polyhydroxy ethylacrylate, gelatin materials, collagen materials, and any combination thereof.

5. The device of claim 1 wherein the device is configured to release a portion of a substance contained in the reservoirs upon contact with the exterior surface of the user's eye.

6. The device of claim 5 wherein the device is configured to release the substance in the reservoirs for at least 5 days.

7. The device of claim 5 wherein the dissolution of the surface portion of the hydrogel matrix contacting the exterior surface of the user's eye releases a portion of the substance in the reservoirs.

8. The device of claim 5 wherein the substance in the reservoirs comprises a therapeutic.

9. The device of claim 8 wherein the therapeutic is selected from the group consisting of chemical compounds, drugs, including anti-inflammatory agents, as well as drug matrices, other small molecule drugs, antibodies, antibiotics, siRNAs, peptides, steroids, including corticosteroids, biologic antifungal agents, amino acids, mRNAs, nutrient supplements, or any combination thereof.

10. The device of claim 1 wherein the hydrogel matrix is configured to completely dissolve after a predetermined period of time.

11. The device of claim 1 wherein at least one reservoir has a depth of about 500 nm.

12. The device of claim 1 wherein the hydrogel matrix has a surface area of about 1 square mm to 50 square mm.

13. A method for fabricating and using a therapeutics dispensing device comprising the steps of:
    forming a template comprising a base component and a plurality of posts attached to a surface of the base component;
    providing a biocompatible material layer with a thickness greater than a length of the posts adjacent said base portion;
    separating said biocompatible material layer from said template to form a hydrogel matrix with a plurality of open reservoirs corresponding to the posts;
    injecting a therapeutic into at least one reservoir while maintaining the hydrogel matrix for therapeutic function; and
    providing the hydrogel matrix and therapeutic to an exterior surface of a patient's eye.

14. The method of claim 13 wherein the therapeutic is selected from the group consisting of chemical compounds, drugs, including anti-inflammatory agents, as well as drug matrices, other small molecule drugs, antibodies, antibiotics, siRNAs, peptides, steroids, biologic antifungal agents, amino acids, mRNAs, nutrient supplements, and any combination thereof.

15. The method of claim 13 wherein forming a template comprises microfabricating said template.

16. The method of claim 15 wherein said microfabrication comprises e-beam lithography followed by plasma etching.

17. A method of treating an ocular medical condition in an individual, comprising the step of applying a device of claim 1 to an exterior surface of an eye of the individual, wherein at least one of the plurality of reservoirs comprises at least one therapeutic composition.

18. The method of claim 17, wherein the ocular medical condition is selected from the group consisting of a corneal disease, corneal inflammation, corneal injury, dry eye disease, ocular infections, eye injury, ocular burn injury, wound healing, nerve regeneration after corneal injury, LASIK, corneal transplant, corneal ulcers, prevention/treatment of corneal neovascularization and angiogenesis, corneal cystinosis, glaucoma, diabetic retinopathy, and macular degeneration.

19. The method of claim 17, wherein the ocular medical condition is an ocular surface inflammation, infection, or both.

20. The method of claim 17, wherein the ocular medical condition is cystinosis.

21. The method of claim 17, wherein the device is applied on a cornea, on a conjunctiva, or in a fornix.

22. The method of claim 17, wherein the therapeutic composition comprises a drug.

23. The method of claim 22, wherein the drug is riboflavin, doxycycline, dexamethasone, tacrolimus, topiramate, etifoxine, vinaxanthone, and neotrofin, sorafenib, sunitinib, cyclosporin A, avastin, ciproflaxacin, levofloxacin, erythromycin, azithromycin, acyclovir, valacyclovir, ganciclovir, cysteamine, brucellamine, tiopronin, anti-IFNγ, limbal stem cells, or a combination thereof.

24. The method of claim 20, wherein the drug is cysteamine, brucellamine, tiopronin, polythiols, thiopolymers (thiomers), or a combination thereof.

25. A method of delivering at least one therapeutic composition to an individual for nerve regeneration in at least one eye, comprising applying a device of claim 1 to the individual, wherein at least one of the plurality of reservoirs comprises the therapeutic composition.

26. The method of claim 25, wherein the individual is in need of nerve regeneration after LASIK surgery.

27. The method of claim 25, wherein the individual is in need of nerve regeneration after corneal transplant or corneal injury.

28. The device of claim 1, wherein an exterior surface of the eye is selected from the group consisting of a cornea, a bulbar conjunctiva, a tarsal conjunctiva, under the lower eyelid, the conjunctival fornix.

* * * * *

UNITED STATES PATENT AND TRADEMARK OFFICE
CERTIFICATE OF CORRECTION

PATENT NO. : 10,251,778 B2
APPLICATION NO. : 14/420295
DATED : April 9, 2019
INVENTOR(S) : Ghanashyam Acharya et al.

It is certified that error appears in the above-identified patent and that said Letters Patent is hereby corrected as shown below:

In the Specification

Column 1, Lines 12-14 (approx.), should read:
"This invention was made with government support under R01 EY011915-14 awarded by the National Institutes of Health. The government has certain rights in the invention."

Signed and Sealed this
Twenty-fourth Day of March, 2020

Andrei Iancu
*Director of the United States Patent and Trademark Office*